United States Patent [19]

Himmelsbach et al.

[11] Patent Number: 5,827,849

[45] Date of Patent: Oct. 27, 1998

[54] CYCLIC DERICATIVES, PHARMACEUTICAL COMPOSITIONS CONTAINING THESE COMPOUNDS AND PROCESSES FOR PREPARING THEM

[75] Inventors: F. Himmelsbach, Mittelbiberach; Helmut Pieper; Volkhard Austel, both of Biberach; Günter Linz, Mittelbiberach; Brian Guth, Warthausen; Thomas Müller, Edewecht; Johannes Weisenberger, Biberach, all of Germany

[73] Assignee: Karl Thomae GmbH, Biberach an der Riss, Germany

[21] Appl. No.: 768,365

[22] Filed: Dec. 17, 1996

Related U.S. Application Data

[62] Division of Ser. No. 434,136, May 2, 1995, Pat. No. 5,612,335, which is a division of Ser. No. 200,125, Feb. 22, 1994, Pat. No. 5,519,036.

[30] Foreign Application Priority Data

Feb. 22, 1993 [DE] Germany .......................... 43 05 388.2
Sep. 22, 1993 [DE] Germany .......................... 43 32 168.2
Jun. 17, 1996 [DE] Germany .......................... 196 24 069.7

[51] Int. Cl.$^6$ ....................... C07D 403/04; A61K 31/415

[52] U.S. Cl. ............................................. 514/215; 540/578

[58] Field of Search ............................. 540/578; 574/215

[56] References Cited

U.S. PATENT DOCUMENTS 5,519,036 5/1996 Himmelsbach et al. ................. 514/213
5,612,335 3/1997 Himmelsbach et al. ................. 514/213

*Primary Examiner*—Zinna Northington Davis
*Attorney, Agent, or Firm*—R. P. Raymond; M-E. M. Devlin; A. R. Stempel

[57] ABSTRACT

The invention relates to cyclic derivatives of general formula

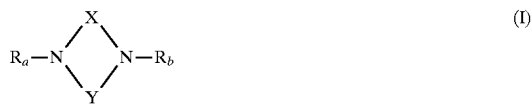

wherein $R_a$, $R_b$, X and Y are as defined in claim 1, the tautomers, the stereoisomers including the mixtures thereof and the salts thereof, particularly the physiologically acceptable salts thereof with organic or inorganic acids or bases, which have valuable pharmacological properties, preferably aggregation-inhibiting effects, pharmaceutical compositions containing the compounds and processes for preparing them.

7 Claims, No Drawings

CYCLIC DERICATIVES, PHARMACEUTICAL COMPOSITIONS CONTAINING THESE COMPOUNDS AND PROCESSES FOR PREPARING THEM

This application is a divisional application of prior U.S. Ser. No. 08/434,136, filed May 2, 1995, and now U.S. Pat. No. 5,612,235, which is in turn a divisional application of U.S. Ser. No. 08/200,125, filed Feb. 22, 1994, and now U.S. Pat. No. 5,519,036.

The invention relates to cyclic derivatives of general formula

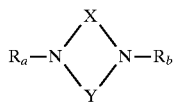

the tautomers, the stereoisomers including the mixtures thereof and the salts thereof, particularly the physiologically acceptable salts thereof with inorganic or organic acids or bases which have, inter alia, valuable pharmacological properties, preferably aggregation-inhibition properties, to pharmaceutical compositions containing these compounds, to their use and to processes for preparing them.

In general formula I above:

X denotes a carbimino group optionally substituted at the nitrogen atom by an alkyl, aryl, heteroaryl or cyano group, or a carbonyl, thiocarbonyl, sulphonyl, 1-nitro-ethen-2,2-diyl or 1,1-dicyano-ethen-2,2-diyl-group;

Y denotes a straight chain $C_{2-4}$-alkylene or alkenylene group which is optionally substituted by $R_c$ or $R_d$ or by $R_c$ and $R_d$, and which may additionally be substituted by one or two alkyl groups and wherein additionally one or two methylene groups may each be replaced by a carbonyl group, or a 1,2-cycloalkylene group containing 5 to 7 carbon atoms optionally substituted by $R_c$ or $R_d$ or by $R_c$ and $R_d$, or a 1,2-cycloalkenylene group containing 5 to 7 carbon atoms optionally substituted by $R_c$ or $R_d$ or by $R_c$ and $R_d$, or a 1,2 arylene group, or a 1,2 phenylene group in which one or two methine groups are each replaced by a nitrogen atom or wherein one or two —CH=CH— groups are each replaced by a —CO—NH group or wherein one methine group is replaced by a nitrogen atom and one —CH=CH— group is replaced by a —CO—NH group, whilst the above-mentioned heterocyclic groups may additionally be substituted by one or two alkyl groups, or a —CO—NH—, —NH—CO—, —CH=N— or —N=CH— group optionally substituted by $R_c$ or $R_d$, a first of the groups $R_a$ to $R_d$ denotes an A—B group wherein A is a group of one of the formulae

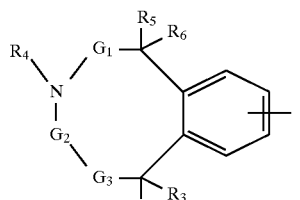

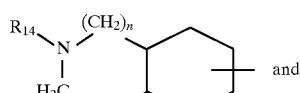

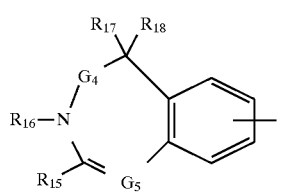

wherein the benzo moiety of the above-mentioned groups may be mono-substituted by $R_{25}$, or mono- or di-substituted by $R_{26}$, or mono-substituted by $R_{25}$ and additionally mono-substituted by $R_{26}$, wherein the substituents $R_{25}$ and $R_{26}$, which may be identical or different, are defined as follows, and additionally in the above-mentioned benzo moiety one to three methine groups may each be replaced by a nitrogen atom, or a —CH=CH— group may be replaced by a —CO—NR$_1$— group, or a methine group may be replaced by a nitrogen atom and a CH=CH— group by a —CO—NR$_1$ group, wherein $R_1$ denotes a hydrogen atom or an alkyl group, $G_1$ and $G_4$ each represent a bond or a methylene group which may be mono or disubstituted by an alkyl, aryl or a heteroaryl group, wherein the substituents may be identical or different, $G_2$ denotes a bond or a methylene group substituted by $R_7$ and $R_8$, $G_3$ denotes a bond or a methylene group substituted by $R_9$ and $R_{10}$, or, if $G_2$ does not denote a bond, $G_3$ may also denote a carbonyl group, $G_5$ denotes a nitrogen atom or a methine group optionally substituted by an alkyl, aryl or heteroaryl group, $R_2$ denotes a hydrogen atom or an alkyl, aryl or heteroaryl group or, if at least one of $G_2$ and $G_3$ does not denote a bond, $R_2$ may also denote a hydroxy or alkoxy group, $R_3$ denotes a hydrogen atom or an alkyl, aryl or heteroaryl group, or, if at least one of groups $G_2$ and $G_3$ does not denote a bond, $R_3$ together with $R_2$ may also denote an oxygen atom, $R_4$ and $R_{14}$ each denote a hydrogen atom, a cycloalkyl or cycloalkylalkyl group each having 3 to 7 carbon atoms in the cycloalkyl moiety, a $C_{1-8}$-alkyl group, a $C_{3-8}$-alkenyl group (which alkenyl group may not be connected to the nitrogen atom via the vinyl moiety), or a hydroxyalkyl, alkoxyalkyl, aminoalkyl, alkylaminoalkyl, dialkylaminoalkyl, cyanoalkyl, carboxyalkyl, alkoxycarbonylalkyl, aminocarbonylalkyl, N-alkylaminocarbonylalkyl, N,N-dialkylaminocarbonylalkyl, arylalkyl, heteroarylalkyl, alkoxycarbonyl, arylmethyloxycarbonyl, formyl, acetyl, trifluoroacetyl, allyloxycarbonyl, amidino or $R_{11}CO—O—(R_{12}CR_{13})—O—CO$ group, wherein $R_{11}$ denotes a $C_{1-8}$ alkyl group, a $C_{5-7}$ cycloalkyl group or an aryl or arylalkyl group, $R_{12}$ denotes a hydrogen atom, an alkyl group, a $C_{5-7}$ cycloalkyl group or an aryl group and $R_{13}$ denotes a hydrogen atom, or an alkyl group, or $R_4$ together with $R_3$ denotes a straight chain alkylene group having a 2 to 4 carbon atoms or, if $G_2$ does not represent a bond, $R_4$ may denote a methylene group, $R_5$ denotes a hydrogen atom, an alkyl, aryl or heteroaryl group or, if $G_1$ does not represent a bond, $R_5$ may also denote a hydroxy or alkoxy group or, if $G_1$ does represent a bond, $R_4$ together with $R_5$ may denote another bond and $R_6$ represents a hydrogen atom, an alkyl, aryl or heteroaryl group or, if $G_1$ represents a bond and $R_4$ together with $R_5$ represents another bond, $R_6$ may represent a chlorine atom or a hydroxy, methoxy, amino, alkylamino, or dialkylamino group, or, if $G_1$ does not denote a bond, $R_6$ together with $R_5$ may denote an oxygen atom, $R_7$ denotes a hydrogen atom or an alkyl, aryl or heteroaryl group, $R_8$ denotes a hydrogen atom or an alkyl, aryl or heteroaryl group or $R_8$ together with $R_4$ may denote a straight chain $C_{2-5}$-alkylene group, $R_9$ denotes a hydrogen atom or an alkyl, aryl or heteroaryl group or, if $G_2$ does not represent a bond, $R_9$ may also represent a hydroxy or alkoxy group, $R_{10}$ denotes a hydrogen atom or an alkyl, aryl or heteroaryl group or $R_{10}$ together with $R_4$ may denote a straight chain $C_{2-4}$-alkylene group, $R_{15}$ denotes a hydrogen or chlorine atom or an alkyl, aryl, heteroaryl, hydroxy, methoxy, amino, alkylamino or dialkylamino group, $R_{16}$ denotes a hydrogen atom, a cycloalkyl or cycloalkylalkyl group each having 3 to 7 carbon atoms in the cycloalkyl moiety, a $C_{1-8}$-alkyl group, a $C_{3-8}$-alkenyl group (which alkenyl group may not be connected to the nitrogen atom via the vinyl group), or a hydroxyalkyl, alkoxyalkyl, aminoalkyl, alkylaminoalkyl, dialkylaminoalkyl, cyanoalkyl, carboxyalkyl, alkoxycarbonylalkyl, aminocarbonylalkyl, N-alkylaminocarbonylalkyl, N,N-dialkylaminocarbonylalkyl or arylalkyl group, $R_{17}$ denotes a hydrogen atom or an alkyl group or, if $G_4$ denotes a bond, $R_{16}$ together with $R_{17}$ may denote another bond, $R_{18}$ denotes a hydrogen atom or an alkyl group or, if $G_4$ represents a bond and $R_{16}$ and $R_{17}$ together represent another bond, $R_{18}$ may denote a fluorine, chlorine or bromine atom or a hydroxy, methoxy, amino, alkylamino or dialkylamino group and n represents the number 1 or 2, and B denotes a bond, a $C_{1-6}$-alkylene, $C_{2-6}$-alkenylene, or arylene group, or a pyridinylene, pyrimidinylene, pyrazinylene, or pyridazinylene group, wherein one or two —CH=N— groups may each be replaced by a —CO—NH— group and one of the nitrogen atoms instead of being bound to a hydrogen atom may be bound to the group A, whilst the above-mentioned heterocyclic groups may additionally be substituted by one or two alkyl groups, or B denotes a $C_{4-7}$-cycloalkylene group optionally substituted by one or two alkyl groups, or a $C_{5-7}$-cycloalkylene group which is optionally substituted by one or two alkyl groups, and in which a >CH unit is replaced by a nitrogen atom, whilst additionally in the above-mentioned 5 to 7 membered rings a methylene group adjacent to a nitrogen atom may be replaced by a carbonyl group;

a second of the groups $R_a$ to $R_d$ denotes a group of formula

F—E—D— wherein D denotes a $C_{1-6}$-alkylene group wherein a methylene group may be replaced by an oxygen or sulphur atom or by a sulphinyl, sulphonyl or $NR_{19}$ group, or wherein an ethylene group may be replaced by a —CO—$NR_{20}$— or —$NR_{20}$—CO— group (wherein $R_{19}$ denotes a hydrogen atom or an alkyl, alkylcarbonyl, alkylsulphonyl, arylcarbonyl or arylsulphonyl group and $R_{20}$ denotes a hydrogen atom or an alkyl group), or D denotes a $C_{2-6}$-alkenylene, or an arylene group, or a pyridinylene, pyrimidinylene, pyrazinylene or pyridazinylene group wherein one or two —CH=N— groups may each be replaced by a —CO—NH— group and one of the nitrogen atoms, instead of being bound to a hydrogen atom, may be bound to the group E, provided that this does not itself represent a bond or does not adjoin the group D with a heteroatom or a carbonyl group, whilst the above-mentioned heterocyclic groups may additionally be substituted by one or two alkyl groups, or D denotes an indanylene, naphthylene, 1,2,3,4-tetrahyrdonaphthylene or benzosuberanylene group in which one of the rings is bound to the group E and the other ring is bound to the cyclic group of general formula I, whilst the saturated rings may each be substituted by one or two alkyl groups and the aromatic rings may each be substituted by a fluorine, chlorine, bromine or iodine atom or by an alkyl, trifluoromethyl, hydroxy, alkoxy, alkylsulphenyl, alkylsulphinyl, alkylsulphonyl or cyano group, or a $C_{4-7}$-cycloalkylene group optionally substituted by one or two alkyl groups, or a $C_{5-7}$-cycloalkylene group which is optionally substituted by one or two alkyl groups and in which a >CH unit is replaced by a nitrogen atom, whilst moreover in the above-mentioned 5 to 7 membered rings a methylene group adjacent to a nitrogen atom may be replaced by a carbonyl group, or a piperazinylene group which is optionally substituted by one or two alkyl groups and in which a methylene group adjacent to a nitrogen atom may be replaced by a carbonyl group, or, if E represents a cyclic imino group, D may also denote an alkylenecarbonyl group having a total of 2 to 6 carbon atoms, wherein the carbonyl group is bound to the nitrogen atom of the cyclic imino group of group E, or, if E does not represent a bond, D may represent a bond, E denotes a bond, or a $C_{1-6}$-alkylene group which may be substituted by 1 or 2 $C_{1-8}$-alkyl groups, by a $C_{2-4}$-alkenyl or $C_{2-4}$-alkynyl group, by a hydroxy, amino, aryl or heteroaryl group, by a $C_{1-8}$-alkoxy or $C_{1-8}$-alkylamino group, by a dialkylamino group having a total of 2 to 10 carbon atoms, or by an $HNR_{21}$ or N-alkyl-$NR_{21}$ group, wherein $R_{21}$ denotes an alkylcarbonyl or alkylsulphonyl group each having 1 to 8 carbon atoms in the alkyl moiety, an alkyloxycarbonyl group having a total of 2 to 5 carbon atoms, a cycloalkylcarbonyl or cycloalkylsulphonyl group each having 5 to 7 carbon atoms in the cycloalkyl moiety, or an arylalkylcarbonyl, arylalkylsulphonyl, arylalkoxycarbonyl, arylcarbonyl or arylsulphonyl group, or a $C_{2-6}$ alkenylene group, or an arylene group, or a pyridinylene, pyrimidinylene, pyrazinylene or pyridazinylene group optionally substituted by one or two alkyl groups, or a $C_{5-7}$-cycloalkylene group which is optionally substituted by one or two alkyl groups and in which a >CH unit is replaced by a nitrogen atom linked to a carbon atom of the group D, or a $C_{4-7}$-cycloalkylene group optionally substituted by one or two $C_{1-8}$-alkyl groups, by a $C_{2-4}$-alkenyl or $C_{2-4}$-alkynyl group, by a hydroxy, amino, aryl or heteroaryl group, by a $C_{1-8}$-alkoxy or $C_{1-8}$-alkylamino group, by a dialkylamino group having a total of 2 to 10 carbon atoms, or by an $HNR_{21}$ or N-alkyl-$NR_{21}$, (wherein $R_{21}$ is as hereinbefore defined), or, if D does not denote a bond, an alkylene group linked to group D via a group W, wherein W denotes an oxygen or sulphur atom or a sulphinyl, sulphonyl, $NR_{19}$, $NR_{20}$—CO—, or —CO—$NR_{20}$— group, wherein $R_{19}$ and $R_{20}$ are as hereinbefore defined and the alkylene group may additionally be substituted by one or two $C_{1-8}$-alkyl groups, by a $C_{2-4}$-alkenyl or $C_{2-4}$-alkynyl group, by a hydroxy, amino, aryl or heteroaryl group, by a $C_{1-8}$ alkoxy or $C_{1-8}$-alkylamino group, by a dialkylamino group containing a total of 2 to 10 carbon atoms, by an $HNR_{21}$ or N-alkyl-$NR_{21}$-group, wherein the heteroatom of the additional substituent is separated from a heteroatom of the group W by at least two carbon atoms and $R_{21}$ is as hereinbefore defined, and F denotes a carbonyl group substituted by a hydroxy group, by a $C_{1-8}$-alkoxy group, by an arylalkoxy group or by an $R_{22}O$ group, wherein $R_{22}$ denotes a $C_{4-8}$-cycloalkyl group or a cycloalkylalkyl group having 3 to 8 carbon atoms in the cycloalkyl moiety, wherein the cycloalkyl group may be substituted by an alkyl, alkoxy or dialkylamino group, by an alkyl group and by 1 to 3 methyl groups, and wherein additionally a methylene group in a 4 to 8 membered cycloalkyl ring may be replaced by an oxygen atom or by an alkylimino group, or $R_{22}$ denotes a $C_{9-12}$-benzocycloalkyl group or an aryl group, or F denotes a sulpho, phosphono, O-alkylphosphono, O,O'-dialkylphosphono, tetrazol-5-yl or $R_{23}CO$—O—$CHR_{24}$—O—CO group, wherein $R_{23}$ denotes a $C_{1-8}$-alkyl or $C_{1-8}$-alkoxy group, a cycloalkyl or cycloalkyloxy group each having 5 to 7 atoms in the cycloalkyl moiety, or an aryl, aryloxy, arylalkyl or arylalkoxy group and $R_{24}$ denotes a hydrogen atom or an alkyl group, and the shortest distance between the group F and the nitrogen atom of group A—B which is furthest from the group F is at least 11 bonds;

a third of the groups $R_a$ to $R_d$ denotes a hydrogen atom, an alkyl, perfluoroalkyl, alkoxy, alkylsulphenyl, alkylsulphinyl, alkylsulphonyl, amino, alkylamino, dialkylamino, aryl, heteroaryl or arylalkyl group; and the fourth of the groups $R_a$ to $R_d$ denotes a hydrogen atom or an alkyl or aryl group;

whilst unless otherwise specified each of the aryl moieties mentioned in the definition of the above groups is a phenyl group which may be monosubstituted by $R_{25}$, mono, di or trisubstituted by $R_{26}$, or monosubstituted by $R_{25}$ and additionally mono or disubstituted by $R_{26}$, wherein the substituents may be identical or different and $R_{25}$ denotes a cyano, carboxy, aminocarbonyl, alkylaminocarbonyl, dialkylaminocarbonyl alkoxycarbonyl, alkylcarbonyl, alkylsulphenyl, alkylsulphinyl, alkylsulphonyl, alkylsulphonyloxy, perfluoroalkyl, perfluoroalkoxy, nitro, amino, alkylamino, dialkylamino, alkylcarbonylamino, phenylalkylcarbonylamino, phenylcarbonylamino, alkylsulphonylamino, phenylalkylsulphonylamino, phenylsulphonylamino, N-alkylalkylcarbonylamino, N-alkylphenylalkylcarbonylamino, N-alkylphenylcarbonylamino, N-alkylalkylsulphonylamino, N-alkylphenylalkylsulphonylamino, N-alkylphenylsulphonylamino, aminosulphonyl, alkylaminosulphonyl or dialkylaminosulphonyl group, and $R_{26}$ denotes an alkyl, hydroxy or alkoxy group or a fluorine, chlorine, bromine or iodine atom, and if two $R_{26}$ groups are bound to adjacent carbon atoms they may also represent a $C_{3-6}$-alkylene group, a 1,3 butadien-1,4-diylene group or a methylenedioxy group, and each of the arylene moieties mentioned in the definition of the above-mentioned groups is a phenylene group which may be monosubstituted by $R_{25}$, mono or disubstituted by $R_{26}$, or monosubstituted by $R_{25}$ and additionally monosubstituted by $R_{26}$, wherein the substituents may be identical or different and are defined as hereinbefore, and each of the heteroaryl moieties mentioned in the definition of the above groups is a 5 membered heteroaromatic ring which contains an oxygen, sulphur or nitrogen atom, or a nitrogen atom and an oxygen, sulphur or nitrogen atom, or two nitrogen atoms and an oxygen, sulphur or nitrogen atom, or is a 6 membered heteroaromatic ring which contains 1, 2 or 3 nitrogen atoms and wherein additionally one or two —CH=N— groups may each be replaced by a —CO—$NR_{20}$— group (wherein $R_{20}$ is defined as hereinbefore), and additionally the above-mentioned heteroaromatic rings may be substituted by one or two alkyl groups or, on the carbon skeleton, by a fluorine, chlorine, bromine or iodine atom or by a hydroxy or alkoxy group, and unless otherwise specified, the above-mentioned alkyl, alkylene and alkoxy moieties may each contain 1 to 4 carbon atoms, and each carbon atom in the above mentioned alkylene and cycloalkylene moieties is linked to one heteroatom at most and the tautomers, stereoisomers and salts thereof.

Preferred compounds of the above general formula I, however, are those wherein:

X denotes a carbimino group optionally substituted at the nitrogen atom by an alkyl or cyano group, or X denotes a carbonyl, thiocarbonyl or sulphonyl group;

Y represents a straight chain $C_{2-3}$-alkylene group which is optionally substituted by $R_c$ or $R_d$, or by $R_c$ and $R_d$, and which may additionally be substituted by 1 or 2 alkyl groups and wherein additionally a methylene group may be replaced by a carbonyl group, or a straight chain $C_{2-3}$-alkenylene group which is optionally substituted by $R_c$ or $R_d$, or by $R_c$ and $R_d$, and in which additionally any methylene group present may be replaced by a carbonyl group, or a 1,2-cycloalkylene group with 5 to 7 carbon atoms optionally substituted by $R_c$ or $R_d$, or by $R_c$ and $R_d$, or a 1,2-cycloalkenylene group with 5 to 7 carbon atoms, or a 1,2-arylene group, or a 1,2-phenylene group, wherein 1 or 2 methine groups are each replaced by a nitrogen atom, wherein the above-mentioned heterocyclic groups may additionally be substituted by 1 or 2 alkyl groups, or a —CO—NH—, —NH—CO—, —CH=N— or —N=CH— group optionally substituted by $R_c$ or $R_d$;

a first of the groups $R_a$ to $R_d$ denotes an A—B group wherein

A is a group of one of the formulae

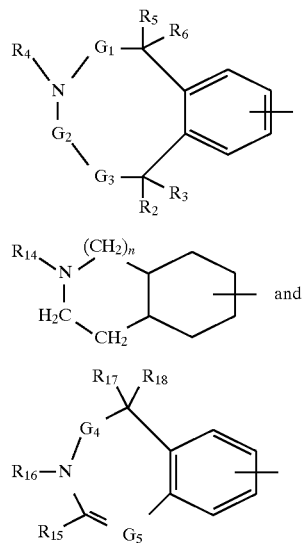

wherein the benzo moiety of the above-mentioned groups may be monosubstituted by $R_{25}$, or mono- or di-substituted by $R_{26}$, or mono-substituted by $R_{26}$, wherein the substituents $R_{25}$ and $R_{26}$, which may be identical or different, are defined as follows, and additionally in the above-mentioned benzo moiety, one to three methine groups may each be replaced a nitrogen atom or a —CH=CH group may be replaced by a —CO—$NR_1$ group, or a methine group may be replaced by a nitrogen atom and a —CH=CH group by a —CO—$NR_1$ group, wherein $R_1$ denotes a hydrogen atom or an alkyl group, $G_1$ and $G_4$ each represent a bond or a methylene group which may be mono or disubstituted by an alkyl or aryl group, wherein the substituents may be identical or different, $G_2$ denotes a bond or a methylene group substituted by $R_7$ and $R_8$, $G_3$ denotes a bond or a methylene group substituted by $R_9$ and $R_{10}$, $G_5$ denotes a nitrogen atom or a methine group optionally substituted by an alkyl or aryl group, $R_2$ denotes a hydrogen atom or an alkyl, aryl or a heteroaryl group or, if at least one of $G_2$ and $G_3$ does not represent a bond, $R_2$ may also denote a hydroxy or alkoxy group, $R_3$ denotes a hydrogen atom or an alkyl or aryl group, $R_4$ and $R_{14}$ each denote a hydrogen atom, a cycloalkyl or cycloalkylalkyl group each having 3 to 7 carbon atoms in the cycloalkyl moiety, a $C_{1-6}$-alkyl group, a $C_{3-6}$-alkenyl group (which alkenyl group may not be linked to the nitrogen atom via the vinyl moiety), a hydroxyalkyl, alkoxyalkyl, carboxyalkyl, alkoxycarbonylalkyl, aminocarbonylalkyl, N-alkylaminocarbonylalkyl, N,N-dialkylaminocarbonylalkyl, arylalkyl, alkoxycarbonyl, arylmethyloxycarbonyl, formyl, acetyl, trifluoroacetyl, allyloxycarbonyl, amidino or $R_{11}CO$—O—$(R_{12}CR_{13})$—O—CO— group, wherein $R_{11}$ denotes a $C_{1-8}$-alkyl group, a $C_{5-7}$-cycloalkyl group or an aryl or arylalkyl group, $R_{12}$ denotes a hydrogen atom, an alkyl group, a $C_{5-7}$-cycloalkyl group or an aryl group. and $R_{13}$ denotes a hydrogen atom, or $R_4$ together with $R_3$ may denote a straight chain $C_{2-4}$-alkylene group or, if $G_2$ does not represent a bond, a methylene group, $R_5$ denotes a hydrogen atom, an alkyl or aryl group or, if $G_1$ does not represent a bond, a hydroxy or alkoxy group or, if $G_1$ does represent a bond, $R_4$ together with $R_5$ may represent another bond, and $R_6$ denotes a hydrogen atom or an alkyl or aryl group or, if $G_1$ denotes a bond and $R_4$ together with $R_5$ denotes another bond, $R_6$ may denote a chlorine atom or a hydroxy, methoxy, amino, alkylamino or dialkylamino group, $R_7$ denotes a hydrogen atom or an alkyl or aryl group, $R_8$ denotes a hydrogen atom or an alkyl or aryl group or $R_8$ together with $R_4$ may denote a straight chain $C_{2-5}$-alkylene group, $R_9$ denotes a hydrogen atom or an alkyl or aryl group or, if $G_2$ does not represent a bond, $R_9$ may denote a hydroxy or alkoxy group, $R_{10}$ denotes a hydrogen atom or an alkyl or aryl group, or $R_{10}$ together with $R_4$ may denote a straight chain $C_{2-4}$-alkylene group, $R_{15}$ denotes a hydrogen or chlorine atom or an alkyl, aryl, hydroxy, methoxy, amino, alkylamino or dialkylamino group, $R_{16}$ denotes a hydrogen atom, a cycloalkyl or cycloalkyalkyl group each having 3 to 7 carbon atoms in the cycloalkyl moiety, a $C_{1-6}$-alkyl group, a $C_{3-6}$-alkenyl group (which alkenyl group may not be connected to the nitrogen atom via the vinyl group), or a hydroxyalkyl, alkoxyalkyl, carboxyalkyl, alkoxycarbonylalkyl, aminocarbonylalkyl, N-alkylaminocarbonylalkyl, N,N-dialkylaminocarbonylalkyl or arylalkyl group, $R_{17}$ represents a hydrogen atom or an alkyl group or, if $G_4$ denotes a bond, $R_{16}$ together with $R_{17}$ may denote another bond, $R_{18}$ denotes a hydrogen atom or an alkyl group or, if $G_4$ represents a bond and $R_{16}$ and $R_{17}$ together represent another bond, $R_{18}$ may denote a fluorine, chlorine or bromine atom or a hydroxy, methoxy, amino, alkylamino or dialkylamino group, and n represents the number 1 or 2, and B denotes a bond or an alkylene or arylene group, or a pyridinylene, pyrimidinylene, pyrazinylene, or pyridazinylene group, wherein one or two —CH=N— groups may each be replaced by a —CO—NH— group, whilst the above-mentioned heterocyclic groups may additionally be substituted by one or two alkyl groups, or a $C_{4-7}$-cycloalkylene group optionally substituted by one or two alkyl groups, or a $C_{5-7}$-cycloalkylene group which is optionally substituted by one or two alkyl groups, and in which a >CH unit is replaced by a nitrogen atom, whilst additionally, in the above-mentioned 5 to 7 membered rings, a methylene group adjacent to a nitrogen atom may be replaced by a carbonyl group;

a second of the groups $R_a$ to $R_d$ denotes a group of the formula

F—E—D— wherein

D denotes a $C_{1-6}$-alkylene group wherein a methylene group may be replaced by an oxygen or sulphur atom or by a sulphinyl, sulphonyl or $NR_{19}$ group, or wherein an ethylene group may be replaced by a —CO—$NR_{20}$ or —$NR_{20}$—CO group, (wherein $R_{19}$ denotes a hydrogen atom or an alkyl, alkylcarbonyl, alkylsulphonyl, arylcarbonyl or arylsulphonyl group, and $R_{20}$ denotes a hydrogen atom or an alkyl group), or a $C_{2-6}$ alkenylene or arylene group, or a pyridinylene, pyrimidinylene, pyrazinylene or pyridazinylene group wherein one or two —CH=N— groups may each be replaced by a —CO—NH— group, whilst the above-mentioned heterocyclic groups may additionally be substituted by one or two alkyl groups, or an indanylene, naphthylene, 1,2,3,4-tetrahydronaphthylene or benzosuberanylene group in which one of the rings is bound to the group E and the other ring is bound to the cyclic group of general formula I, whilst the saturated rings may each be substituted by one or two alkyl groups and the aromatic rings may each be substituted by a fluorine, chlorine, bromine or iodine atom or by an alkyl, trifluoromethyl, hydroxy, alkoxy, alkylsulphenyl, alkylsulphinyl, alkylsuphonyl or cyano group, or a $C_{4-7}$-cycloalkylene group optionally substituted by one or two alkyl groups, or a $C_{5-7}$-cycloalkylene group which is optionally substituted by one or two alkyl groups and in which a >CH unit is replaced by a nitrogen atom, whilst moreover in the above-mentioned 5 to 7 membered rings a methylene group adjacent to a nitrogen atom may be replaced by a carbonyl group, or a piperazinylene group which is optionally substituted by one or two alkyl groups, and in which a methylene group adjacent to a nitrogen atom may be replaced by a carbonyl group, or, if E represents a cyclic imino group, D may also denote an alkylenecarbonyl group having a total of 2 to 6 carbon atoms, the carbonyl group being bound to the nitrogen atom of the cyclic imino group of group E, or, if E does not represent a bond, D may also represent a bond, E denotes a bond, or a $C_{1-6}$-alkylene group which may be substituted by 1 or 2 $C_{1-6}$-alkyl groups, by a hydroxy, amino or aryl group, by an alkoxy or alkylamino group each having 1 to 6 carbon atoms, by a dialkylamino group having a total of 2 to 8 carbon atoms or by an $HNR_{21}$ or N-alkyl-$NR_{21}$— group (wherein $R_{21}$ denotes an alkylcarbonyl or alkylsulphonyl group each having 1 to 6 carbon atoms in the alkyl. moiety, a alkyloxycarbonyl group having a total of 2 to 5 carbon atoms, a cycloalkylcarbonyl or cycloalkylsulphonyl group each having 5 to 7 carbon atoms in the cycloalkyl moiety, an arylalkylcarbonyl, arylalkylsulphonyl, arylalkoxycarbonyl, arylcarbonyl or arylsulphonyl group), or a $C_{2-6}$-alkenylene group, or an arylene group, or a pyridinylene, pyrimidinylene, pyrazinylene or pyridazinylene group optionally substituted by one or two alkyl groups.

or a $C_{5-7}$-cycloalkylene group which is optionally substituted by one or two alkyl groups and in which a >CH unit is replaced by a nitrogen atom linked to a carbon atom of the group D, or a cycloalkylene group having 4 to 7 carbon atoms in the cycloalkylene moiety, optionally substituted by one or two $C_{1-6}$-alkyl groups, by a hydroxy, amino or aryl group, by a $C_{1-6}$-alkoxy or $C_{1-6}$-alkylamino group, by a dialkylamino group having a total of 2 to 8 carbon atoms or by an $HNR_{21}$ or N-alkyl-$NR_{21}$— group (wherein $R_{19}$ is hereinbefore defined), or, if D does not represent a bond, E may denote an alkylene group linked to group D via a group W, wherein W represents an oxygen or sulphur atom, a sulphinyl, sulphonyl, —$NR_{19}$—, —$NR_{20}$—CO— or —CO—$NR_2$— group, wherein $R_{19}$ and $R_{20}$ are as hereinbefore defined and the alkylene group may additionally be substituted by one or two $C_{1-6}$-alkyl groups, by a hydroxy, amino or aryl group, by an alkoxy or alkylamino group each having 1 to 6 carbon atoms, by a dialkylamino group having a total of 2 to 8 carbon atoms or by an $HNR_{21}$ or N-alkyl-$NR_{21}$— group, wherein the heteroatom of the additional substituent is separated from a heteroatom of group W by at least two carbon atoms and $R_{21}$ is as herein before defined, and F denotes a carbonyl group subsituted by a hydroxy group, by a $C_{1-6}$-alkoxy group, by an arylalkoxy group or by an $R_{22}O$ group (wherein $R_{22}$ denotes a $C_{4-7}$-cycloalkyl group or a cycloalkylalkyl group having 3 to 7 carbon atoms in the cycloalkyl moiety, wherein the cycloalkyl group may be substituted by an alkyl, alkoxy or dialkylamino group or by an alkyl group and by 1 to 3 methyl groups and additionally a methylene group in a 5 to 7 membered cycloalkyl ring m ay be replaced by an oxygen atom or by an alkylimino group, or $R_{22}$ denotes a $C_{9-11}$-benzocycloalkyl group), or a phosphono, O-alkylphosphono, O,O'-dialkylphosphono, tetrazol-5-yl or $R_{23}$CO—O—CHR$_{24}$—O—CO group, wherein $R_{23}$ denotes an alkyl or alkoxy group each having 1 to 8 carbon atoms, a cycloalkyl or cycloalkyloxy group each having 5 to 7 atoms in the cycloalkyl moiety or an aryl, aryloxy, arylalkyl or arylalkoxy group and $R_{24}$ denotes a hydrogen atom or an alkyl group, and the shortest distance between the group F and the nitrogen atom of group A—B which is furthest from the group F is at least 11 bonds;

a third of the groups $R_a$ to $R_d$ denotes a hydrogen atom, an alkoxy group (which alkoxy group cannot be bound to a nitrogen atom) an alkyl, trifluoromethyl, aryl, arylalkyl, thienyl, thiazolyl, pyridyl, pyrimidyl, pyrazinyl or pyridazinyl group; and a fourth of the groups $R_a$ to $R_d$ denotes a hydrogen atom or an alkyl group;

whilst unless otherwise specified each of the aryl moieties mentioned in the definition of the above groups is a phenyl group which may be monosubstituted by $R_{25}$, mono, di or trisubstituted by $R_{26}$, or monosubstituted by $R_{25}$ and additionally mono or disubstituted by $R_{26}$, wherein the substituents may be identical or different, and $R_{25}$ denotes a cyano, aminocarbonyl, alkylaminocarbonyl, dialkylaminocarbonyl, alkylcarbonyl, alkylsulphenyl, alkylsulphinyl, alkylsulphonyl or trifluoromethyl group and $R_{26}$ denotes an alkyl, hydroxy or alkoxy group or a fluorine, chlorine, or bromine atom, whilst if two $R_{26}$ groups are bound to adjacent carbon atoms they may also represent a $C_{3-6}$-alkylene group, a 1,3 butadien-1,4-diylene group or a methylenedioxy group, and each of the arylene moieties mentioned in the definition of the above-mentioned groups is a phenylene group which may be monosubstituted by $R_{25}$, or mono or disubstituted by $R_{26}$, or monosubstituted by $R_{25}$ and additionally monosubstituted by $R_{26}$, wherein the substituents may be identical or different and are defined as hereinbefore;

and unless otherwise specified, the above-mentioned alkyl, alkylene or alkoxy moieties may each contain 1 to 4 carbon atoms, and each carbon atom in the above mentioned alkylene and cycloalkylene moieties is linked to one heteroatom at most;

and the tautomers, stereoisomers and salts thereof.

Particularly preferred are those compounds of general formula I wherein,

X denotes a carbimino group substituted at the nitrogen atom by a cyano group, or X denotes a carbonyl or sulphonyl group, Y denotes a $CH_2CH_2$—, $CH_2CH_2CH_2$—, —CH=CH, —$CH_2CO$— or —$COCH_2$— group optionally substituted by $R_c$ or by $R_c$ and $R_d$, or a —CO—NH—, —NH—CO—, CH=N—, or —N=CH group optionally substituted by $R_c$ or $R_d$;

a first of the groups $R_a$ to $R_d$ denote an A—B group wherein

A is a group of one of the formulae

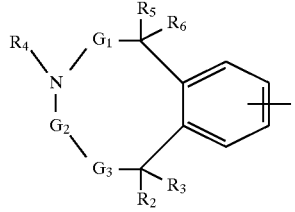

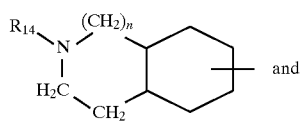

and

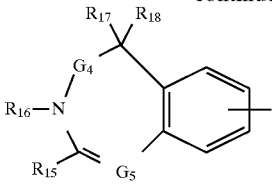

-continued wherein the benzo moiety of the above-mentioned groups may be substituted by a fluorine, chlorine or bromine atom or by an alkyl, cyano, trifluoromethyl, hydroxy, alkoxy group, or 1 to 3 methine groups may each be replaced by a nitrogen atom, $G_1$ denotes a bond or a methylene group which may be mono or disubstituted by an alkyl group, whilst the substituents may be identical or different, $G_2$ denotes a bond or a methylene group substituted by $R_7$ and $R_8$, $G_3$ denotes a methylene group substituted by $R_9$ and $R_{10}$, $G_4$ denotes a bond, $G_5$ denotes a nitrogen atom or a methine group optionally substituted by an alkyl group, $R_2$ denotes a hydrogen atom or an alkyl group, $R_3$ denotes a hydrogen atom or an alkyl group, $R_4$ denotes a hydrogen atom, a cycloalkyl or cycloalkylalkyl group each having 3 to 7 carbon atoms in the cycloalkyl moiety, a $C_{1-6}$-alkyl group, a $C_{3-6}$-alkenyl group (which alkenyl group may not be linked to the nitrogen atom via the vinyl group), or a hydroxyalkyl, alkoxyalkyl, carboxyalkyl, alkoxycarbonylalkyl, aminocarbonylalkyl, N-alkylaminocarbonylalkyl, N,N-di-alkylaminocarbonylalkyl, arylalkyl, alkoxycarbonyl, arylmethyloxycarbonyl, formyl, acetyl, trifluoroacetyl or $R_{11}CO$—O—$(R_{12}CR_{13})$—O—CO— group, (wherein $R_{11}$ denotes an alkyl group, $R_{12}$ denotes a hydrogen atom or an alkyl group, and $R_{13}$ denotes a hydrogen atom), or $R_4$ together with $R_3$ may denote a straight chain $C_{2-3}$-alkylene group, $R_5$ denotes a hydrogen atom or an alkyl group or, if $G_1$ denotes a bond, $R_4$ together with $R_5$ may denote another bond, $R_6$ denotes a hydrogen atom or an alkyl group or, if $G_1$ denotes a bond and $R_4$ together with $R_5$ denotes another bond, $R_6$ may denote an amino group, $R_7$ denotes a hydrogen atom or an alkyl group, $R_8$ denotes a hydrogen atom or an alkyl group, or $R_8$ together with $R_4$ may denote a straight chain $C_{3-4}$-alkylene group, $R_9$ denotes a hydrogen atom or an alkyl group, $R_{10}$ denotes a hydrogen atom or an alkyl group or $R_{10}$ together with $R_4$ may denote a straight chain $C_{3-4}$-alkylene group, $R_{14}$ denotes a hydrogen atom or an alkyl group, $R_{15}$ denotes a hydrogen atom or an alkyl group, $R_{16}$ denotes a hydrogen atom or an alkyl group, $R_{17}$ denotes a hydrogen atom or an alkyl group or $R_{16}$ together with $R_{17}$ may denote another bond, $R_{18}$ denotes hydrogen atom or an alkyl group or, if $R_{16}$ and $R_{17}$ together denote another bond, $R_{18}$ may denote a chlorine atom or an amino group, n represents the number 1 or 2, and B denotes a bond, or an alkylene group, or an arylene group, or a pyridinylene, pyrimidinylene, pyrazinylene, or pyridazinylene group, optionally substituted by 1 or 2 alkyl groups, or a cylcohexylene group optionally substituted by 1 or 2 alkyl groups, or a piperidinylene group which is optionally substituted by 1 or 2 alkyl groups, and in which a methylene group adjacent to a nitrogen atom may be replaced by a carbonyl group;

a second of the groups $R_a$ to $R_d$ denotes a group of formula

F—E—D— wherein

D denotes an alkylene group, or an arylene group, or a pyridinylene, pyrimidinylene, pyrazinylene or pyridazinylene group optionally substituted by 1 or 2 alkyl groups, or an indanylene, naphthylene, 1,2,3,4-tetrahydronaphthylene or benzosuberanylene group, wherein one of the rings is bound to the group E and the other ring to the cyclic group of general formula I, or a $C_{4-7}$-cycloalkylene group optionally substituted by 1 or 2 alkyl groups, or a $C_{5-7}$-cycloalkylene group which is optionally substituted by 1 or 2 alkyl group and in which a >CH unit is replaced by a nitrogen atom, whilst additionally in the above-mentioned 5 to 7 membered rings a methylene group adjacent to a nitrogen atom may be replaced by a carbonyl group, or, if E denotes a cyclic imino group, D may denote an alkylenecarbonyl group, wherein the carbonyl group is bound to the nitrogen atom of the cyclic imino group of group E, or if E does not represent a bond, D may also denote a bond, E denotes a bond, or an alkylene group which may be substituted by a $C_{1-6}$-alkyl group or by an amino, aryl, alkylamino, dialkylamino, $HNR_{21}$ or N-alkyl-$NR_{21}$-group (wherein $R_{21}$ denotes an alkylcarbonyl or alkylsuphonyl group each having 1 to 6 carbon atoms in the alkyl moiety, an alkyloxycarbonyl group having a total of 2 to 5 carbon atoms, a cycloalkylcarbonyl or cycloalkylsulphonyl group each having 5 to 7 carbon atoms in the cycloalkyl moiety, or an arylalkylcarbonyl, arylalkylsulphonyl, arylalkoxycarbonyl, arylcarbonyl or arylsulphonyl group), or a $C_{2-4}$-alkenylene group, or an arylene group, or a pyridinylene, pyrimidinylene, pyrazinylene or pyridazinylene group optionally substituted by one or two alkyl groups, or a $C_{5-7}$-cycloalkylene group which is optionally substituted by one or two alkyl groups and in which a >CH unit is replaced by a nitrogen atom linked to a carbon atom of the group D, or a $C_{4-7}$-cycloalkylene group optionally substituted by one or two alkyl groups, or, if D does not represent a bond, E may also denote an alkylene group linked to a group D via a group W, wherein W denotes a n oxygen or sulphur atom or a sulphinyl, sulphonyl, —$NR_{20}$—CO— or —CO—$NR_{20}$— group, wherein $R_{20}$ denotes a hydrogen atom or an alkyl group and the alkylene group may additionally be substituted by a $c_{1-6}$-alkyl group, or by an amino, aryl, alkylamino, dialkylamino, $HNR_{21}$ or N-alkyl-$NR_{21}$—group, wherein the heteroatom of the additional substituent is seperated from a heteroatom of group W by at least two carbon atoms and $R_{21}$ is as hereinbefore defined, and F denotes a carbonyl group substituted by a hydroxy, alkoxy, arylalkoxy or $R_{20}O$ group (wherein $R_{22}$ denotes a $C_{5-7}$-cycloalkyl group or a cycloalkylalkyl group having 5 to 7 carbon atoms in the cycloalkyl moiety), or an $R_{23}CO$—O—$CHR_{24}$—O—CO—, phosphono or O-alkylphosphono group, wherein $R_{23}$ denotes an alkyl, alkoxy, cycloalkyl or cycloalkyloxy group each having 5 to 7 carbon atoms in the cycloalkyl moiety and $R_{24}$ denotes a hydrogen atom or an alkyl group, and the shortest distance between the group F and the nitrogen atom of group A—B which is furthest from the group F is at least 11 bonds;

a third of the groups $R_a$ to $R_d$ denotes a hydrogen atom, an alkoxy group (which alkoxy group may not be bound to a nitrogen atom), or an alkyl, trifluoromethyl or aryl group; and the fourth of the groups $R_a$ to $R_d$ denotes a hydrogen atom or an alkyl group, whilst unless otherwise specified each of the aryl moieties mentioned in the definition of the above groups is a phenyl group which may be monosubstituted by $R_{25}$, mono, di or trisubstituted by $R_{26}$, or monosubstituted by $R_{25}$ and additionally mono or disubstituted by $R_{26}$, wherein the substituents may be identical or different and $R_{25}$ denotes a cyano, aminocarbonyl, alkylaminocarbonyl, dialkylaminocarbonyl, alkylcarbonyl, alkylsulphenyl, alkylsulphinyl, alkylsulphonyl or trifluoromethyl group and $R_{26}$ denotes an alkyl, hydroxy or alkoxy group or a fluorine, chlorine or bromine atom, whilst two groups $R_{26}$, if they are bound to adjacent carbon atoms, may also represent a straight chain $C_{3-4}$-alkylene group, a 1,3-butadien-1,4-diylene group or a methylenedioxy group, and each of the arylene moieties mentioned in the definition of the above-mentioned groups is a phenylene group which may be monosubstituted by $R_{25}$, mono or disubstituted by $R_{26}$, or monosubstituted by $R_{25}$ and additionally monosubstituted by $R_{26}$, wherein the substituents may be identical or different and are defined as hereinbefore, and unless otherwise specified, the above-mentioned alkyl, alkylene or alkoxy moieties may each contain 1 to 4 carbon atoms, and each carbon atom in the above mentioned alkylene and cycloalkylene moieties is linked to one heteroatom at most;

and the tautomers, stereoisomers and salts thereof.

Particularly preferred compounds of general formula I are those wherein:

X denotes a carbonyl or sulphonyl group;

Y denotes a $CH_2CH_2$, $CH_2CH_2CH_2$, CH═CH, $CH_2CO$ or $COCH_2$ group optionally substituted by one or two methyl groups, or a CO—NH, CH═N or N═CH group optionally substituted by $R_c$;

a first of the groups $R_a$ to $R_c$ denotes an A—B— group wherein

A denotes a group of one of the formulae

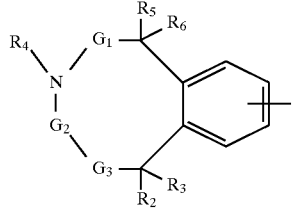

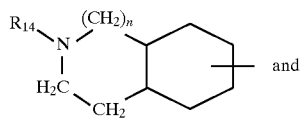

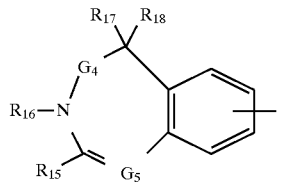

wherein in the benzo moiety of the above-mentioned groups one or two methine groups may each be replaced by a nitrogen atom, $G_1$ denotes a bond or a methylene group, $G_2$ denotes a bond, $G_3$ denotes a methylene group., $G_4$ denotes a bond, $G_5$ denotes a nitrogen atom or a methine group, $R_2$ denotes a hydrogen atom, $R_3$ denotes a hydrogen atom, $R_4$ denotes a hydrogen atom, a cyclopropyl or cyclopropylmethyl group, a $C_{1-6}$-alkyl group, or an allyl, hydroxyalkyl, carboxyalkyl, alkoxycarbonylalkyl or benzyl group, $R_5$ denotes a hydrogen atom, $R_6$ denotes a hydrogen atom, $R_{14}$ denotes a hydrogen atom or an alkyl group, $R_{15}$ denotes a hydrogen atom or an alkyl group, $R_{16}$ denotes a hydrogen atom or an alkyl group, $R_{17}$ denotes a hydrogen atom or $R_{16}$ together with $R_{17}$ may denote another bond, $R_{18}$ denotes a hydrogen atom or, if $R_{16}$ and $R_{17}$ together denote another bond, $R_{18}$ may denote an amino group, n represents the number 1 or 2, and B denotes a bond or a phenylene group;

a second of the groups $R_a$ to $R_c$ denotes a group of formula

F—E—D— wherein

D denotes an alkylene group, or a phenylene group, or a cyclohexylene group, or a piperidinylene group, wherein the ring nitrogen atom is linked to an optionally substituted straight chain alkylene group of group E, or a bond, E denotes a straight chain alkylene group which may be substituted by an alkyl or phenyl group, or a $C_{2-4}$-alkenylene group, or a phenylene group, or, if D does not represent a bond, E may denote a straight chain O-alkylene group linked to group D via the oxygen atom, and F denotes a carbonyl group substituted by a hydroxy or alkoxy group, and the shortest distance between the group F and the nitrogen atom of group A—B— which is furthest from the group F is at least 11 bonds, and the third of the groups $R_a$ to $R_c$ denotes a hydrogen atom, an alkoxy group (which alkoxy group may not be bound to a nitrogen atom), or an alkyl or phenyl group;

whilst unless otherwise specified the above mentioned alkyl, alkylene or alkoxy moieties may each contain 1 to 4 carbon atoms and each carbon atom in the above mentioned alkylene and cycloalkylene moieties is linked to 1 heteroatom at most;

and the tautomers, stereoisomers and salts thereof.

Most particularly preferred compounds of general formula I are those wherein

X denotes a carbonyl group,

Y denotes a $CH_2CH_2$, $CH_2CH_2CH_2$, CH═CH, $CH_2CO$ or $COCH_2$ group, or an optionally methyl-substituted N═CH group;

the group $R_a$ denotes an A—B group wherein

A denotes a group of one of the formulae

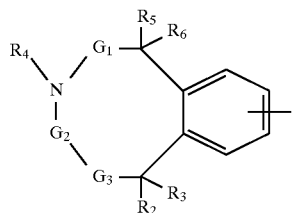

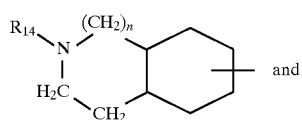

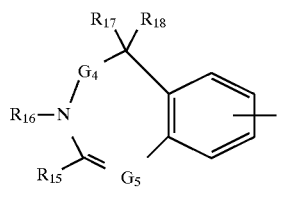

wherein in the benzo moiety of the above-mentioned groups one or two methine groups may each be replaced by a nitrogen atom, $G_1$ denotes a bond or a methylene group, $G_2$ denotes a bond, $G_3$ denotes a methylene group, $G_4$ denotes a bond, $G_5$ denotes a methine group, $R_2$ denotes a hydrogen atom, $R_3$ denotes a hydrogen atom, $R_4$ denotes a hydrogen atom, a $C_{1-4}$-alkyl group, or an allyl or benzyl group, $R_5$ denotes a hydrogen atom, $R_6$ denotes a hydrogen atom,
$R_{14}$ denotes a hydrogen atom or a methyl group,
$R_{15}$ denotes a hydrogen atom,
$R_{16}$ together with $R_{17}$ denotes a bond,
$R_{18}$ denotes a hydrogen atom or an amino group, and n represents the number 1, B denotes a bond;

the group $R_b$ denotes a group of the formula

F—E—D— wherein

D denotes a $CH_2CH_2$ group,
or a 1,4-phenylene group, or
or a 1,4-cyclohexylene group, E denotes an optionally methyl-substituted $CH_2CH_2$ group, a CH=CH, 1,4-phenylene or O—$CH_2$— group, wherein the oxygen atom of the O—$CH_2$— group is linked to the group D, and F denotes a carbonyl group substituted by a hydroxy or $C_{1-4}$-alkoxy group;

and the shortest distance between the group F and the nitrogen atom of group A—B— which is furthest from group F is at least 11 bonds;

and the tautomers, the stereoisomers and the salts thereof.

The following are mentioned as examples of particularly preferred compounds:

(a) 1-[4-[2-(methoxycarbonyl)ethyl]phenyl]-3-(1,2,3,4-tetrahydroisoquinolin-6-yl)-imidazolidin-2-one,
(b) 1-[4-(2-carboxyethyl)phenyl]-3-(1,2,3,4-tetrahydroisoquinolin-6-yl)-imidazolidin-2-one,
(c) 1-[4-(2-carboxyethyl)phenyl]-3-(2-methyl-1,2,3,4-tetrahydroisoquinolin-6-yl)-imidazolidin-2-one,
(d) 1-[4-[2-(isobutyloxycarbonyl)ethyl]phenyl]-3-(1,2,3,4-tetrahydroisoquinolin-6-yl)-imidazolidin-2-one,
(e) 1-[4-(2-carboxyethyl)phenyl]-3-(2,3,4,5-tetrahydro-1H-3-benzazepin-7-yl)-imidazolidin-2-one,
(f) 1-[4-[2-(methoxycarbonyl)ethyl]phenyl]-3-(2,3,4,5-tetrahydro-1H-3-benzazepin-7-yl)-imidazolidin-2-one,
(g) 1-[4-[2-(isopropyloxycarbonyl)ethyl]phenyl]-3-(2,3,4,5-tetrahydro-1H-3-benzazepin-7-yl)-imidazolidin-2-one,
(h) 1-[4-(2-carboxyethyl)phenyl]-3-(3-methyl-2,3,4,5-tetrahydro-1H-3-benzazepin-7-yl)-imidazolidin-2-one,
(i) 4-[4-[2-(carboxyethyl)phenyl]-5-methyl-2-(2,3,4,5-tetrahydro-1H-3-benzazepin-7-yl)-4H-1,2,4-triazol-3-one,
(j) 1-[trans-4-(2-carboxyethyl)cyclohexyl]-3-(2,3,4,5-tetrahydro-1H-3-benzazepin-7-yl)-imidazolidin-2-one,
(k) 1-[4-[2-(methoxycarbonyl)ethyl]phenyl]-3-(3-methyl-2,3,4,5-tetrahydro-1H-3-benzazepin-7-yl)-imidazolidin-2-one,
(l) 1-[4-[2-(ethoxycarbonyl)ethyl]phenyl]-3-(3-methyl-2,3,4,5-tetrahydro-1H-3-benzazepin-7-yl)-imidazolidin-2-one,
(m) 1-[4-[2-(isopropyloxycarbonyl)ethyl]phenyl]-3-(3-methyl-2,3,4,5-tetrahydro-1H-3-benzazepin-7-yl)-imidazolidin-2-one,
(n) 1-[trans-4-(2-carboxyethyl)cyclohexyl]-3-(3-methyl-2,3,4,5-tetrahydro-1H-3-benzazepin-7-yl)-imidazolidin-2-one,
(o) 1-[trans-4-[2-(isopropyloxycarbonyl)ethyl]cyclohexyl]-3-3-methyl-2,3,4,5-tetrahydro-1H-3-benzazepin-7-yl)-imidazolidine-2-one,
(p) 1-[trans-4-[2-(ethoxycarbonyl)ethyl]cyclohexyl]-3-(3-methyl-2,3,4,5-tetrahydro-1H-3-benzazepin-7-yl)-imidazolidin-2-one,
(q) 1-[trans-4-[2-(methoxycarbonyl)ethyl]cyclohexyl]-3-(3-methyl-2,3,4,5-tetrahydro-1H-3-benzazepin-7-yl)-imidazolidin-2-one,
(r) 1-[trans-4-[(carboxymethyl)oxy]cyclohexyl]-3-(3-methyl-2,3,4,5-tetrahydro-1H-3-benzazepin-7-yl)-imidazolidin-2-one,
(s) 3-[trans-4-(2-carboxyethyl)cyclohexyl]-1-(3-methyl-2,3,4,5-tetrahydro-1H-3-benzazepin-7-yl)-hydantoin and
(t) 1-[trans-4-(2-carboxyethyl)cyclohexyl]-3-(3-ethyl-2,3,4,5-tetrahydro-1H-3-benzazepin-7-yl)-imidazolidin-2-one, and the tautomers and the salts thereof.

According to the invention, the new compounds of general formula I may be obtained, for example, by the following methods:

a) to prepare compounds of general formula I wherein F denotes a carboxyl group:
conversion of a compound of general formula

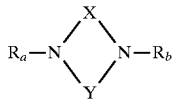

(II)

(wherein
$R_a$, $R_b$, X and Y are as hereinbefore defined, with the proviso that one of the groups $R_a$ to $R_d$ denotes an F'—E—D group, wherein E and D are as hereinbefore defined, and F' represents a group which can be converted into a carboxyl group by hydrolysis, treatment with acids, thermolysis or hydrogenolysis) into a compound of general formula I wherein F denotes a carboxyl group.

For example, functional derivatives of a carboxyl group such as unsubstituted or substituted amides, esters, thioesters, trimethylsilylesters, orthoesters, iminoesters, amidines or anhydrides, or nitrile groups may be converted by hydrolysis into a carboxyl group, esters with tertiary alcohols, e.g. tert.butylesters, may be converted by treatment with an acid or thermolysis into a carboxyl group and esters with aralkanols, e.g. benzylesters, may be converted by hydrogenolysis into a carboxyl group.

The hydrolysis is appropriately carried out either in the presence of an acid such as hydrochloric, sulphuric, phosphoric, trichloroacetic or trifluoroacetic acid, or mixtures thereof, in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane, at temperatures between −10° C. and 120° C., e.g. at temperatures between ambient temperature and the boiling temperature of the reaction mixture.

Under the reaction conditions mentioned hereinbefore, any N-acylamino or N-acylimino groups present such as an N-trifluoroacetylimino group may be converted into the corresponding amino or imino groups. Furthermore, any alcoholic hydroxy groups present during the treatment with an organic acid such as trichloroacetic acid or trifluoroacetic acid may simultaneously be converted into a corresponding acyloxy group such as a trifluoroacetoxy group.

If F' in a compound of formula II represents a cyano or aminocarbonyl group, these groups may also be converted into a carboxyl group with a nitrite, e.g. sodium nitrite, in the presence of an acid such as sulphuric acid, which may appropriately be used as the solvent at the same time, at temperatures between 0° and 50° C.

If F' in a compound of formula II represents a tert.butyloxycarbonyl group for example, the tert.butyl group may also be cleaved by treating with an acid such as trifluoroacetic acid, formic acid, p-toluenesulphonic acid, sulphuric acid, phosphoric acid or polyphosphoric acid, optionally in an inert solvent such as methylene chloride, chloroform, benzene, toluene, diethylether, tetrahydrofuran or dioxane, preferably at temperatures between −10° C. and 120° C., e.g. at temperatures between 0° and 60° C., or thermally, optionally in an inert solvent such as methylene chloride, chloroform, benzene, toluene, tetrahydrofuran or dioxane and preferably in the presence of a catalytic amount of an acid such as p-toluenesulphonic acid, sulphuric acid, phosphoric acid or polyphosphoric acid, preferably at the boiling temperature of the solvent used, e.g. at temperatures between 40° C. and 100° C. Under the reaction conditions mentioned hereinbefore, any N-tert.butyloxycarbonylamino or N-tert.butyloxycarbonylimino groups present may be converted into the corresponding amino or imino groups.

If F' in a compound of formula II represents a benzyloxycarbonyl group for example, the benzyl group may also be hydrogenolytically cleaved in the presence of a hydrogenation catalyst, such as palladium/charcoal in a suitable solvent such as methanol, ethanol, ethanol/water, glacial acetic acid, ethyl acetate, dioxane or dimethylformamide, preferably at temperatures between 0° and 50° C., e.g. at ambient temperature, under a hydrogen pressure of 1 to 5 bar. During hydrogenolysis, other groups may also be reduced at the same time, e.g. a nitro group may be reduced to an amino group or a benzyloxy group to a hydroxy group, and an N-benzylamino, N-benzylimino, N-benzyloxycarbonylamino or N-benzyloxycarbonylimino group may be converted into a corresponding amino or imino group.

b) In order to prepare compounds of general formula I wherein $R_{16}$ and $R_{17}$ together represent another bond, $G_4$ denotes a bond and at least one of the groups $R_{15}$ or $R_{18}$ denotes a hydroxy, methoxy, amino, alkylamino or dialkylamino group having 1 to 4 carbon atoms in the alkyl moiety:

reacting a compound of general formula

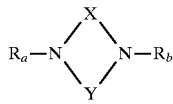
(III)

(wherein $R_a$, $R_b$, X and Y are hereinbefore defined, with the proviso that one of the groups $R_a$ to $R_d$ denotes an A—B group wherein B is defined as hereinbefore and A denotes a group of the formula

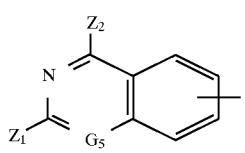

wherein the benzo moiety and $G_5$ are as hereinbefore defined, $Z_1$ and $Z_2$, which may be identical or different, each denote a nucleophilic leaving group such as a halogen atom, eg. a chlorine or bromine atom, but the group $Z_1$ may also have the meanings given for $R_{15}$ hereinbefore or the group $Z_2$ may have the meanings given for $R_{18}$ hereinbefore)

with a compound of general formula

(IV)

wherein $R_{27}$ denotes a hydroxy, methoxy, amino, formylamino, acetylamino, alkylamino or dialkylamino group having 1 to 4 carbon atoms in the alkyl moiety.

The reaction is expediently carried out in a solvent such as water, acetone, ethanol, tetrahydrofuran, dioxane, dimethylformamide or dimethylsulfoxide, but optionally in an excess of the compound of general formula IV used as solvent and optionally in the presence of a base such as sodium hydroxide, potassium hydroxide, potassium carbonate, sodium amide or sodium hydride at temperatures between 0° and 250° C., but preferably at temperatures between 50° and 225° C.

c) In order to prepare compounds of general formula I wherein $R_{16}$ and $R_{17}$ together denote another bond, $G_4$ denotes a bond and $R_{18}$ denotes a chlorine or bromine atom:

reacting a compound of general formula

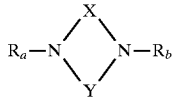
(V)

(wherein $R_a$, $R_b$, X and Y are as hereinbefore defined, with the proviso that one of the groups $R_a$ to $R_d$ represents an A—B group wherein B is as hereinbefore defined and A denotes a group of formula

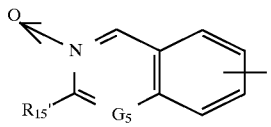

wherein the benzo moiety and $G_5$ are as hereinbefore defined and $R_{15}'$ denotes a hydrogen atom or represents the alkyl and aryl group s mentioned for $R_{15}$ hereinbefore) with an acid halide.

The reaction is carried out with an acid halide such as phosphorus oxychloride or phosphorus oxybromide, optionally in the presence of a solvent such as benzene, dichlorobenzene, nitrobenzene, or carbon tetrachloride, and optionally in the presence of a salt of a corresponding hydrohalic acid such as sodium chloride or sodium bromide at elevated temperatures, eg. at temperatures between 50° and 250° C., but preferably at the boiling temperature of the reaction mixture.

d) In order to prepare compounds of general formula I wherein X denotes a cyano-substituted carbimino group or a carbonyl or sulphonyl group and Y denotes a straight chain $C_{2-4}$-alkylene group optionally substituted by $R_c$ or $R_d$, or by $R_c$ and $R_d$:

cyclising a compound of general formula

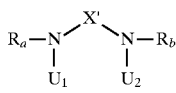
(VI)

wherein $R_a$ and $R_b$ are as hereinbefore defined, X, denotes a cyano-substituted carbimino group or a carbonyl sulphonyl or group, one of the groups $U_1$ or $U_2$ denotes a hydrogen atom and the other group $U_1$ or $U_2$ denotes a straight chain $C_{2-4}$-alkylene group optionally substituted by $R_c$ or $R_d$, or by $R_c$ and $R_d$, to which additionally a nucleophilic leaving group such as a halogen atom, a hydroxy or sulphonic acid ester group, eg. a chlorine, bromine or iodine atom or a hydroxy, methanesulfonyloxy or p-toluenesulfonyloxy group) is terminally bound.

The reaction is preferably carried out in a solvent such as methylene chloride, acetonitrile, tetrahydrofuran, toluene, dimethylformamide or dimethylsulfoxide, optionally in the presence of a base such as sodium hydride, potassium carbonate, potassium tert.butoxide or N-ethyl-diisopropylamine or optionally in the presence of a dehydrating agent such as triphenylphosphine/diethyl azodicarboxylate, at temperatures between −20° and 100° C., preferably at temperatures between 0° and 60° C.

e) In order to prepare compounds of general formula I wherein X denotes a carbonyl group and Y denotes one of the above mentioned alkylene or alkenylene groups:

reacting a compound of general formula $$R_{28}\text{—NH—T} \quad \text{(VII)}$$

with an isocyanate of general formula $$O\!=\!C\!=\!N\text{—}R_{29} \quad \text{(VIII)}$$

(wherein
one of the groups $R_{28}$ or $R_{29}$ has the meanings given for $R_a$ hereinbefore and
the other group $R_{28}$ or $R_{29}$ has the meanings given for $R_b$ hereinbefore and
T denotes a group of the formula $$\text{—}(CH_2)_m\text{—HC}(OR_{30})_2$$

optionally substituted in the alkylidene moiety by $R_c$ or $R_d$ or by $R_c$ and $R_d$, wherein
m denotes the number 1, 2 or 3 and
$R_{30}$ denotes a $C_{1-4}$-alkyl group)
optionally with subsequent hydrogenation.

The reaction is optionally carried out in an inert solvent such as dioxane or toluene at temperatures between 20° and 200° C., preferably between 20° and 160° C. However, the reaction can also be carried out without a solvent.

An open-chained urea optionally obtained as an intermediate product in the reaction of a compound of general formula VII with an isocyanate of general formula VIII is, if desired, subsequently converted into the desired compound in the presence of an acid such as acetic acid, trifluoroacetic acid, p-toluenesulphonic acid or hydrochloric acid, optionally in a solvent such as methanol, ethanol, tetrahydrofuran or methylene chloride at temperatures between 0° C. and the boiling temperature of the reaction mixture.

The optional subsequent hydrogenation is preferably carried out with hydrogen in the presence of catalyst such as palladium/charcoal or platinum, in a solvent such as methanol, ethanol, ethyl acetate or glacial acetic acid, optionally with the addition of an acid such as hydrochloric acid, at temperatures between 0° and 100° C., but preferably at temperatures between ambient temperature and 50° C., and under a hydrogen pressure of 1 to 7 bar, but preferably 3 to 5 bar.

f) In order to prepare compounds of general formula I wherein $G_1$ and $G_2$ each represent a bond, $G_3$ represents a methylene group optionally substituted by a $C_{1-4}$-alkyl group, $R_2$, $R_4$ and $R_5$ each represent a hydrogen atom, and $R_3$ and $R_6$, which may be identical or different, each represent a hydrogen atom or a $C_{1-4}$-alkyl group:

hydrogenation of a compound of general formula $$\text{(IX)}$$

$$R_a\text{—N}\diagup\overset{X}{\diagdown}\text{N—}R_b$$
$$\diagdown\underset{Y}{\diagup}$$

wherein
$R_a$, $R_b$, X and Y are as hereinbefore defined, with the proviso that one of the groups $R_a$ to $R_d$ denotes an A—B group, wherein
B is as hereinbefore defined and
A denotes a group of formula

[structure with $R_{18}'$, N, $R_{15}''$, $G_5'$ and benzo ring]

wherein,
the benzo moiety is as hereinbefore defined,
$G_5'$ denotes a methine group optionally substituted by a $C_{1-4}$-alkyl group,
$R_{15}''$ and $R_{18}'$, which may be identical or different, each represent a hydrogen atom or a $C_{1-4}$ alkyl group.

The hydrogenation is preferably carried out in a suitable solvent such as methanol, methanol/water, acetic acid, ethyl acetate, ethanol, ether, tetrahydrofuran, dioxane or dimethylformamide with hydrogen in the presence of a hydrogenation catalyst such as Raney nickel, platinum, platinum dioxide, rhodium or palladium/charcoal, optionally with the addition of an acid such as hydrochloric acid at temperatures between 0° and 100° C., preferably at temperatures between 20° and 80° C. Any optionally substituted alkenylene groups present in a compound of general formula IX may thereby be converted into optionally substituted alkylene groups.

g) In order to prepare compounds of general formula I wherein F denotes a carbonyl group substituted by a $C_{1-6}$-alkoxy group, by an arylalkoxy group (having 1 to 4 carbon atoms in the alkoxy moiety and wherein the aryl moiety is as hereinbefore defined), or by an $R_{22}O$ group:

reacting a compound of general formula $$\text{(X)}$$

$$R_a\text{—N}\diagup\overset{X}{\diagdown}\text{N—}R_b$$
$$\diagdown\underset{Y}{\diagup}$$

(wherein
$R_a$, $R_b$, X and Y are as hereinbefore defined, with the proviso that one of the groups $R_a$ to $R_d$ denotes an F''—E—D group, wherein
E and D are as hereinbefore defined and
F'' denotes a carboxy or alkoxycarbonyl group) with an alcohol of general formula $$\text{HO—}R_{31} \quad \text{(XI)}$$

wherein
$R_{31}$ has the meanings given for $R_{22}$ hereinbefore or denotes a $C_{1-6}$-alkyl group or an arylalkyl group in which the aryl moiety is as hereinbefore defined and the alkyl moiety may contain 1 to 4 carbon atoms.

The reaction of a carboxy compound is optionally carried out in a solvent or mixture of solvents such as methylene chloride, dimethylformamide, benzene, toluene, chlorobenzene, tetrahydrofuran, benzene/tetrahydrofuran or dioxane or, particularly advantageously, in a corresponding alcohol of general formula XI, optionally in the presence of an acid such as hydrochloric acid or in the presence of a dehydrating agent, eg. in the presence of isobutyl-chloroformate, tetraethyl orthocarbonate, trimethyl-orthoacetate, 2,2-dimethoxypropane, tetramethoxysilane, thionylchloride, trimethylchlorosilane, sulphuric acid, methanesulphonic acid, p-toluenesulfonic acid, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxybenzotriazole, N,N'-carbonyldiimidazole or triphenylphosphine/carbon tetrachloride, and optionally with the addition of a base such as pyridine, 4-dimethylaminopyridine or triethylamine, expediently at temperatures between 0° and 150° C., preferably at temperatures between 0° and 100° C.

The reaction of a corresponding alkoxycarbonyl compound with an alcohol of general formula XI is preferably carried out in a corresponding alcohol as solvent, optionally in the presence of a further solvent such as methylene chloride or ether, preferably in the presence of an acid such as hydrocholoric acid at temperatures between 0° and 150° C., preferably at temperatures between 50° and 100° C.

h) In order to prepare compounds of general formula I wherein one of the groups $R_4$, $R_{14}$ or $R_{16}$ represents one of the optionally substituted alkyl, alkenyl, cycloalkyl, cycloalkylalkyl or aralkyl groups mentioned hereinbefore in the definition of groups $R_4$, $R_{14}$ or $R_{16}$:

reacting a compound of general formula

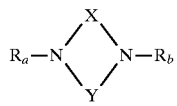

(XII)

(wherein $R_a$, $R_b$, X and Y are as hereinbefore defined, with the proviso that one of the groups $R_a$ to $R_d$ denotes an A—B group, wherein A and B are as hereinbefore defined, with the proviso that $R_4$, $R_{14}$ and $R_{16}$ each represent a hydrogen atom) with a compound of general formula $$Z_3-R_{32}$$ (XIII)

wherein $R_{32}$ denotes a $C_{1-8}$-alkyl group, a cycloalkyl or cycloalkylalkyl group in which the cycloalkyl moiety may contain 3 to 7 carbon atoms and the alkyl moiety may contain 1 to 4 carbon atoms, a $C_{3-8}$-alkenyl group, or an arylalkyl, hydroxyalkyl, alkoxyalkyl, cyanoalkyl, carboxyalkyl, alkoxycarbonylalkyl, aminocarbonylalkyl, N-alkylaminocarbonylalkyl or N,N-dialkylaminocarbonyl group, wherein the aryl moiety and the alkyl moieties are as hereinbefore defined, and $Z_3$ denotes a nucleophilic leaving group such as a halogen atom, eg. a chlorine, bromine, or iodine atom, or a sulphonic acid ester group, eg. a methanesulphonyloxy or p-toluenesulfonyloxy group, or $Z_3$ together with an adjacent hydrogen atom of the group $R_{32}$ denotes an oxygen atom.

The alkylation with a compound of formula XIII wherin $Z_3$ denotes a nucleophilic leaving group is expediently carried out in a solvent such as methylene chloride, tetrahydrofuran, dioxane, dimethylsulfoxide or dimethylformamide, optionally in the presence of a base such as sodium carbonate, potassium carbonate or sodium hydroxide solution or in the presence of a tertiary organic base such as N-ethyl-diisopropylamine or N-methyl-morpholine, which may simultaneously be used as solvents, at temperatures between −30° and 150° C., but preferably at temperatures between 20° and 120° C.

The reductive alkylation with a carbonyl compound of general formula XIII is carried in the presence of a complex metal hydride such as sodium borohydride, lithium borohydride or sodium cyanoborohydride, expediently at a pH from 6–7 and at ambient temperature or in the presence of a hydrogenation catalyst, eg. with hydrogen in the presence of palladium/charcoal, under a hydrogen pressure of 1–5 bar. However, methylation is preferably carried out in the presence of formic acid as reducing agent at elevated temperatures, eg. at temperatures between 60° and 120° C.

i) In order to prepare compounds of general formula I wherein X represents a carbimino group which is substituted by a cyano group at the nitrogen atom, or X represents a carbonyl or sulphonyl group:

reacting a compound of general formula

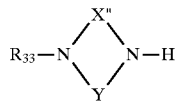

(XIV)

with a compound of general formula $$Z_4-R_{34}$$ (XV)

(wherein

Y is as hereinbefore defined,

X" denotes a carbimino group substituted by a cyano group at the nitrogen atom, or X" denotes a carbonyl or sulphonyl group, one of the groups $R_{33}$ or $R_{34}$ has the meanings given for $R_a$ hereinbefore and the other group $R_{33}$ or $R_{34}$ has the meanings given for $R_b$ hereinbefore and $Z_4$ denotes a nucleophilic leaving group such as a halogen atom, a hydroxy or sulphonic acid ester group, eg. a fluorine, chlorine, bromine or iodine atom or a methanesulphonyloxy or p-tolunesulfonyloxy group).

The reaction is preferably carried out in a solvent such as methylene chloride, acetonitrile, tetrahydrofuran, toluene, pyridine, dimethylformamide, dimethylsulfoxide or N-methylpyrrolidone, optionally in the presence of one or more bases such as sodium hydride, potassium carbonate, potassium tert.butoxide, N-ethyldiisopropylamine, tris-[2-(2-methoxyethoxy)ethyl]amine or N,N,N',N'-tetramethylethylenediamine and optionally in the presence of a dehydrating agent such as triphenyl-phosphine/diethyl azodicarboxylate and optionally in the presence of copper powder or one or more copper salts such as copper(I) iodide as reaction accelerators, at temperatures between −20° and 250° C., but preferably at temperatures between 0° and 60° C., if $Z_4$ is bound to an aliphatic carbon atom, or at temperatures between 60° and 180° C., if $Z_4$ is bound to an aromatic carbon atom, whilst in this case $Z_4$ can only represent a halogen atom.

j) In order to prepare compounds of general formula I wherein $R_4$ or $R_{14}$ denotes an alkoxycarbonyl, arylmethyloxycarbonyl, formyl, acetyl, trifluoroacetyl, allyloxycarbonyl or $R_{11}CO—O—(R_{12}CR_{13})—O—CO$ group, wherein $R_{11}$ to $R_{13}$ and the aryl moiety are as hereinbefore defined and the alkoxy moiety may contain 1 to 4 carbon atoms:

reacting a compound of general formula

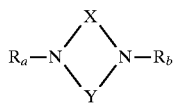

(wherein

R$_a$, R$_b$, and Y are as hereinbefore defined, with the proviso that R$_4$ or R$_{14}$ denotes a hydrogen atom)

with a compound of general formula

 (XVII)

wherein

R$_{35}$ represents an alkoxycarbonyl group having a total of 2 to 5 carbon atoms, an arylmethyloxycarbonyl group in which the aryl moiety is as hereinbefore defined, or a formyl, acetyl, allyoxycarbonyl, R$_{11}$CO—O—(R$_{12}$CR$_{13}$)—O—CO or trifluoroacetyl group, wherein R$_{11}$ to R$_{13}$ are as hereinbefore defined, and Z$_5$ denotes a nucleophilic leaving group such as a halogen atom, or an aryloxy, arylthio, alkoxy, alkoxycarbonyloxy, aralkoxycarbonyloxy or N-imidazolyl group, eg. a chlorine or bromine atom or a 4-nitrophenoxy group.

The acylation is expediently carried out in a solvent such as tetrahydrofuran, methylene chloride, chloroform, dimethylformamide, water or mixtures of these solvents, optionally in the presence of a base such as sodium carbonate, potassium carbonate or sodium hydroxide solution or in the presence of a tertiary organic base such as triethylamine, N-ethyl-diisopropylamine, N-methylmorpholine or pyridine, which may simultaneouly serve as solvents, at temperatures between −30° and 100° C., but preferably at temperatures between −10° and 60° C.

k) In order to prepare compounds of general formula I wherein F denotes a carbonyl group which is substituted by a C$_{1-6}$-alkoxy group, by an arylalkoxy group (in which the aryl moiety is defined as hereinbefore and the alkoxy moiety may contain 1 to 4 carbon atoms), or by an R$_{22}$O or R$_{23}$CO—O—CHR$_{24}$O group, wherein R$_{22}$ to R$_{24}$ are as hereinbefore defined: p1 reacting a compound of general formula

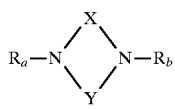 (XVIII)

(wherein

R$_a$, R$_b$, X and Y are as hereinbefore defined, with the proviso that one of the groups R$_a$ to R$_d$ denotes an F'''—E—D— group wherein E and D are as hereinbefore defined and F''' denotes a carboxyl group)

with a compound of general formula

 (XIX)

wherein

R$_{36}$ represents a C$_{1-6}$-alkyl group, an arylalkyl group (in which the aryl moiety is defined as hereinbefore and the alkyl moiety may contain 1 to 4 carbon atoms), or R$_{22}$- or R$_{23}$CO—O—CHR$_{24}$— group (wherein R$_{22}$ to R$_{24}$ are as hereinbefore defined), and Z$_6$ denotes a nucleophilic leaving group such as a halogen atom or a sulphonic acid ester group, eg. a chlorine or bromine atom or a methanesulphonyloxy or p-toluenesulphonyloxy group.

The reaction is preferably carried out in a solvent such as methylene chloride, tetrahydrofuran, dioxane, dimethylsulfoxide or dimethylformamide, optionally in the presence of a reaction accelerator such as sodium or potassium iodide and preferably in the presence of a base such as sodium carbonate, potassium carbonate or sodium hydroxide solution or in the presence of a tertiary organic base such as N-ethyl-diisopropylamine or N-methylmorpholine, which may simultaneously serve as solvents, or optionally in the presence of silver carbonate or silver oxide, at temperatures between −30° and 100° C., but preferably at temperatures between −10° and 80° C.

l) In order to prepare compounds of general formula I wherein X denotes a carbonyl group and Y denotes a straight chain C$_{2-4}$-alkylene group which is optionally substituted by R$_c$ or R$_d$, or by R$_c$ and R$_d$ and in which a methylene group in the terminal position is replaced by a carbonyl group:

cyclising a compound of general formula

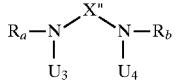 (XX)

(wherein

R$_a$ and R$_b$ are as hereinbefore defined,

X'' denotes a carbonyl group, one of the groups U$_3$ or U$_4$ represents a hydrogen atom and the other group U$_3$ or U$_4$ represents a straight chain C$_{2-4}$-alkylene group which is optionally substituted by R$_c$ or R$_d$, or by R$_c$ and R$_d$, and in which a terminal methylene group is replaced by a Z$_7$—CO group, wherein Z$_7$ represents a nucleophilic leaving group such as a halogen atom or a hydroxy, alkoxy, aryloxy or arylalkoxy group, eg. a chlorine or bromine atom or a hydroxy, methoxy, ethoxy, phenoxy or benzyloxy group), optionally formed in the reaction mixture.

The reaction is preferably carried out in a solvent such as methylene chloride, acetonitrile, tetrahydrofuran, toluene, dimethylformamide or dimethylsulfoxide, optionally in the presence of a base such as sodium hydride, potassium carbonate, potassium tert.butoxide or N-ethyl diisopropylamine or optionally in the presence of a dehydrating agent such as triphenylphosphine/diethyl azodicarboxylate or N,N'-carbonyldiimidazole, at temperatures between −20° and 200° C., preferably at temperatures between 0° and 160° C.

If according to the invention a compound of general formula I is obtained which contains an unsaturated carbon-carbon bond, this may be converted by catalytic hydrogenation into a corresponding saturated compound of general formula I.

The catalytic hydrogenation is preferably carried out with hydrogen in the presence of a catalyst such as palladium/charcoal, in a solvent such as methanol, ethanol, ethyl acetate or glacial acetic acid, optionally with the addition of an acid such as hydrochloric acid at temperatures between 0° and 100° C., but preferably at temperatures between 20° and 60° C., and under a hydrogen pressure of 1 to 7 bar, but preferably 3 to 5 bar.

In the reactions described hereinbefore, any reactive groups present such as hydroxy, carboxy, phosphono, amidino, O-alkylphosphono, amino, alkylamino, imino or amidino groups may be protected during the reaction by means of conventional protecting groups which are cleaved again after the reaction.

For example, the protecting group for a hydroxy group may be a trimethylsilyl, acetyl, benzoyl, tert.butyl, trityl, benzyl or tetrahydropyranyl group, the protecting group for a carboxyl group may be a trimethylsilyl, methyl, ethyl, tert.butyl, benzyl or tetrahydropyranyl group, the protecting group for a phosphono group may be an alkyl group such as a methyl, ethyl, isopropyl or n-butyl, phenyl or benzyl group, the protecting group for an optionally alkyl substituted amidino group may be a benzyloxycarbonyl group and the protecting group for an amino, alkylamino or imino group may be a formyl, acetyl, trifluoroacetyl, ethoxycarbonyl, tert.-butoxycarbonyl, benzyloxycarbonyl, benzyl, methoxybenzyl or 2,4-dimethoxy benzyl group, and for an imino group a methyl group is also possible and for an amino group a phthalyl group may also be considered.

The optional subsequent cleaving of a protecting group may, for example, be carried out hydrolytically in an aqueous solvent, e.g. in water, isopropanol/water, acetic acid/water, tetrahydrofuran/water or dioxane/water, in the presence of an acid such as trifluoroacetic acid, hydrochloric acid, or sulphuric acid or in the presence of an alkali metal base such as sodium hydroxide or potassium hydroxide, or by ether cleavage, e.g. in the presence of iodotrimethylsilane, at temperatures between 0° and 120° C., preferably at temperatures between 10° and 100° C.

However, a benzyl, methoxybenzyl or benzyloxycarbonyl group may be cleaved hydrogenolytically, for example, using hydrogen in the presence of a catalyst such as palladium/charcoal, in a solvent such as methanol, ethanol, ethyl acetate or glacial acetic acid, optionally with the addition of an acid such as hydrochloric acid, at temperatures between 0° and 100° C., but preferably between 20° and 60° C., under a hydrogen pressure of 1 to 7 bar, preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic or hydrochloric acid, or by treating with iodotrimethylsilane, optionally using a solvent such as methylene chloride, dioxane, methanol or ether.

A trifluoroacetyl group is preferably cleaved by treating with an acid such as hydrochloric acid, optionally in the presence of a solvent such as acetic acid or methanol, at temperatures between 50° and 120° C. or by treating with sodium hydroxide solution, optionally in the presence of a solvent such as tetrahydrofuran or methanol, at temperatures between 0° and 50° C.

The cleaving of a methyl group from a methylimino group is preferably carried out in the presence of 1-chloroalkylchloroformates such as 1-chloroethyl chloroformate, preferably in the presence of a base such as 1,8-bis-(dimethylamino)-naphthalene in the presence of a solvent such as methylene chloride, 1,2-dichloroethane, toluene or dioxane, at temperatures between 0° and 150° C., preferably at temperatures between 20° C. and the boiling temperature of the reaction mixture, and subsequently treating with an alcohol such as methanol, at temperatures between 20° C. and the boiling temperature of the alcohol used.

A phthalyl group is preferably cleaved in the presence of hydrazine or a primary amine such as methylamine, ethylamine or n-butylamine, in a solvent such as methanol, ethanol, isopropanol, toluene/water or dioxane, at temperatures between 20° and 50° C.

The cleaving of only one alkyl group from an O,O'-dialkylphosphono group is preferably carried out using sodium iodide, in a solvent such as acetone, ethylmethylketone, acetonitrile or dimethylformamide, at temperatures between 40° and 150° C., but preferably at temperatures between 60° and 100° C.

The cleaving of both alkyl groups from an O,O'-dialkylphosphono group is carried out, for example, with iodotrimethylsilane, bromotrimethylsilane or chlorotrimethylsilane/sodium iodide in a solvent such as methylene chloride, chloroform or acetonitrile, at temperatures between 0° C. and the boiling temperature of the reaction mixture, but preferably at temperatures between 20° and 60° C.

Furthermore, the compounds of general formula I obtained may be resolved into their enantiomers and/or diastereomers as mentioned hereinbefore. Thus, for example, cis/trans mixtures may be resolved into their cis and trans isomers, and compounds having at least one optically active carbon atom may be resolved into their enantiomers.

Thus, for example, the cis/trans mixtures obtained may be resolved by chromatography into the cis and trans isomers thereof and the compounds of general formula I which occur in racemate form may be separated by methods known per se (see. Allinger N. L. and Eliel E. L. in "Topics in Stereochemistry", Vol. 6, Wiley Interscience, 1971) into their optical antipodes and compounds of general formula I having at least 2 asymmetric carbon atoms may be separated on the basis of their physical-chemical differences using known methods, e.g. by chromatography and/or fractional crystallisation, into the diastereomers thereof which, if they occur in racemic form, may subsequently be separated into the enantiomers as mentioned above.

The separation of enantiomers is preferably effected by column separation on chiral phases or by recrystallisation from an optically active solvent or by reacting with an optically active substance, especially an acid or an activated derivative thereof or an alcohol, which forms salts or derivatives such as esters or amides with the racemic compound, and separation of the diastereomeric salt mixture or derivative thus obtained, e.g. on the basis of their different solubilities, whilst the free antipodes may be released from the pure diastereomeric salts by the action of suitable agents. Particularly common, optically active acids include, for example, the D- and L-forms of tartaric and dibenzoyltartaric acid, di-o-tolyl-tartaric acid, malic acid, mandelic acid, camphorsulphonic acid, glutamic acid, aspartic acid or quinic acid. Examples of an optically active alcohol include (+) or (−)-menthol and examples of an optically active acyl group in amides include (+) or (−)-menthyloxycarbonyl.

Moreover, the compounds of formula I obtained may be converted into the salts thereof, particularly for pharmaceutical use into the physiologically acceptable salts thereof with inorganic or organic acids. Examples of suitable acids include hydrochloric acid, hydrobromic acid, sulphuric acid, phosphoric acid, fumaric acid, succinic acid, lactic acid, citric acid, tartaric acid or maleic acid.

In addition, the new compound s of formula I thus obtained, if they contain a carboxyl, sulpho, phosphono, O-alkyl-phosphono or tetrazol-5-yl group, may subsequently, if desired, be converted into the addition salts thereof with inorganic or organic bases, more particularly for pharmaceutical use, into the physiologically acceptable addition salts thereof. Examples of suitable bases include sodium hydroxide, potassium hydroxide, arginine, cyclohexylamine, ethanolamine, diethanolamine and triethanolamine.

The compounds used as starting materials are known from the literature in some cases or may be obtained by methods known from the literature (see the Examples).

Thus, for example, "The Organic chemistry of Heterocyclic Compounds", volume 37, by C. Temple Jr., published by John Wiley & Sons, 1981, describes in Chapters 13, 14 and 19 the preparation of corresponding triazole compounds.

In Houben-Weyl, "Methoden der Organischen Chemie", volume E4, by H. Hagemann, Georg Thieme Verlag, 1983, there is a description on page 368 onwards of the preparation of corresponding cyclic urea compounds. Also, in the same volume, pages 355 onwards, there is a description by way of example of the preparation of corresponding open-chained urea compounds possibly needed as starting compounds.

Thus, for example, a corresponding cyclic urea derivative is obtained by cyclising a correspondingly substituted urea (which is in turn obtained by reacting a corresponding amine with a corresponding isocyanate), or by reacting a correspondingly substituted diamine with a carbonic acid derivative such as phosgene, or a corresponding triazolone derivative is obtained by cyclising a corresponding semicarbazide, which is in turn obtained by reacting a corresponding isocyanate with a corresponding hydrazide.

In the cyclic urea derivatives thus obtained, a carbonyl group can subsequently, if desired, be converted into a corresponding thiocarbonyl or carbimino group using known methods.

In the resulting cyclic starting compounds or in the starting compounds required to prepare them, any ester group present can be converted by hydrolysis into a carboxyl group or any carboxyl group present can be converted into an ester group.

As already mentioned, the new cyclic derivatives of general formula I and the addition salts thereof, particularly the physiologically acceptable addition salts thereof with inorganic or organic acids or bases, have valuable properties. Thus, the compounds of general formula I have valuable pharmacological properties and in addition to having an inhibitory effect on inflammation and bone degradation, have, in particular, antithrombotic, antiaggregatory and tumour- or metastasis-inhibiting effects.

By way of example, the compounds of general formula I were investigated for their biological effects as follows:
1. Inhibition of the binding of $^3$H-BIBU 52 to Human thrombocytes A suspension of human thrombocytes in plasma is incubated with $^3$H-BIBU 52[=(3S,5S)-5-[(4'-amidino-4-biphenylyl)oxymethyl]-3-[(carboxy)methyl]-2-pyrrolidinone[3-$^3$H-4-biphenylyl]], which replaces the ligand $^{125}$I-fibrinogen known from the literature (see German Patent Application P 42 14 245.8 by the same applicant dated Apr. 30, 1992, internal reference number: Case 5/1093-FL) and various concentrations of the test substance. The free and bound ligand are separated by centrifuging and quantitatively measured by scintillation counting. From the measurements obtained the inhibition of $^3$H-BIBU 52 binding caused by the test substance is determined.

In order to do this, donor blood is taken from an anticubital vein and anti-coagulated with trisodium citrate (final concentration 13 mM). The blood is centrifuged for 10 minutes at 170×g and the supernatant platelet-rich plasma (PRP) is removed. The remaining blood is centrifuged vigorously once more in order to recover plasma. The PRP is diluted with autologous plasma 1:10. 750 µl are incubated for 20 minutes at ambient temperature with 50 µl of physiological saline solution, 100 µl of test substance solution, 50 µl of $^{14}$C-sucrose (3700 Bq) and 50 µl of $^3$H-BIBU 52 (final concentration: 5 nM). In order to measure the non specific binding, 5 µl of BIBU 52 (final concentration 30 µM) are used instead of the test substance. The samples are centrifuged for 20 seconds at 10000×g and the supernatant is drawn off. 100 µl thereof are measured in order to determine the free ligand. The pellet is dissolved in 500 µl of 0.2N NaOH, 450 µl are mixed with 2 ml of scintallator and 25 µl of 5N HCl, and measured. The residual plasma remaining in the pellet is determined from the $^{14}$C-content, and the bound ligand is determined from the $^3$H-measurement. After substracting the non specific binding, the pellet activity is plotted against the concentration of the test substance and the concentration for 50% inhibition of binding is determined.

2. Antithrombotic activity

Method

Thrombocyte aggregation is measured using the Born and Cross method (J. Physiol. 170: 397 (1964)) in platelet-rich plasma taken from healthy volunteers. To inhibit coagulation the blood is mixed with 3.14% sodium citrate in a ratio by volume of 1:10.

Collagen-induced aggregation

The pattern of the decrease in optical density of the platelet suspension is photometrically measured and recorded after the addition of the aggregation-triggering substance. The rate of aggregation is determined from the angle of inclination of the density curve. The point on the curve where there is maximum light transmittance is used to calculate the optical density.

The amount of collagen used is as small as possible but sufficient to produce an irreversible reaction curve. Standard commercial collagen produced by Hormonchemie of Munich is used.

Before the addition of the collagen the plasma is incubated for 10 minutes with the test substance at 37° C.

From the measurements obtained, an $EC_{50}$ is determined graphically, indicating a 50% change in the optical density in terms of the inhibition of aggregation.

The Table which follows contains the results found:

| Substance (Example No.) | $^3$H-BIBU 52-binding test $IC_{50}$[nM] | Inhibition of platelet aggregation $EC_{50}$[nM] |
| --- | --- | --- |
| 1 | 190 | >10000 |
| 2(1) | 5400 | >10000 |
| 2(2) | 24 | 40 |
| 6 | 110 | 40 |
| 8(1) | 36 | 150 |
| 9 | 85 | 190 |
| 9(1) | 760 | 990 |
| 19 | 59 | 230 |
| 19(1) | 120 | 350 |
| 19(3) | 81 | 430 |

Moreover, the compounds of Examples 7 and 19, for example, inhibit the collagen-induced thrombocyte aggregation ex vivo in Rhesus monkeys for more than 5 and more than 8 hours, respectively, after oral administration of 1 mg/kg.

The compounds according to the invention are well tolerated because after intravenous administration of 30 mg/kg of the compounds of Examples (8)1 and 19 to three mice, none of the three test animals died.

In the light of their inhibitory effect on cell-cell and cell-matrix interactions, the new cyclic urea derivatives of general formula I and the physiologically acceptable addition salts thereof are suitable for combating or preventing diseases in which smaller or greater cell aggregates occur or in which cell-matrix interactions play a part, e.g. in treating or preventing venous and arterial thrombosis, cerebrovascular diseases, lung embolism, cardiac infarction, arteriosclerosis, osteoporosis and the metastasis of tumours and the treatment of genetically caused or acquired disorders of cell interactions with one another or with solid structures. They are also suitable for parallel therapy in thrombolysis with fibrinolytics or vascular interventions such as transluminal angioplasty or in the treatment of shock, psoriasis, diabetes and inflammation.

For treating or preventing the diseases mentioned above the dosage is between 0.1 µg and 30 mg/kg of body weight, preferably 1 µg to 15 mg/kg of body weight, given in up to 4 doses per day. For this purpose the compounds of formula I produced according to the invention, optionally in conjunction with other active substances such as thromboxane receptor antagonists and thromboxane synthesis inhibitors or combinations thereof, serotonin antagonists, α-receptor antagonists, alkylnitrates such as glycerol trinitrate, phosphodiesterase inhibitors, prostacyclin and the analogues thereof, fibrinolytics such as tPA, prourokinase, urokinase, streptokinase, or anticoagulants such as heparin, dermatan sulphate, activated protein C, vitamin K antagonists, hirudine, inhibitors of thrombin or other activated clotting factors, may be incorporated together with one or more inert conventional carriers and/or diluents, e.g. corn starch, lactose, sucrose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearylalcohol, carboxymethylcellulose or fatty substances such as hard fat or suitable mixtures thereof, into conventional galenic preparations such as plain or coated tablets, capsules, powders, suspensions, solutions, sprays or suppositories.

The Examples which follow are intended to illustrate the invention:

EXAMPLE I 1-(Isoquinolin-N-oxide-6-yl)-3-[4-[2-(methoxycarbonyl)ethyl]-phenyl]-imidazolidin-2-one 2.6 g of 1-(isoquinolin-6-yl)-3-[4-[2-(methoxycarbonyl)ethyl]-phenyl]-imidazolidin-2-one are dissolved in 175 ml of methylene chloride with heating. The mixture is cooled in an ice bath and mixed with 1.46 g of 3-chloroperoxybenzoic acid (90% strength). After 24 hours stirring at 0° C. the mixture is diluted with methylene chloride and extracted twice with sodium hydrogen carbonate and sodium thiosulphate solution and then with water. The organic phase is separated off, dried and evaporated down.

Yield: 2.4 g (88% of theory), $R_f$ value: 0.15 (silica gel; methylene chloride/methanol/ethyl acetate=20:1:1)

EXAMPLE II

N-(2-Hydroxyethyl)-N'-(isoquinolin-6-yl)-N-[4-[2-(methoxycarbonyl)ethyl]phenyl]-urea To 7.2 g of imidazole and 10.1 g of N,N'-carbonyldiimidazole in 100 ml of dimethylformamide are added dropwise, at a temperature of 0° to 10° C., 9.0 g of 6-aminoisoquinoline in 70 ml of dimethylformamide. After 2 hours stirring at ambient temperature, 15.3 g of N-(2-hydroxyethyl)-4-[2-(methoxycarbonyl)ethyl]-aniline in 20 ml of dimethylformamide are added dropwise and the mixture is stirred for 2½ days at ambient temperature. The mixture is diluted with 750 ml of ethyl acetate and extracted twice with water and saturated saline solution. The organic phase is separated off, dried and evaporated down. The residue is purified by chromatography over a silica gel column using ethyl acetate/methylene chloride/methanol= 70:30:10.

Yield: 4.8 g (19% of theory), $R_f$ value: 0.48 (silica gel; methylene chloride/methanol/ethyl acetate=20:1:1)

The following compounds are obtained analogously to Example II:

(1) N-(2,2-diethoxyethyl)-N'-(isoquinolin-6-yl)-N-[4-[2-(methoxycarbonyl)ethyl]phenyl]-urea $R_f$ value: 0.50 (silica gel; methylene chloride/methanol= 20:1)

(2) N-(3-ethyl-2,3,4,5-tetrahydro-1H-3-benzazepin-7-yl)-N'-(2,2-diethoxyethyl)-N'-[trans-4-[2-(methoxy-carbonyl)ethyl]-cyclohexyl]-urea Melting point: 101°–104° C.

$R_f$ value: 0.63 (silica gel; methylenechloride/methanol/conc. aqueous ammonia=90:10:2)

(3) N-(7-ethyl-6,7,8,9-tetrahydro-5H-pyrazino-[2,3-d]azepin-2-yl)-N'-(2,2-diethoxyethyl)-N'-[trans-4-[2-(methoxycarbonyl)-ethyl]cyclohexyl]-urea Carried out with 1,1'-carbonyl-di-(1,2,4-triazole)

Melting point: 100°–102° C.

$R_f$ value: 0.41 (silica gel; methylene chloride/methanol= 9:1)

| Calc.: | C 62.40 | H 8.73 | N 13.48 |
|---|---|---|---|
| Found: | 62.19 | 8.79 | 13.62 |

(4) N-(7-benzyl-6,7,8,9-tetrahydro-5H-pyrimido-[4,5-d]azepin-2-yl)-N'-(2,2-diethoxyethyl)-N'-[trans-4-[2-(methoxycarbonyl)-ethyl]cyclohexyl]-urea Carried out with 1,1'-carbonyl-di-(1,2,4-triazole)

$R_f$ value: 0.23 (Reversed Phase silica gel; methanol/5% aqueous saline solution=6:4)

EXAMPLE III

N-(3-tert.Butyloxycarbonyl-2,3,4,5-tetrahydro-1H-3-benzazepin-7-yl)-N-(2-hydroxyethyl)-N'-[4-[2-(methoxycarbonyl)ethyl]-phenyl]-urea 4.5 g of 3-(tert.butyloxycarbonyl)-7-[(2-hydroxyethyl)amino]-2,3,4,5-tetrahydro-1H-3-benzazepine and 3.7 g of 4-[2-(methoxycarbonyl)ethyl]-phenylisocyanate (prepared from the corresponding amine by reaction with phosgene) are stirred in 35 ml of dioxane for 3.5 hours at ambient temperature. The reaction mixture is evaporated down, the residue is triturated with tert.butylmethylether and suction filtered. The product is washed with tert.butyl-methylether and dried.

Yield: 6.3 g (76% of theory),

Melting point: 115°–117° C., $R_f$ value: 0.30 (silica gel; cyclohexane/ethyl acetate=1:1)

The following compounds are obtained analogouly to Example III:

(1) 1-acetyl-4-[4-[2-(methoxycarbonyl)ethyl]phenyl]-semicarbazide (Reaction of acetylhydrazine with 4-[2-(methoxycarbonyl)-ethyl]-phenylisocyanate)

Melting point: 159°–165° C.

R_f value: 0.37 (silica gel; methylene chloride/methanol= 9:1)
(2) N-(2-hydroxyethyl)-N-[trans-4-[2-(methoxycarbonyl)ethyl]-cyclohexyl]-N'-(3-trifluoroacetyl-2,3,4,5-tetrahydro-1H-3-benzazepin-7-yl)-urea Melting point: 150°–152° C.

R_f value: 0.31 (silica gel; cyclohexane/ethyl acetate=1:1)
(3) N-(2,2-diethoxyethyl)-N-(3-trifluoroacetyl-2,3,4,5-tetrahydro-1H-3-benzazepin-7-yl)-N'-[trans-4-[2-(methoxycarbonyl)-ethyl]-cyclohexyl]-urea The [trans-4-[2-(methoxycarbonyl)ethyl]cyclohexyl]-isocyanate used is obtained from the corresponding amine-hydrochloride by reaction with phosgene. The 7-[(2,2-diethoxyethyl)amino]-3-trifluoroacetyl-2,3,4,5-tetrahydro-1H-3-benzazepine used [R_f value: 0.76 (silica gel; cyclohexane/ethyl acetate=3:2)] is obtained by reacting 7-amino-3-trifluoroacetyl-2,3,4,5-tetrahydro-1H-3-benzazepine with bromoacetaldehyde-diethylacetal in the presence of N-ethyl-diisopropylamine.

R_f value: 0.26 (silica gel; cyclohexane/ethyl acetate=3:2)
(4) N-[trans-[[(methoxycarbonyl)methyl]oxy]cyclohexyl]-N'-(2,2-diethoxyethyl)-N'-(3-trifluoroacetyl-2,3,4,5-tetrahydro-1H-3-benzazepin-7-yl)-urea The [trans-4-[[(methoxycarbonyl)methyl]oxy]-cyclohexyl]-isocyanate used is obtained from the corresponding amine hydrochloride by reaction with phosgene.

R_f value: 0.20 (silica gel; cyclohexane/ethyl acetate=1:1)
(5) N-(2-hydroxyethyl)-N-[4-[trans-2-(methoxycarbonyl)-ethenyl]phenyl]-N'-(3-trifluoroacetyl-2,3,4,5-tetrahydro-1H-3-benzazepin-7-yl)-urea The (3-trifluoroacetyl-2,3,4,5-tetrahydro-1H-3-benzazepin-7-yl)-isocyanate used is obtained from the corresponding amine by reaction with phosgene.

Melting point: from 118° C.

R_f value: 0.18 (silica gel; cyclohexane/ethyl acetate=1:1)
(6) N-[4-(2-(ethoxycarbonyl)-1-propyl]phenyl]-N'-(2,2-diethoxyethyl)-N'-(3-trifluoroacetyl-2,3,4,5-tetrahydro-1H-3-benzazepin-7-yl)-urea The [4-[2-(ethoxycarbonyl)-1-propyl]phenyl]-isocyanate used is obtained by reacting the corresponding amine with phosgene.

R_f value: 0.35 (silica gel; cyclohexane/ethyl acetate=2:1)
(7) N-[trans-4-[2-(methoxycarbonyl)ethyl]cyclohexyl]-N'-[(benzyloxycarbonyl)methyl]-N'-(3-trifluoroacetyl-2,3,4,5-tetrahydro-1H-3-benzazepin-7-yl)-urea The 7-[[(benzyloxycarbonyl)methyl]amino]-3-trifluoroacetyl-2,3,4,5-tetrahydro-1H-3-benzazepine used [R_f value: 0.24 (silica gel; cyclohexane/ethyl acetate=4:1)] is obtained by reacting 7-amino-3-trifluoroacetyl-2,3,4,5-tetrahydro-1H-3-benzazepine with benzyl bromoacetate in the presence of N-ethyldiisopropylamine.

R_f value: 0.51 (silica gel; cyclohexane/ethyl acetate=1:1)
(8) N-(3-hydroxypropyl)-N-[trans-4-[2-(methoxycarbonyl)-ethyl]cyclohexyl]-N'-(3-trifluoroacetyl-2,3,4,5-tetrahydro-1H-3-benzazepin-7-yl)-urea Melting point: 129°–130° C.
(9) 1-acetyl-4-[trans-4-[2-(methoxycarbonyl)ethyl]-cyclohexyl]-semicarbazide Melting point: 176°–179° C.

R_f value: 0.24 (silica gel; methylene chloride/methanol= 95:5)
(10) 1-formyl-4-[trans-4-[2-(methoxycarbonyl)ethyl]-cyclohexyl]-semicarbazide Melting point: 169°–171° C.
(11) N-[4-[2-(ethoxycarbonyl)-1-phenyl-ethyl]phenyl]-N'-(2,2-diethoxyethyl)-N'-(3-trifluoroacetyl-2,3,4,5-tetrahydro-1H-3-benzazepin-7-yl)-urea The [4-[2-(ethoxycarbonyl)-1-phenyl-ethyl]phenyl]-isocyanate used is obtained from the corresponding amine by reacting with phosgene.

The crude product is used directly to prepared the compound of Example 5(6).
(12) 1-Formyl-4-(3-trifluoroacetyl-2,3,4,5-tetrahydro-1H-3-benzazepin-7-yl)-semicarbazide R_f value: 0.41 (silica gel; methylene chloride/methanol= 9:1)

EXAMPLE IV 3-(tert.Butyloxycarbonyl)-7-[(2-hydroxyethyl)amino]-2,3,4,5-tetrahydro-1H-3-benzazepine 7.2 g of 7-amino-3-(tert.butyloxycarbonyl)-2,3,4,5-tetrahydro-1H-3-benzazepine (prepared from 7-nitro-2,3,4,5-tetrahydro-1H-3-benzazepine by reacting with di-tert.butyl pyrocarbonate and subsequent hydrogenation in the presence of palladium on activated charcoal) in 130 ml of methanol is mixed with 1.53 ml of glacial acetic acid and 1.8 g of glycolaldehyde (dimer) with stirring. Then 1.9 g of sodium cyanoborohydride are added and the mixture is stirred for one hour at ambient temperature. The reaction mixture is evaporated down and the residue is divided between ethyl acetate and water. The organic phase is separated off, washed twice with water, dried and evaporated down. The residue is purified by chromatography over a silica gel column with cyclohexane/ethyl acetate (4:6).

Yield: 5.4 g (64% of theory),

Melting point: 86°–89° C.,

R_f value: 0.39 (silica gel; cyclohexane/ethyl acetate=4:6)

The following compound is obtained analogously to Example IV:
(1) methyl trans-4-[(2-hydroxyethyl)amino]-cinnamate Melting point: 117°–118° C.

R_f value; 0.25 (silica gel; cyclohexane/ethyl acetate=1:1)

EXAMPLE V (4aRS,6RS,8aRS)-6-[(2,2-Dimethoxyethyl)amino]-2-methyl-1,2,3,4,4a,5,6,7,8,8a-decahydroisoquinoline To a solution of 9.0 g of (4aRS,8aRS)-2-methyl-6-oxo-1,2,3,4,4a,5,6,7,8,8a-decahydroisoquinoline and 6.8 g of aminoacetaldehyde-dimethylacetal in 90 ml of acetonitrile are added 31 ml of 3N hydrochloric acid and the mixture is stirred for 30 minutes at ambient temperature. Then it is cooled in an ice bath and 4.4 g of sodium cyanoborohydride are added in batches. After 30 minutes stirring at ambient temperature and standing overnight, the mixture is evaporated down, diluted with ice water and adjusted to a pH of 10–11. The mixture is extracted three times with ethyl acetate. The combined ethyl acetate extracts are washed twice with saturated saline solution, dried and evaporated down. The residue is purified by chromatography over an aluminium oxide column (basic).

Yield: 7.35 g (53% of theory),

R_f value: 0.25 (aluminium oxide; ethyl acetate)
(1) (4aRS, 6SR, 8aRS)-6-[(2,2-dimethoxyethyl)amino]-2-methyl-1,2,3,4,4a,5,6,7,8,8a-decahydroisoquinoline is isolated as a by-product of Example V.

R_f value: 0.56 (aluminium oxide; ethyl acetate)

EXAMPLE VI

7-Iodo-3-trifluoroacetyl-2,3,4,5-tetrahydro-1H-3-benzazepine 2.6 g of 7-amino-3-trifluoroacetyl-2,3,4,5-tetrahydro-1H-3-benzazepine are heated briefly with 50 ml of 10% hydrochloric acid with stirring, then cooled to 0° C. and 695 mg of sodium nitrite in 14 ml of water are added dropwise thereto at 0° C. with further cooling. A solution of 1.7 g of potassium iodide and 1.3 g of iodine in 10 ml of water is the added dropwise at 0° C. and the mixture is stirred overnight at ambient temperature. It is then decanted off and the residue obtained is dissolved in methylene chloride. The organic phase is washed with sodium disulphite solution and water, separated off, dried, filtered and evaporated down. The crude product is purified by chromatography over a silica gel column with cyclohexane/ethyl acetate (4:1).

Yield: 2.4 g (65% of theory),

Melting point: 80°–82° C.

$R_f$ value: 0.61 (silica gel; cyclohexane/ethyl acetate=4:1)

EXAMPLE VII

7-Amino-3-trifluoroacetyl-2,3,4,5-tetrahydro-1H-3-benzazepine 3 g of 7-nitro-3-trifluoroacetyl-2,3,4,5-tetrahydro-1H-3-benzazepine are hydrogenated in 200 ml of ethyl acetate with 3 g of 10% palladium on activated charcoal at ambient temperature under a hydrogen pressure of 50 psi for one hour. The catalyst is removed by suction filtration and the filtrate is evaporated down. The residue is heated with tert.butylmethylether and then cooled. The precipitate is suction filtered, washed with tert.butylmethylether and dried.

Yield: 12.2 g (79% of theory),

Melting point: 102°–104° C.

$R_f$ value: 0.31 (silica gel; cyclohexane/ethyl acetate=2:1)

The following compounds are obtained analogously to Example VII:
(1) 7-amino-3-tert.butyloxycarbonyl-2,3,4,5-tetrahydro-1H-3-benzazepine The 3-tert.butyloxycarbonyl-7-nitro-2,3,4,5-tetrahydro-1H-3-benzazepine used as starting material (Melting point: 100°–102° C.) is obtained by reacting 7-nitro-2,3,4,5-tetrahydro-1H-3-benzazepine-hydrochloride with di-tert.butyl pyrocarbonate in the presence of sodium hydroxide solution.

$R_f$ value: 0.40 (silica gel; cyclohexane/ethyl acetate=7:3)
(2) 7-amino-3-ethyl-2,3,4,5-tetrahydro-1H-3-benzazepine
Carried out with Raney nickel in methanol.

$R_f$ value: 0.58 (silica gel; toluene/dioxane/methanol/conc. aqueous ammonia=20:50:20:3)
(3) ethyl 3-(4-aminophenyl)-3-phenyl-propionate-hydrochloride Carried out in ethanol in the presence of ethanolic hydrochloric acid. The starting material ethyl 3-(4-nitrophenyl)-3-phenylacrylate [$R_f$ value: 0.36 (silica gel; cyclohexane/methylene chloride=1:1)] is obtained by reacting 4-nitrobenzophenone with triethyl phosphonoacetic acid.

$R_f$ value: 0.40 (Reversed Phase silica gel; methanol/5% aqueous saline solution=6:4)

EXAMPLE VIII

7-Nitro-3-trifluoroacetyl-2,3,4,5-tetrahydro-1H-3-benzazepine

To a solution of 23.3 g of 3-trifluoroacetyl-2,3,4,5-tetrahydro-1H-3-benzazepine [$R_f$ value: 0.76 (silica gel; cyclohexane/ethyl acetate=1:1), prepared by reacting 2,3,4,5-tetrahydro-1H-3-benzazepine with trifluoroacetic acid anhydride in the presence of N-ethyldiisopropylamine] in 60 ml of conc. sulphuric acid is added dropwise within 1.5 hours, at 0° to 8° C., a mixture of 9.7 g of potassium nitrate and 50 ml of conc. sulphuric acid. The mixture is heated to ambient temperature, poured on to 1 litre of ice and extracted with ethyl acetate. The combined ethyl acetate phases are washed with water and with saturated saline solution, dried and evaporated down. The residue is heated with tert.butyl-methylether. It is then cooled, and the product is suction filtered and washed with tert.butyl-methylether.

Yield: 16.2 g (59% of theory),

Melting point: 116°–119° C.

$R_f$ value: 0.57 (silica gel; cyclohexane/ethyl acetate=2:1)

The following compound is obtained analogously to Example VIII:
(1) 7-nitro-2,3,4,5-tetrahydro-1H-3-benzazepinehydrochloride Carried out with sulphuric acid/potassium nitrate and isolated as the hydrochloride Melting point: 235°–238° C. (Decomp.)

| Calc.: | C 52.52 | H 5.74 | N 12.25 | Cl 15.50 |
|---|---|---|---|---|
| Found: | 52.44 | 5.80 | 12.07 | 15.36 |

EXAMPLE IX

4-[4-[2-(Methoxycarbonyl)ethyl]phenyl]-5-methyl-4H-1,2,4-triazol-3-one 8.1 g of 1-acetyl-4-[4-[2-(methoxycarbonyl)ethyl]-phenyl]-semicarbazide are heated with 60 ml of 1N sodium hydroxide solution over a steam bath for 1.5 hours. The mixture is then cooled somewhat, filtered and the filtrate is acidified slightly with citric acid. It is filtered and the filtrate is combined with concentrated hydrochloric acid. The precipitate is filtered, washed with water and dried. The intermediate product is stirred overnight in methanol with some methanolic hydrochloric acid. The reaction mixture is evaporated down and the residue is triturated with tert.butyl-methylether, suction filtered and dried.

Yield: 4.98 g (65% of theory), $R_f$ value: 0.40 (silica gel; toluene/dioxane/ethanol/glacial acetic acid=90:10:10:6)

| Calc.: | C 59.76 | H 5.79 | N 16.08 |
|---|---|---|---|
| Found: | 59.54 | 5.86 | 16.05 |

The following compounds are obtained analogously to Example IX:
(1) 4-[trans-4-[2-(methoxycarbonyl)ethyl]cyclohexyl]-5-methyl-4H-1,2,4-triazol-3-one Melting point: 179°–181° C.
(2) 4-[trans-4-[2-(methoxycarbonyl)ethyl cyclohexyl]-4H-1,2,4-triazol-3-one Melting point: 142°–144° C.
(3) 4-(3-tert.butyloxycarbonyl-2,3,4,5-tetrahydro-1H-3-benzazepin-7-yl)-4H-1,2,4-triazol-3-one starting material: compound of example III (12)

The intermediate product is reacted with di-tert.butylpyrocarbonate instead of methanolic hydrochloric acid.

melting point: 185°–186° C.

$R_f$ value: 0.25 (silica gel; cyclohexane/ethyl acetate=2:3)

EXAMPLE X

N-[trans-4-[2-(Methoxycarbonyl)ethyl]cyclohexyl]-ethanolamine 5.0 g of N-benzyl-N-[trans-4-[2-(methoxycarbonyl)ethyl] cyclohexyl]-ethanolamine are hydrogenated in 150 ml of methanol with 1.0 g of 10% palladium on activated charcoal for 1¾ hours at 50° C. under a hydrogen pressure of 50 psi. The mixture is filtered and evaporated down.

Yield: 3.3 g (92% of theory), $R_f$ value: 0.20 (silica gel; methylene chloride/methanol/ conc. aqueous ammonia=9:1:0.4)

The following compounds are obtained analogously to Example X:

(1) tert.butyl (trans-4-aminocyclohexyl)oxyacetate

The starting material, tert.butyl [trans-(4-dibenzylamino) cyclohexyl]-oxyacetate [$R_f$ value: 0.51; (silica gel; cyclohexane/ethyl acetate=4:1)], is obtained by reacting trans-4-(dibenzylamino)cyclohexanol with tert.butyl bromoacetate in toluene/50% sodium hydroxide solution in the presence of tetrabutylammonium-hydrogen sulphate.

$R_f$ value: 0.56 (Reversed Phase silica gel; methanol/5% aqueous saline solution=6.4).

(2) N-(3-hydroxypropyl)-N-[trans-4-[2-(methoxycarbonyl) ethyl]cyclohexyl]-amine $R_f$ value: 0.10 (silica gel; methylene chloride/methanol= 9:1)

(3) methyl [[trans-4-[2-(methoxycarbonyl)ethyl]cyclohexyl] amino]-acetate-hydrochloride Melting point: 166°–168° C. Hydrogenation in the presence of methanolic hydrochloric acid.

$R_f$ value: 0.69 (silica gel; methylene chloride/methanol/ conc. aqueous ammonia=95:5:1)

EXAMPLE XI

N-Benzyl-N-[trans-4-[2-(methoxycarbonyl)ethyl] cyclohexyl]-ethanolamine 6.2 g of N-[trans-4-[2-(methoxycarbonyl)ethyl] cyclohexyl]-benzylamine-hydrochloride, 12.8 g of N-ethyl-diisopropylamine and 5.0 g of 2-bromoethanol are stirred at 100° C. for 22 hours and then cooled. The mixture is divided between ethyl acetate and water, the aqueous phase is extracted with ethyl acetate and the combined ethyl acetate phases are washed with saturated saline solution. The ethyl acetate phase is evaporated down and the residue is purified by chromatography over a silica gel column using methylene chloride/methanol (9:1).

Yield: 5.1 g (80% of theory), $R_f$ value: 0.67 (silica gel; methylene chloride/methanol= 9:1)

The following compounds are obtained analogously to Example XI:

(1) N-(3-hydroxypropyl)-N-[trans-4-[2-(methoxycarbonyl) ethyl]cyclohexyl]-benzylamine $R_f$ value: 0.70 (silica gel; methylene chloride/methanol 9:1).

(2) methyl N-benzyl-[[trans-4-[(2-methoxycarbonyl)ethyl] cyclohexyl]amino]-acetate $R_f$ value: 0.86 (silica gel; cyclohexane/ethyl acetate=3:7)

(3) 3-ethyl-7-nitro-2,3,4,5-tetrahydro-1H-3-benzazepine $R_f$ value: 0.32 (silica gel; methylene chloride/methanol= 95:5)

EXAMPLE XII

N-[trans-4-[2-(Methoxycarbonyl)ethyl]cyclohexyl] benzylamine-hydrochloride 8.0 g of methyl 3-(trans-4-aminocyclohexyl)propionate-hydrochloride, 4.3 g of benzaldehyde and 5.0 ml of triethylamine in 150 ml of methanol are hydrogenated with 1.0 g of Raney nickel at 50° C. under a hydrogen pressure of 50 psi for 4 hours. After cooling, the mixture is suction filtered and the filtrate is evaporated down. The residue is divided between ethyl acetate and water, the aqueous phase is adjusted to pH 8–9 with sodium hydroxide solution and extracted with ethyl acetate. The combined ethyl acetate phases are washed with saturated saline solution, dried and evaporated down. The residue is suspended in diethylether and mixed with methanolic hydrochloric acid. The precipitate is suction filtered, washed with diethylether and dried.

Yield: 7.4 g (66% of theory),

Melting point: 170°–172° C.

| Calc.: | C 65.47 | H 8.40 | N 4.49 | Cl 11.37 |
|---|---|---|---|---|
| Found: | 65.38 | 8.44 | 4.46 | 11.40 |

EXAMPLE XIII

Methyl(trans-4-aminocyclohexyl)oxyacetate-hydrochloride

Hydrochloric acid gas is piped for an hour over a solution of 59.4 g of tert.butyl (trans-4-aminocyclohexyl)oxyacetate in 500 ml of methanol, cooled in an ice bath, and then the mixture is stirred overnight at ambient temperature. It is evaporated to dryness, the residue is triturated with acetone and the solid is suction filtered and dried.

Yield: 34.3 g (59% of theory),

Melting point: 157°–160° C.

EXAMPLE XIV 2-(3-Trifluoroacetyl-2,3,4,5-tetrahydro-1H-3-benzazepin-7-yl)-3,4-dihydro-2H,5H-1,2,5-thiadiazole-1,1-dioxide a) N-(2-Chloroethyl)-N'-(3-trifluoroacetyl-2,3,4,5-tetrahydro-1H-3-benzazepin-7-yl)-sulphuric acid diamide To a mixture of 7.6 g of 7-amino-3-trifluoroacetyl-2,3,4, 5-tetrahydro-1H-3-benzazepine and 7.7 ml of N-ethyl-diisopropylamine in 70 ml of methylene chloride are added dropwise, at −5° C., 4.8 g of [(2-chloroethyl)amino] sulphonylchloride in 30 ml of methylene chloride. The mixture is stirred for an hour at 0° C. and overnight at ambient temperature. The reaction mixture is diluted with methylene chloride and washed with water, 1N hydrochloric acid and again with water. The organic phase is dried, evaporated down and the residue is purified by chromatography over a silica gel column using cyclohexane/ethyl acetate (1:1).

Yield: 7.8 g (72% of theory),

Melting point: 128°–130° C.

$R_f$ value: 0.64 (silica gel; cyclohexane/ethyl acetate=1:1)

b) 2-(3-Trifluoroacetyl-2,3,4,5-tetrahydro-1H-3-benzazepin-7-yl)-3,4-dihydro-2H,5H-1,2,5-thiadiazole-1,1-dioxide 7.8 g of the compound of Example XIVa) are dissolved in 20 ml of dimethylformamide and mixed with 2.5 g of potassium tert.butoxide. After 3 hours stirring at ambient temperature, it is added to 300 ml of an aqueous 15% citric acid solution and extracted three times with ethyl acetate. The combined organic phases are dried and evaporated down and the residue is purified by chromatography over a silica gel column using cyclohexane/ethyl acetate (1:1).

Yield: 2.1 g (30% of theory)

Melting point: 165°–167° C.

$R_f$ value: 0.30 (silica gel; cyclohexane/ethyl acetate=1:1)

EXAMPLE XV (3-Methyl-2,3,4,5-tetrahydro-1H-3-benzazepin-7-yl)-boric acid

To 7.1 g 7-jodo-3-methyl-2,3,4,5-tetrahydro-1H-3-benzazepin ($R_f$ value: 0.85 (silica gel; toluene/dioxane/methanol/conc. aqueous ammonia=20:50:20:5); prepared from the compound of example VI by reaction with sodium hydroxide solution/methanol and subsequent reaction with formaline/formic acid] in 50 ml of diethylether are given at −70° to −75° C. 17.7 ml of 1.6M n-butyl lithium, dissolved in hexane. After stirring for 30 minutes at −70° C. 5.7 ml of triisopropyl borate in 30 ml of diethylether are added to the reaction mixture. Subsequently the mixture is stirred one hour at −75° C., then warmed up to −50° C. After adding 70 ml of water and stirring for one hour at room temperature, the aqueous phase was separated. The aqueous phase is adjusted to a pH-value of 8 to 8.5 with glacial acetic acid. The precipitate is filtered, washed with a small amount of cold water and dried at 60° C.

Yield: 3.7 g (73% of theory), melting point: 153°–155° C. (sintering from 148° C.)

$R_f$ value: 0.80 (reversed phase silica gel; methanol/5% aqueous saline solution=6:4)

EXAMPLE XVI

1-[2-(ethoxycarbonyl)ethyl]-3-[4-(trifluoromethylsulfonyloxy)phenyl]-imidazolidin-2-one a) N-(2,2-Diethoxyethyl)-4-benzyloxy-aniline Prepared from 4-benzyloxy-aniline and bromoacetaldehydediethylacetal in the presence of N-ethyldiisopropylamine.

$R_f$ value: 0.42 (silica gel; cyclohexane/ethyl acetate=85:15)

b) N-(4-Benzyloxyphenyl)-N-(2.2-diethoxyethyl)-N'-[2-(ethoxycarbonyl)ethyl]-urea Prepared from N-(2,2-diethoxyethyl)-4-benzyloxy-aniline and [2-(ethoxycarbonyl)ethyl]-isocyanate.

$R_f$ value: 0.45 (silica gel;cyclohexane/ethyl acetate=1:1 c) 1-(4-Benzyloxyphenol)-3-[2-(ethoxycarbonyl)ethyl]-3H-imidazol-2-one

Prepared from N-(4-benzyloxyphenyl)-N-(2,2-diethoxyethyl)-N'-[2-(ethoxycarbonyl)ethyl]-urea and trifluoroacetic acid in methylene chloride.

melting point: 66°–68° C.

$R_f$ value: 0.41 (silica gel; cyclohexane/ethyl acetate=1:1)

d) 1-(4-hydroxyphenyl)-3- [2-(ethoxycarbonyl)ethyl]-imidazolidin-2-one

Prepared from 1-(4-benzyloxyphenyl)-3-[2-(ethoxycarbonyl)ethyl]-3H-imidazol-2-one by hydrogenation in the presence of palladium on charcoal in ethanol at 40° C. and a hydrogen pressure of 50 psi. $R_f$ value: 0.20 (silica gel; methylene chloride/methanol=100:2)

e) 1-[2-(Ethoxycarbonyl)ethyl[-3-[4-(trifluoromethylsulfonyloxy)-phenyl]-imidazolidin-2-on Prepared from 1-(4-hydroxyphenyl)-3-[2-(ethoxycarbonyl)ethyl]-imidazolidin-2-one and trifluoromethanesulfonic acid anhydride in pyridine at 0° C.

melting point: 81°–83° C.

$R_f$ value: 0.66 (silica gel; methylene chloride/methanol=100:1)

| Calculated: | C 43.90 | H 4.18 | N 6.83 | S 7.81 |
|---|---|---|---|---|
| Found: | 43.92 | 4.20 | 6.98 | 7.91 |

EXAMPLE 1

1-(1-Aminoisoquinolin-6-yl)-3-[4-(2-carboxyethyl)phenyl]-imidazolidin-2-one×1 water×1.2 acetic acid 300 mg of 3-[4-(2-carboxyethyl)phenyl]-1-(1-chloroisoquinolin-6-yl)-imidazolidin-2-one, 895 mg of acetamide and 524 mg of potassium carbonate are mixed thoroughly in a mortar and then heated to 200° C. for 3 hours under nitrogen and with stirring. After cooling the mixture is combined with 20 ml of water and adjusted to pH 8–9 using 1N hydrochloric acid. The precipitate is suction filtered and washed several times with water. After drying, the precipitate is suspended in 50 ml of methylene chloride/methanol (4:1) and exposed to ultrasound for 30 minutes in an ultrasound bath. The precipitate is suction filtered and the treatment with methylene chloride/methanol in the ultrasound bath is repeated twice. The filter residue is stirred in a mixture of 30 ml of methanol and 10 ml of glacial acetic acid with gentle heating. The insoluble matter is filtered off and the mother liquor is evaporated to dryness. The residue is mixed with toluene once again and evaporated down. Then it is dried at 60° C. in vacuo.

Yield: 70 mg (20% of theory),

Melting point: >250° C., $R_f$ value: 0.78 (Reversed Phase silica gel; methanol/5% aqueous saline solution=8:4)

| Calc.: | C 60.25 | H 5.79 | N 12.01 |
|---|---|---|---|
| Found: | 60.20 | 5.43 | 11.54 |

EXAMPLE 2

3-[4-(2-Carboxyethyl)phenyl]-1-(1-chloroisoquinolin-6-yl)-imidazolidin-2-one 1 g of 1-(1-chloroisoquinolin-6-yl)-3-[4-[2-(methoxycarbonyl)-ethyl]phenyl]-imidazolidin-2-one, 100 ml of dioxane, 80 ml of water and 8.5 ml of 1N sodium hydroxide solution are stirred for 3 hours at ambient temperature. 9 ml of 1N hydrochloric acid are added, the mixture is evaporated down and the precipitate is suction filtered. The product is washed with water and dried at 50° C.

Yield: 0.78 g (80% of theory),

Melting point: 236°–240° C. (Decomp.)

$R_f$ value: 0.36 (silica gel; methylene chloride/ethanol/ethyl acetate=20:1:1)

The following compounds are obtained analogously to Example 2:

(1) 1-[4-(2-carboxyethyl)phenyl]-3-(isoquinolin-6-yl)-3H-imidazol-2-one

Melting point: 305°–310° C., $R_f$ value: 0.49 (silica gel; methylene chloride/methanol=9:1)

| Calc.: | C 70.18 | H 4.77 | N 11.69 |
|---|---|---|---|
| Found: | 69.95 | 4.93 | 11.64 |

(2) 1-[4-(2-carboxyethyl)phenyl]-3-(1,2,3,4-tetrahydroisoquinolin-6-yl)-imidazolidin-2-one $R_f$ value: 0.44 (Reversed Phase silica gel; methanol/5% aqueous saline solution=6:4)

| Calc.: | C 67.54 | H 6.21 | N 11.25 |
|---|---|---|---|
| Found: | 67.58 | 6.42 | 11.23 |

(3) 1-[4-(2-carboxyethyl)phenyl]-3-(2,3,4,5-tetrahydro-1H-3-benzazepin-7-yl)-3H-imidazol-2-one (4) 2-[trans-4-(2-methoxycarbonyl)ethyl]-5-(2,3,4,5-tetrahydro-1H-3-benzazepin-7-yl)-3,4-dihydro-2H,5H-1,2,5-thiadiazole-1,1-dioxide Carried out in methanol/sodium hydroxide solution; starting material: compound of Example 18.

$R_f$ value: 0.36 (Reversed Phase silica gel; methanol/5% aqueous saline solution=6:4)

(5) 3-[4-(2-carboxyethyl)phenyl]-1-(2,3,4,5-tetrahydro-1H-3-benzazepin-7-yl)-imidazolidin-2,4-dione
(6) 1-(4-[2-carboxy-2-(n-butylsulphonylamino)ethyl]phenyl)-3-(2,3,4,5-tetrahydro-1H-3-benzazepin-7-yl)-imidazolidin-2-one
(7) 1-[4-[2-carboxy-2-(n-pentylcarbonylamino)ethyl]phenyl]-3-(2,3,4,5-tetrahydro-1H-3-benzazepin-7-yl)-imidazolidin-2-one
(8) 1-[4-(2-carboxyethyl)phenyl]-3-(5,6,7,8-tetrahydropyrido[3,4-d]pyrimidin-2-yl)-imidazolidin-2-one
(9) 1-[4-[(carboxymethyl)sulphonyl]phenyl]-3-(2,3,4,5-tetrahydro-1H-3-benzazepin-7-yl)-imidazolidin-2-one
(10) 1-[(4-carboxy-1-piperidinyl)carbonylmethyl]-3-(2,3,4,5-tetrahydro-1H-3-benzazepin-7-yl)-imidazolidin-2-one
(11) 1-[2-[(2-carboxyethyl)aminocarbonyl]ethyl]-3-(2,3,4,5-tetrahydro-1H-3-benzazepin-7-yl)-imidazolidin-2-one
(12) 1-[4-(2-carboxyethyl)phenyl]-3-(2,3,4,5-tetrahydro-1H-2-benzazepin-7-yl)-imidazolidin-2-one
(13) 1-[4-(2-carboxyethyl)phenyl]-3-(1,1-dimethyl-1,2,3,4-tetrahydro-isoquinolin-6-yl)-imidazolidin-2-one

EXAMPLE 3

1-(1-Chloroisoquinolin-6-yl)-3-[4-[2-(methoxycarbonyl)ethyl]-phenyl]-imidazolidin-2-one 2.2 g of 1-(isoquinolin-N-oxid-6-yl)-3-[4-[2-(methoxycarbonyl)-ethyl]phenyl]-imidazolidin-2-one and 25 ml of phosphorus oxychloride are refluxed for 2 hours. The phosphorus oxychloride is then distilled off and the residue is mixed with ice. The pH of the mixture is adjusted to 8–9 using saturated sodium hydrogen carbonate solution. It is extracted several times with methylene chloride, the organic phases are dried and evaporated down and the residue is purified by chromatography over a silica gel column with methylene chloride/methanol (20:1).

Yield: 1.0 g (43% of theory), $R_f$ value: 0.66 (silica gel; methylene chloride/methanol= 20:1)

EXAMPLE 4

1-(Isoquinolin-6-yl)-3-[4-[2-(methoxycarbonyl) ethyl]-phenyl]-imidazolidin-2-one To a solution of 3.0 g of N-(2-hydroxyethyl)-N'-(isoquinolin-6-yl)-N-[4-[2-(methoxycarbonyl)ethyl] phenyl]-urea and 2.0 g of triphenylphosphine in 105 ml of acetonitrile are added, at an internal temperature of 42° to 52° C., 1.31 ml of diethyl azodicarboxylate in 36 ml of acetonitrile. After 2 hours stirring at 45° C. the mixture is cooled to −5° C. and stirred for a further 2 hours. The precipitate is suction filtered and washed with a little cold acetonitrile.

Yield: 2.6 g (90% of theory),

Melting point: 213°–215° C., $R_f$ value: 0.60 (silica gel; methylene chloride/methanol= 20:1:1)

The following compounds are obtained analogously to Example 4:

(1) 1-(3-tert.butyloxycarbonyl-2,3,4,5-tetrahydro-1H-3-benzazepin-7-yl)-3-[4-[2-(methoxycarbonyl)ethyl]phenyl]-imidazolidin-2-one Melting point: 165°–167° C.

$R_f$ value: 0.77 (silica gel; methylene chloride/ethyl acetate=9:1)

(2) 1-[trans-4-[2-(methoxycarbonyl)ethyl]cyclohexyl]-3-(3-trifluoroacetyl-2,3,4,5-tetrahydro-1H-3-benzazepin-7-yl)-imidazolidin-2-one Melting point: 250°–255° C. (Decomp.)

$R_f$ value: 0.45 (silica gel; cyclohexane/ethyl acetate=1:1)

(3) 1-[4-[trans-2-(methoxycarbonyl)ethenyl]phenyl]-3-(3-trifluoroacetyl-2,3,4,5-tetrahydro-1H-3-benzazepin-7-yl)-imidazolidin-2-one Melting point: 216°–220° C.

$R_f$ value: 0.38 (silica gel; cyclohexane/ethyl acetate=1:1)

(4) 1-[trans-4-[2-(methoxycarbonyl)ethyl]cyclohexyl]-3-(3-trifluoroacetyl-2,3,4,5-tetrahydro-1H-3-benzazepin-7-yl)-3,4,5,6-tetrahydro-1H-pyrimidin-2-one Melting point: 125°–127° C.

$R_f$ value: 0.54 (silica gel; cyclohexane/ethyl acetate=1:2)

EXAMPLE 5

1-(Isoquinolin-6-yl)-3-[4-[2-(methoxycarbonyl) ethyl]phenyl]-3H-imidazol-2-one 7.3 g of N-(2,2-diethoxyethyl)-N'-(isoquinolin-6-yl)-N-[4-[2-(methoxycarbonyl)ethyl]phenyl]-urea are stirred in 35 ml of trifluoroacetic acid for 2 hours at ambient temperature. Then the mixture is partly evaporated down and ice water is added. It is made alkaline with sodium hydroxide solution, with stirring and cooling, the precipitate is suction filtered and washed with a little methanol. The product is then recrystallised from methanol.

Yield: 4.45 g (76% of theory),

Melting point: 158°–161° C., $R_f$ value: 0.29 (silica gel; methylene chloride/methanol= 95:5)

| Calc.: | C 70.76 | H 5.13 | N 11.25 |
|---|---|---|---|
| Found: | 70.52 | 5.08 | 11.35 |

The following compounds are obtained analogously to Example 5:

(1) 1-[trans-4-[2-(methoxycarbonyl)ethyl]cyclohexyl]-3-(3-trifluoroacetyl-2,3,4,5-tetrahydro-1H-3-benzazepin-7-yl)-3H-imidazol-2-one Carried out by dry heating to 160°–170° C.

Melting point: 121°–124° C., $R_f$ value: 0.35 (silica gel; cyclohexane/ethyl acetate=1:1).

(2) 1-[trans-4-[[(methoxycarbonyl)methyl]oxy]cyclohexyl]-3-(3-trifluoroacetyl-2,3,4,5-tetrahydro-1H-3-benzazepin-7-yl)-3H-imidazol-2-one Melting point: 148°–149° C.

$R_f$ value: 0.28 (silica gel; ethyl acetate/cyclohexane=2:1)

(3) 1-[4-[2-(ethoxycarbonyl)-1-propyl]phenyl]-3-(3-trifluoroacetyl-2,3,4,5-tetrahydro-1H-3-benzazepin-7-yl)-3H-imidazol-2-one $R_f$ value: 0.32 (silica gel; cyclohexane/ethyl acetate=2:1)

(4) 1-[trans-4-[2-(methoxycarbonyl)ethyl]cyclohexyl]-3-(3-ethyl-2,3,4,5-tetrahydro-1H-3-benzazepin-7-yl)-3H-imidazol-2-one $R_f$ value: 0.30 (Reversed Phase silica gel; methanol/5% aqueous saline solution=6:4)

(5) 1-[trans-4-[2-(methoxycarbonyl)ethyl]cyclohexyl]-3-(7-ethyl-6,7,8,9-tetrahydro-5H-pyrazino[2,3-d]azepin-2-yl)-3H-imidazol-2-one Melting point: 135°–136° C.

| | | | | | | | |
|---|---|---|---|---|---|---|---|
| Calc.: | C | 64.61 | H | 7.78 | N | 16.38 | |
| Found: | | 64.82 | | 7.84 | | 16.27 | |

(6) 1-[4-[2-(ethoxycarbonyl)-1-phenyl-ethyl]phenyl]-3-3-(3-trifluoroacetyl-2,3,4,5-tetrahydro-1H-3-benzazepin-7-yl)-3H-imidazol-2-one $R_f$ value: 0.24 (silica gel; cyclohexane/ethyl acetate=7:3)

(7) 1-[trans-4-[2-(methoxycarbonyl)ethyl]cyclohexyl]-3-(7-benzyl-6,7,8,9-tetrahydro-5H-yl)-3H-imidazol-2-one Melting point: 131°–134° C.

$R_f$ value: 0.38 (silica gel; methylene chloride/methanol=20:1)

1-[4-[2-(Methoxycarbonyl)ethyl]phenyl]-3-(1,2,3,4-tetrahydro-isoquinolin-6-yl)-imidazolidin-2-one-acetate 2.0 g of 1-(isoquinolin-6-yl)-3-[4-[2-(methoxycarbonyl)ethyl]-phenyl]-3H-imidazol-2-one in 50 ml of glacial acetic acid are hydrogenated with 0.5 g of platinum oxide at ambient temperature under a hydrogen pressure of 50 psi for 40 minutes. The catalyst is filtered off, the filtrate is evaporated down and the residue is recrystallized from methanol.

Yield: 1.7 g (72% of theory),

Melting point: 170°–173° C. (Decomp.)

| | | | | | | |
|---|---|---|---|---|---|---|
| Calc.: | C | 65.59 | H | 6.65 | N | 9.56 |
| Found: | | 65.90 | | 6.78 | | 9.69 |

$R_f$ value: 0.30 (silica gel; toluene/dioxane/methanol/conc. aqueous ammonia=20:50:20:5)

Mass spectrum: M⁺=379

The following compounds are obtained analogously to Example 6:

(1) 1-[trans-4-[2-(methoxycarbonyl)ethyl]cyclohexyl]-3-(1,2,3,4-tetrahydro-isoquinolin-6-yl)-imidazolidin-2-one-acetate (2) 1-[trans-4-(2-Carboxyethyl)cyclohexyl]-3-(3-methyl-2,3,4,5,5a,6,7,8,9,9a-decahydro-1H-3-benzazepin-7-yl)imidazolidin-2-one-×1.35 HCl×1.9 H₂O Dioxane/water and platinium-rhodium-catalyst are used. As starting material is used the compound of example 19.

Mass spectrum: M+=405

| | | | | | | | |
|---|---|---|---|---|---|---|---|
| Calculated: | C | 56.49 | H | 9.10 | N | 8.5 | Cl 9.79 |
| | | 56.63 | | 8.81 | | 8.60 | 9.92 |

(3) 1-[trans-4-(2-Carboxyethyl)cyclohexyl]-3-(2,3,4,5,5a,6,7,8,9,9a-decahydro-1H-3-benzazepin-7-yl)imidazolidin-2-one-×1.05 HCl×0.9 H₂O Dioxane/water and platinium-rhodium-catalyst are used. As starting material is use the compound of example 14(1)

Mass spectrum: M+=391

| | | | | | | | |
|---|---|---|---|---|---|---|---|
| Calculated: | C 59.43 | H 9.03 | N 9.45 | Cl 8.05 |
| | 59.49 | 8.83 | 9.35 | 8.30 |

EXAMPLE 7

1-[4-[2-(Isobutyloxycarbonyl)ethyl]phenyl]-3-(1,2,3,4-tetrahydroisoquinolin-6-yl)-imidazolidin-2-one-hydrochloride×1 water Hydrochloric acid is piped for 30 minutes, with stirring, over a suspension of 150 mg of 1-[4-(2-carboxyethyl) phenyl]-3-(1,2,3,4-tetrahydro-isoquinolin-6-yl)-imidazolidin-2-one in 4.6 ml of isobutanol. The mixture is stirred overnight at ambient temperature, acetone is added and the precipitate is suction filtered. The product is suspended in acetone, suction filtered, washed with acetone and diethylether and dried.

Yield: 140 mg (77% of theory),

| | | | | | | | |
|---|---|---|---|---|---|---|---|
| Calc.: | C | 65.56 | H | 7.04 | N | 9.18 | Cl 7.74 |
| Found: | | 65.38 | | 7.03 | | 9.47 | 7.92 |

$R_f$ value: 0.19 (Reversed Phase silica gel; methanol/5% saline solution=6:4)

Mass spectrum: M⁺=421

The following compounds are obtained analogously to Example 7:

(1) 1-[4-[2-(isopropyloxycarbonyl)ethyl]phenyl]-3-(2,3,4,5-tetrahydro-1H-3-benzazepin-7-yl)-imidazolidin-2-one-hydrochloride

| | | | | | | | |
|---|---|---|---|---|---|---|---|
| Calc.: | C | 63.08 | H | 7.20 | N | 8.83 | Cl 7.45 |
| Found: | | 62.79 | | 7.14 | | 8.83 | 7.80 |

$R_f$ value: 0.21 (Reversed Phase silica gel; methanol/5% saline solution=6:4)

Mass spectrum: M⁺=421

(2) 1-[4-[2-(cyclohexyloxycarbonyl)ethyl]phenyl]-3-(2,3,4,5-tetrahydro-1H-3-benzazepin-7-yl)-imidazolidin-2-one-hydrochloride (3) 1-[4-[2-(methoxycarbonyl)ethyl]phenyl]-3-(3-methyl-2,3,4,5-tetrahydro-1H-3-benzazepin-7-yl)-imidazolidin-2-one-hydrochloride×0.75 H₂O Melting point: 248°–250° C.,

| | | | | | | | |
|---|---|---|---|---|---|---|---|
| Calc.: | C | 63.01 | H | 6.94 | N | 9.19 | Cl 7.75 |
| Found: | | 63.09 | | 6.98 | | 9.22 | 7.88 |

$R_f$ value: 0.28 (Reversed Phase silica gel; methanol/5% aqueous saline solution=6:4)

(4) 1-[4-[2-(ethoxycarbonyl)ethyl]phenyl]-3-(3-methyl-2,3,4,5-tetrahydro-1H-3-benzazepin-7-yl)-imidazolidin-2-one-hydrochloride $R_f$ value: 0.22 (Reversed Phase silica gel; methanol/5% aqueous saline solution=6:4)

(5) 1-[4-[2-(isopropyloxycarbonyl)ethyl]phenyl]-3-(3-methyl-2,3,4,5-tetrahydro-1H-3-benzazepin-7-yl)imidazolidin-2-one-hydrochloride R$_f$ value: 0.19 (Reversed Phase silica gel; methanol/5% aqueous saline solution=6:4)

(6) 1-[trans-4-[2-(isopropyloxycarbonyl)ethyl]cyclohexyl]-3-(3-methyl-2,3,4,5-tetrahydro-1H-3-benzazepin-7-yl)-imidazolidin-2-one-hydrochloride Thionylchloride and hydrochloric acid gas are used.

Melting point: >250° C.,

R$_f$ value: 0.17 (Reversed Phase silica gel; methanol/5% aqueous saline solution=6:4)

| Calc.: | C | 65.32 | H | 8.43 | N | 8.79 | Cl | 7.42 |
|---|---|---|---|---|---|---|---|---|
| Found: | | 65.10 | | 8.41 | | 8.91 | | 7.66 |

(7) 1-[trans-4-[2-(ethoxycarbonyl)ethyl]cyclohexyl]-3-(3-methyl-2,3,4,5-tetrahydro-1H-3-benzazepin-7-yl)imidazolidin-2-one-hydrochloride Thionylchloride and hydrochloric acid gas are used.
Melting point: >250° C.

R$_f$ value: 0.24 (Reversed Phase silica gel; methanol/5% aqueous saline solution=6:4)

| Calc.: | C | 64.71 | H | 8.25 | N | 9.09 | Cl | 7.64 |
|---|---|---|---|---|---|---|---|---|
| Found: | | 64.09 | | 8.22 | | 9.08 | | 7.72 |

(8) 1-[trans-4-[2-(methoxycarbonyl)ethyl]cyclohexyl]-3-(3-methyl-2,3,4,5-tetrahydro-1H-3-benzazepin-7-yl)-imidazolidin-2-one-hydrochloride Thionylchloride and hydrochloric acid gas are used.
Melting point: >250° C.

R$_f$ value: 0.29 (Reversed Phase silica gel; methanol/5% aqueous saline solution=6:4)

| Calc.: | C | 64.05 | H | 8.04 | N | 9.34 | Cl | 7.88 |
|---|---|---|---|---|---|---|---|---|
| Found: | | 64.10 | | 7.97 | | 9.52 | | 8.11 |

(9) 1-[trans-4-[2-(isopropyloxycarbonyl)ethyl]cyclohexyl]-3-(2,3,4,5-tetrahydro-1H-3-benzazepin-7-yl)-imidazolidin-2-one-hydrochloride Thionylchloride and hydrochloric acid gas are used.

R$_f$ value: 0.20 (Reversed Phase silica gel; methanol/5% aqueous saline solution=6:4)

(10) 1-[trans-4-[2-(ethoxycarbonyl)ethyl]cyclohexyl]-3-(2,3,4,5-tetrahydro-1H-3-benzazepin-7-yl)-imidazolidin-2-one-hydrochloride Thionylchloride and hydrochloric acid gas are used.

R$_f$ value: 0.23 (Reversed Phase silica gel; methanol/5% aqueous saline solution=6:4)

| Calc.: | C | 64.05 | H | 8.06 | N | 9.34 | Cl | 7.88 |
|---|---|---|---|---|---|---|---|---|
| Found: | | 63.77 | | 8.23 | | 9.07 | | 7.91 |

(11) 1-[trans-4-[2-(methoxycarbonyl)ethyl]cyclohexyl]-3-(2,3,4,5-tetrahydro-1H-3-benzazepin-7-yl)-imidazolidin-2-one-hydrochloride Thionylchloride and hydrochloric acid gas are used.

R$_f$ value: 0.26 (Reversed Phase silica gel; methanol/5% aqueous saline solution=6:4)

| Calc.: | C | 63.36 | H | 7.86 | N | 9.64 | Cl | 8.13 |
|---|---|---|---|---|---|---|---|---|
| Found: | | 63.34 | | 7.88 | | 9.73 | | 8.11 |

EXAMPLE 8

1-[4-(2-Carboxyethyl)phenyl]-3-(2-methyl-1,2,3,4-tetrahydroisoquinolin-6-yl)-imidazolidin-2-one ×0.2 water 350 mg of 1-[4-[2-(methoxycarbonyl)ethyl]phenyl]-3-(1,2,3,4-tetrahydroisoquinolin-6-yl)-imidazolidin-2-one-acetate, 0.7 ml of water, 0.15 ml of formic acid and 0.7 ml of 37% aqueous formaldehyde solution are stirred for one hour at 65° C. Toluene is added and the mixture is evaporated down. It is mixed with toluene and evaporated down once more. The residue is stirred with 2 ml of tetrahydrofuran, 1 ml of water and 0.8 ml of 4N sodium hydroxide solution for 2½ days at ambient temperature. 220 mg of ammonium chloride in 1 ml of water are added and the mixture is stirred for 2 hours. The reaction mixture is partly evaporated down, cooled with ice and the solid product is suction filtered. The solid is washed with water, acetone and diethylether and then dried.

Yield: 220 ml (72% of theory),
Melting point: 245°–248° C.

| Calc.: | C | 68.98 | H | 6.68 | N | 10.97 |
|---|---|---|---|---|---|---|
| Found: | | 68.91 | | 6.69 | | 10.92 |

R$_f$ value: 0.41 (Reversed Phase silica gel; methanol/5% aqueous saline solution=6:4)

Mass spectrum: M$^+$=379

The following compound is obtained analogously to

EXAMPLE 8

(1) 1-[4-(2-carboxyethyl)phenyl]-3-(3-methyl-2,3,4,5-tetrahydro-1H-3-benzazepin-7-yl)-imidazolidin-2-one-hydrochloride×1.5 water The final ester cleaving is carried out with glacial acetic acid/hydrochloric acid instead of with sodium hydroxide solution.

| Calc.: | C | 60.45 | H | 6.84 | N | 9.20 | Cl | 7.76 |
|---|---|---|---|---|---|---|---|---|
| Found: | | 60.45 | | 6.86 | | 9.18 | | 8.09 |

R$_f$ value: 0.31 (silica gel; methylene chloride/methanol/conc. aqueous ammonia=4:1:0.2)

Mass spectrum: M$^+$=393

EXAMPLE 9

1-[4-(2-Carboxyethyl)phenyl]-3-(2,3,4,5-tetrahydro-1H-3-benzazepin-7-yl)-imidazolidin-2-one 800 mg of 1-[4-[2-(methoxycarbonyl)ethyl]phenyl]-3-(2,3,4,5-tetrahydro-1H-3-benzazepin-7-yl)-imidazolidin-2-one-hydrochloride are stirred with 10 ml of semiconcentrated hydrochloric acid and 10 ml of glacial acetic acid. After 2 hours, a further 5 ml of semiconcentrated hydrochloric acid and 5 ml of glacial acetic acid are added and the mixture is stirred overnight at ambient temperature. The reaction mixture is evaporated down and the residue is suspended in 10 ml of water. A pH of 6 is achieved using 2N sodium hydroxide solution, the solid is suction filtered, washed with ice water and then dried.

Yield: 560 mg (79% of theory), $R_f$ value: 0.40 (Reversed Phase silica gel; methanol/5% aqueous saline solution=6:4)

Mass spectrum: $M^+$=379

The following compounds are obtained analogously to Example 9:

(1) 1-[4-(2-carboxyethyl)phenyl]-3-(4aRS,6RS,8aRS)-1,2,3,4,4a,5,6,7,8,8a-decahydroisoquinolin-6-yl)-imidazolidin-2-one-hydrochloride Isolated as the hydrochloride $R_f$ value: 0.41 (Reversed Phase silica gel; methanol/5% aqueous saline solution=6:4)

Mass spectrum: $M^+$=371

(2) 1-[4-(2-carboxyethyl)phenyl]-3-(3-ethyl-2,3,4,5-tetrahydro-1H-3-benzazepin-7-yl)-imidazolidin-2-one-hydrochloride $R_f$ value: 0.36 (Reversed Phase silica gel; methanol/5% aqueous saline solution=6:4)

Mass spectrum: $M^+$=407

(3) 1-[4-(2-carboxyethyl)phenyl]-3-(3-isopropyl-2,3,4,5-tetrahydro-1H-3-benzazepin-7-yl)-imidazolidin-2-one-hydrochloride (4) 1-(2-carboxyethyl)-3-[4-(isoquinolin-6-yl)phenyl]-imidazolidin-2-one-hydrochloride (5) 1-[4-(2-carboxyethyl)phenyl]-3-(4,4-dimethyl-1,2,3,4-tetrahydroisoquinolin-6-yl)-imidazolidin-2-one-hydrochloride (6) 1-[4-(2-carboxyethyl)phenyl]-3-(3-butyl-2,3,4,5-tetrahydro-1H-3-benzazepin-7-yl)-imidazolidin-2-one-hydrochloride $R_f$ value: 0.33 (Reversed Phase silica gel; methanol/5% aqueous saline solution=6:4)

Mass spectrum: $M^+$=435

(7) 1-[4-(2-carboxyethyl)phenyl]-3-(1-amino-3,4-dihydroisoquinolin-6-yl)-imidazolidin-2-one-hydrochloride (8) 1-[4-(2-carboxyethyl)phenyl]-3-(2-methyl-3,4-dihydroquinazolin-7-yl)-imidazolidin-2-one-hydrochloride (9) 1-[4-(2-carboxyethyl)phenyl]-3-(4,4-dimethyl-3,4-dihydroquinazolin-7-yl)-imidazolidin-2-one-hydrochloride

(10) 3-[trans-4-(2-carboxyethyl)cyclohexyl]-1-(2,3,4,5-tetrahydro-1H-3-benzazepin-7-yl)-hydantoin-hydrochloride Melting point: >250° C.

$R_f$ value: 0.36 (Reversed Phase silica gel; methanol/5% aqueous saline solution=6:4).

| Calc.: | C | 60.61 | H | 6.94 | N | 9.64 | Cl | 8.13 |
|---|---|---|---|---|---|---|---|---|
| Found: | | 60.45 | | 6.90 | | 9.61 | | 8.28 |

(11) 1-[trans-4-(2-carboxyethyl)cyclohexyl]-3-(7-ethyl-6,7,8,9-tetrahydro-5H-pyridazino[2,3-d]azepin-2-yl)-imidazolidin-2-one×2 HCl×0.9 H₂O Melting point: 283°–286° C.

$R_f$ value: 0.46 (Reversed Phase silica gel; methanol/5% aqueous saline solution=6:4).

| Calc.: | C | 52.36 | H | 7.35 | N | 13.88 | Cl | 14.05 |
|---|---|---|---|---|---|---|---|---|
| Found: | | 52.70 | | 7.44 | | 13.86 | | 14.01 |

(12) 1-[trans-4-(2-carboxyethyl)cyclohexyl]-3-(3-ethyl-2,3,4,5-tetrahydro-1H-3-benzazepin-7-yl)-3H-imidazol-2-one-hydrochloride×0.5 H₂O $R_f$ value: 0.38 (Reversed Phase silica gel; methanol/5% aqueous saline solution=6:4)

| Calc.: | C | 63.08 | H | 7.72 | N | 9.19 | Cl | 7.76 |
|---|---|---|---|---|---|---|---|---|
| Found: | | 63.26 | | 7.69 | | 9.28 | | 7.64 |

(13) 1-[trans-4-(2-carboxyethyl)cyclohexyl]-3-(2,3,4,5-tetrahydro-1H-3-benzazepin-7-yl)-hydantoin-hydrochloride $R_f$ value: 0.16 (silica gel; methylene chloride/methanol/conc. aqueous ammonia=80:20:2)

| Calc.: | C | 60.61 | H | 6.94 | N | 9.64 | Cl | 8.13 |
|---|---|---|---|---|---|---|---|---|
| Found: | | 60.34 | | 6.94 | | 9.58 | | 8.27 |

(14) 1-[trans-4-(2-carboxyethyl)cyclohexyl]-3-(2,3,4,5-tetrahydro-1H-3-benzazepin-7-yl)-3,4,5,6-tetrahydro-1H-pyrimidin-2-one×1.65 HCl×0.7 H₂O Melting point: 230°–235° C.

$R_f$ value: 0.40 (Reversed Phase silica gel/methanol/5% aqueous saline solution=6:4)

| Calc.: | C | 58.27 | H | 7.71 | N | 8.86 | Cl | 12.33 |
|---|---|---|---|---|---|---|---|---|
| Found: | | 58.04 | | 7.70 | | 8.82 | | 12.43 |

(15) 1-(2-carboxyethyl)-3-[4-(3-methyl-2,3,4,5-tetrahydro-1H-3-benzazepin-7-yl)phenyl]-imidazolidin-2-one-hydrochloride Melting point: >250° C.

$R_f$ value: 0.20 (Reversed Phase silica gel/methanol/5% aqueous saline soltuion=6:4)

(16) 1-[trans-4-(2-carboxyethyl)cyclohexyl]-3-(6,7,8,9-tetrahydro-5H-pyrimido[4,5-d]azepin-2-yl)-imidazolidin-2-one-hydrochloride $R_f$ value: 0.60 (Reversed Phase silica gel/methanol/5% aqueous saline solution=6:4)

(17) 1-[trans-4-(2-carboxyethyl)cyclohexyl]-3-(6,7,8,9-tetrahydro-5H-pyrazino[2,3-d]azepin-2-yl)-imidazolidin-2-one-hydrochloride

(18) 1-[trans-4-(2-carboxymethyl)cyclohexyl]-3-(6,7,8,9-tetrahydro-5H-pyrido[2,3-d]azepin-2-yl)-imidazolidin-2-one-hydrochloride

(19) 1-[trans-4-(2-carboxyethyl)cyclohexyl]-3-(1,2,3,4-tetrahydro-isoquinolin-6-yl)-imidazolidin-2-one-hydrochloride

(20) 1-[trans-4-(2-carboxyethyl)cyclohexyl]-3-(2,3-dimethyl-3,4-dihydroquinazolin-7-yl)-imidazolidin-2-one-hydrochloride

(21) 1-[trans-4-(2-carboxyethyl)cyclohexyl]-3-(3-ethyl-2,3,4,5-tetrahydro-1H-3-benzazepin-7-yl)-imidazolidin-2-one-hydrochloride Melting point: >270° C.

$R_f$ value: 0.35 (Reversed Phase silica gel/methanol/5% aqueous saline solution=6:4)

(22) 1-[trans-4-(2-carboxyethyl)cyclohexyl]-3-(3-propyl-2,3,4,5-tetrahydro-1H-3-benzazepin-7-yl)-imidazolidin-2-one×1.07 HCl×1 H₂O Melting point: >250° C.

$R_f$ value: 0.32 (Reversed Phase silica gel/methanol/5% aqueous saline solution=6:4)

| Calc.: | C | 61.96 | H | 8.33 | N | 8.67 | Cl | 7.83 |
|---|---|---|---|---|---|---|---|---|
| Found: | | 62.10 | | 8.14 | | 8.77 | | 7.94 |

(23) 1-[trans-4-(2-carboxyethyl)cyclohexyl]-3-(3-allyl-2,3,4,5-tetrahydro-1H-3-benzazepin-7-yl)-imidazolidin-2-one×1.1 HCl×1.5 H$_2$O Melting point: >250° C.

R$_f$ value: 0.30 (Reversed Phase silica gel/methanol/5% aqueous saline solution=6:4)

| Calc.: | C | 60.94 | H | 8.00 | N | 8.53 | Cl | 7.91 |
|---|---|---|---|---|---|---|---|---|
| Found: | | 61.32 | | 7.63 | | 8.47 | | 7.82 |

(24) 1-[trans-4-(2-carboxyethyl)cyclohexyl]-3-(3-isobutyl-2,3,4,5-tetrahydro-1H-3-benzazepin-7-yl)-imidazolidin-2-one-hydrochloride

(25) 1-[trans-4-(2-carboxyethyl)cyclohexyl]-3-[3-(2-hydroxyethyl)-2,3,4,5-tetrahydro-1H-3-benzazepin-7-yl]-imidazolidin-2-one-hydrochloride Melting point: 257°–260° C.

R$_f$ value: 0.46 (Reversed Phase silica gel/methanol/5% aqueous saline solution=6:4)

(26) 1-[trans-4-(2-carboxyethyl)cyclohexyl]-3-[3-(carboxymethyl)-2,3,4,5-tetrahydro-1H-3-benzazepin-7-yl]-imidazolidin-2-one-hydrochloride Melting point: >280° C.

R$_f$ value: 0.39 (Reversed Phase silica gel/methanol/5% aqueous saline solution=6:4)

(27) 1-[trans-4-(2-carboxyethyl)cyclohexyl]-3-(3-benzyl-2,3,4,5-tetrahydro-1H-3-benzazepin-7-yl)-imidazolidin-2-one-hydrochloride Melting point: >250° C.

R$_f$ value: 0.21 (Reversed Phase silica gel/methanol/5% aqueous saline solution=6:4)

(28) 1-[trans-4-(2-carboxyethyl)cyclohexyl]-3-[3-(cyclopropylmethyl)-2,3,4,5-tetrahydro-1H-3-benzazepin-7-yl]-imidazolidin-2-one-hydrochloride Melting point: >280° C.

R$_f$ value: 0.31 (Reversed Phase silica gel/methanol/5% aqueous saline solution=6:4)

(29) 1-[trans-4-(2-carboxyethyl)cyclohexyl]-3-(3-cyclopropyl-2,3,4,5-tetrahydro-1H-3-benzazepin-7-yl)-imidazolidin-2-one-hydrochloride

(30) 1-[trans-4-(2-carboxyethyl)cyclohexyl]-3-[3-(cyclohexylmethyl)-2,3,4,5-tetrahydro-1H-3-benzazepin-7-yl]-imidazolidin-2-one-hydrochloride

(31) 1-[trans-4-(2-carboxyethyl)cyclohexyl]-3-(3-cyclohexyl-2,3,4,5-tetrahydro-1H-3-benzazepin-7-yl)-imidazolidin-2-one-hydrochloride

EXAMPLE 10

1-[4-[2-(Methoxycarbonyl)ethyl]phenyl]-3-(2,3,4,5-tetrahydro-1H-3-benzazepin-7-yl)-imidazolidin-2-one-hydrochloride 2.3 g of 1-(3-tert.Butyloxycarbonyl-2,3,4,5-tetrahydro-1H-3-benzazepin-7-yl)-3-[4-[2-(methoxycarbonyl)ethyl]phenyl]-imidazolidin-2-one are stirred in 30 ml of methanolic hydrochloric acid for 2 hours at ambient temperature. The reaction mixture is evaporated down, the residue is stirred with ice water, suction filtered, washed with a little methanol and tert.butyl-methylether and then dried.

Yield: 1.8 g (90% of theory),

| Calc.: | C | 64.25 | H | 6.56 | N | 9.77 | Cl | 8.25 |
|---|---|---|---|---|---|---|---|---|
| Found: | | 64.08 | | 6.60 | | 9.92 | | 8.51 |

R$_f$ value: 0.26 (Reversed Phase silica gel; methanol/5% aqueous saline solution=6:4)

Mass spectrum: M$^+$=393

EXAMPLE 11

1-[(4aRS,6RS,8aRS)-1,2,3,4,4a,5,6,7,8,8a-Decahydroisoquinolin-6-yl]-3-[4-[2-(methoxycarbonyl)ethyl]phenyl]-imidazolidin-2-one-hydrochloride To 216 mg of 1-[4-[2-(methoxycarbonyl)ethyl]phenyl]-3-[(4aRS,6RS,8aRS)-2-methyl-1,2,3,4,4a,5,6,7,8,8a-decahydroisoquinolin-6-yl]-imidazolidin-2-one and 185 mg of 1,8-bis-(dimethylamino)-naphthaline in 5 ml of 1,2-dichloroethane are added 0.09 ml of 1-chloroethyl-chloroformate, the mixture is stirred for 20 minutes at ambient temperature and then refluxed for 2.5 hours. The reaction mixture is evaporated down, the residue is combined with 10 ml of methanol and refluxed for 3 hours. The reaction mixture is acidified with methanolic hydrochloric acid, evaporated down and purified by chromatography over a silica gel column using methylene chloride/methanol (92:8).

Yield: 200 mg (87% of theory),

R$_f$ value: 0.35 (Reversed Phase silica gel; methanol/5% aqueous saline solution=6:4)

EXAMPLE 12

1-[4-[2-(Methoxycarbonyl)ethyl]phenyl]-3-[(4aRS,6RS,8aRS)-2-methyl-1,2,3,4,4a,5,6,7,8,8a-decahydroisoquinolin-6-yl]-imidazolidin-2-one 950 mg of 1-[4-[2-(methoxycarbonyl)ethyl]phenyl]-3-[(4aRS,6RS,8aRS)-2-methyl-1,2,3,4,4a,5,6,7,8,8a-decahydroisoquinolin-6-yl]-3H-imidazol-2-one in 50 ml of ethyl acetate are hydrogenated in the presence of palladium on activated charcoal for 5 hours under a hydrogen pressure of 50 psi at ambient temperature and then for 5 hours at 50° C. The catalyst is filtered off and the filtrate is evaporated down. The residue is briefly heated with tert.butylmethylether, then cooled with stirring. The solid is suction filtered, washed with tert.butylmethylether and dried.

Yield: 300 mg (31% of theory),

Melting point: 155°–157° C.

R$_f$ value: 0.29 (Reversed Phase silica gel; methanol/5% aqueous saline solution=6:4)

The following compounds are obtained analogously to Example 12:

(1) 1-[trans-4-[2-(methoxycarbonyl)ethyl]cyclohexyl]-3-(3-trifluoroacetyl-2,3,4,5-tetrahydro-1H-3-benzazepin-7-yl)-imidazolidin-2-one Melting point: 165°–168° C.

R$_f$ value: 0.44 (silica gel; cyclohexane/ethyl acetate=1:1)

(2) 1-trans-4-[[(methoxycarbonyl)methyl]oxy]cyclohexyl]-3-(3-trifluoroacetyl-2,3,4,5-tetrahydro-1H-3-benzazepin-7-yl)-imidazolidin-2-one Melting point: 146°–147° C.

R$_f$ value: 0.62 (silica gel; ethyl acetate/cyclohexane=3:1)

(3) 1-[4-[2-(ethoxycarbonyl)-1-propyl]phenyl]-3-(3-trifluoroacetyl-2,3,4,5-tetrahydro-1H-3-benzazepin-7-yl)-3H-imidazolidin-2-one $R_f$ value: 0.32 (silica gel; cyclohexane/ethyl acetate=2:1)

(4) 1-[2-[4-(methoxycarbonyl)phenyl]ethyl]-3-(3-trifluoroacetyl-2,3,4,5-tetrahydro-1H-3-benzazepin-7-yl)-imidazolidin-2-one Melting point: 143°–144° C.

$R_f$ value: 0.46 (silica gel; cyclohexane/ethyl acetate=1:1)

(5) 1-[trans-4-[2-(methoxycarbonyl)ethyl]cyclohexyl]-3-(3-ethyl-2,3,4,5-tetrahydro-1H-3-benzazepin-7-yl)-imidazolidin-2-one-hydrochloride Melting point: from 230° C. (Decomp.)

$R_f$ value: 0.22 (Reversed Phase silica gel; methanol/5% aqueous saline solution=6:4)

(6) 1-[trans-4-[2-(methoxycarbonyl)ethyl]cyclohexyl]-3-(7-ethyl-6,7,8,9-tetrahydro-5H-pyrazino[2,3-d]azepin-2-yl)-imidazolidin-2-one Melting point: 136°–138° C.

$R_f$ value: 0.33 (silica gel; methylene chloride/methanol=9:1)

(7) 1-[4-[2-(ethoxycarbonyl)-1-phenyl-ethyl]phenyl]-3-(3-trifluoroacetyl-2,3,4,5-tetrahydro-1H-benzazepin-7-yl)-imidazolidin-2-one $R_f$ value: 0.22 (silica gel; cyclohexane/ethyl acetate=7:3)

EXAMPLE 13

1-[4-[2-(Methoxycarbonyl)ethyl]phenyl]-3-[(4aRS,6RS,8aRS)-2-methyl-1,2,3,4,4a,5,6,7,8,8a-decahydroisoquinolin-6-yl]-3H-imidazol-2-one To 6.9 g of (4aRS,6RS,8aRS)-6-[(2,2-dimethoxyethyl)amino]-2-methyl-1,2,3,4,4a,5,6,7,8,8a-decahydroisoquinoline in 30 ml of dioxane are added 6.4 g of 4-[2-(methoxycarbonyl)ethyl]-phenylisocyanate and the mixture is stirred for 2 hours at ambient temperature. The reaction mixture is evaporated down, taken up in 100 ml of methanol, mixed with methanolic hydrochloric acid and refluxed for 20 minutes. The reaction mixture is evaporated down and the residue is stirred with 200 ml of water. The precipitate is removed by suction filtering and the filtrate is extracted with ethyl acetate. The organic phase is discarded. The aqueous phase is made alkaline with potassium carbonate solution and extracted several times with ethyl acetate. The combined ethyl acetate extracts are washed once with saturated saline solution, dried and evaporated down. The crude product is purified by chromatography over an aluminium oxide column (basic) with ethyl acetate followed by trituration with tert.butylmethylether.

Yield: 1.03 g (9% of theory), $R_f$ value: 0.55 (silica gel; toluene/dioxane/methanol/conc. aqueous ammonia 20:50:20:5)

The following compounds are obtained analogously to Example 13:

(1) 1-[4-[2-(methoxycarbonyl)ethyl]phenyl]-3-[(4aRS,6SR,8aRS)-2-methyl-1,2,3,4,4a,5,6,7,8,8a-decahydroisoquinolin-6-yl]-3H-imidazol-2-one×0.3 water Melting point: 140°–145° C.

| Calc.: | C | 68.56 | H | 7.91 | N | 10.43 |
|---|---|---|---|---|---|---|
| Found: | | 68.49 | | 7.97 | | 10.51 |

(2) 1-[2-[4-(methoxycarbonyl)phenyl]ethyl]-3-(3-trifluoroacetyl-2,3,4,5-tetrahydro-1H-3-benzazepin-7-yl)-3H-imidazol-2-one Amine and isocyanate are stirred in dioxane first at ambient temperature and then over a steam bath. The treatment with methanolic hydrochloric acid is omitted. The [2-[4-(methoxycarbonyl)phenyl]ethyl]-isocyanate used is obtained by reacting the corresponding amine-hydrochloride with phosgene.

Melting point: 165°–167° C.

$R_f$ value: 0.31 (silica gel; cyclohexane/ethyl acetate=1:1).

EXAMPLE 14

4-[4-(Carboxyethyl)phenyl]-5-methyl-2-(2,3,4,5-tetrahydro-1H-3-benzazepin-7-yl)-4H-1,2,4-triazol-3-one-hydrochloride-hydrate 410 mg of 4-[4-[2-(methoxycarbonyl)ethyl]phenyl]-5-methyl-2-(3-trifluoroacetyl-2,3,4,5-tetrahydro-1H-3-benzazepin-7-yl)-4H-1,2,4-triazol-3-one are stirred with 10 ml glacial acetic acid and 10 ml of semiconcentrated hydrochloric acid for 7 hours at 90° C. After cooling, the mixture is evaporated down, the residue is stirred with water, suction filtered and washed with water and acetone.

Yield: 240 mg (57% of theory),

Melting point: >250° C.

$R_f$ value: 0.43 (Reversed Phase silica gel; methanol/5% aqueous saline solution=6:4)

| Calc.: | C | 59.12 | H | 6.09 | N | 12.53 | Cl | 7.93 |
|---|---|---|---|---|---|---|---|---|
| Found: | | 58.96 | | 6.13 | | 12.31 | | 7.74 |

The following compounds are obtained analogously to Example 14:

(1) 1-[trans-4-(2-carboxyethyl)cyclohexyl]-3-(2,3,4,5-tetrahydro-1H-3-benzazepin-7-yl)-imidazolidin-2-one-hydrochloride Melting point: >250° C.

$R_f$ value: 0.46 (Reversed Phase silica gel; methanol/5% aqueous saline solution=6:4)

| Calc.: | C | 62.62 | H | 7.64 | N | 9.98 | Cl | 8.40 |
|---|---|---|---|---|---|---|---|---|
| Found: | | 62.24 | | 7.67 | | 10.01 | | 8.86 |

(2) 1-[trans-4-(2-carboxyethyl)cyclohexyl]-3-(1,2,3,4,5,6-hexahydro-3-benzazocin-8-yl)-imidazolidin-2-one-hydrochloride (3) 2-[4-(2-carboxyethyl)phenyl]-4-(2,3,4,5-tetrahydro-1H-3-benzazepin-7-yl)-4H-1,2,4-triazol-3-one-hydrochloride (4) 4-[4-(2-carboxyethyl)phenyl]-5-phenyl-2-(2,3,4,5-tetrahydro-1H-3-benzazepin-7-yl)-4H-1,2,4-triazol-3-one-hydrochloride (5) 4-[4-(2-carboxyethyl)phenyl]-2-(2,3,4,5-tetrahydro-1H-3-benzazepin-7-yl)-5-trifluoromethyl-4H-1,2,4-triazol-3-one-hydrochloride (6) 1-[4-(2-carboxyethyl)phenyl]-3-(2,3,4,5-tetrahydro-1H-3-benzazepin-7-yl)-3,4,5,6-tetrahydro-1H-pyrimidin-2-one-hydrochloride (7) 4-[4-(2-carboxyethyl)phenyl]-5-ethyl-2-(2,3,4,5-tetrahydro-1H-3-benzazepin-7-yl)-4H-1,2,4-triazol-3-one-hydrochloride (8) 5-[4-(2-carboxyethyl)phenyl]-4-methyl-2-(2,3,4,5-tetrahydro-1H-3-benzazepin-7-yl)-4H-1,2,4-triazol-3-one-hydrochloride (9) 4-[4-(2-carboxyethyl)phenyl]-3-methyl-1-(1,2,3,4-tetrahydroisoquinolin-6-yl)-imidazolidin-2-one-hydrochloride

(10) 2-[trans-4-(2-carboxyethyl)cyclohexyl]-4-(2,3,4,5-tetrahydro-1H-3-benzazepin-7-yl)-2H,4H-1,2,4-triazol-3,5-dione-hydrochloride

(11) 1-[3-(2-carboxyethyl)phenyl]-3-(2,3,4,5-tetrahydro-1H-3-benzazepin-7-yl)-imidazolidin-2-one-hydrochloride
(12) 1-[4-(carboxymethyl)phenyl]-3-(2,3,4,5-tetrahydro-1H-3-benzazepin-7-yl)-imidazolidin-2-one-hydrochloride
(13) 2-[trans-4-(2-carboxyethyl)cyclohexyl]-5-(2,3,4,5-tetrahydro-1H-3-benzazepin-7-yl)-3,4-dihydro-2H,5H-1,2,5-thiadiazol-1,1-dioxide $R_f$ value: 0.50 (Reversed phase silica gel; methanol/5% aqueous saline solution=6:4)

(14) 1-[4-(2-carboxy-1-octyl)phenyl]-3-(2,3,4,5-tetrahydro-1H-3-benzazepin-7-yl)-imidazolidin-2-one-hydrochloride
(15) 2-[trans-4-(2-carboxyethyl)cyclohexyl]-4-(2,3,4,5-tetrahydro-1H-3-benzazepin-7-yl)-1-methyl-2H,4H-1,2,4-triazol-3,5-dione-hydrochloride
(16) 1-[4-(3-carboxypropyl)phenyl]-3-(2,3,4,5-tetrahydro-1H-3-benzazepin-7-yl)-imidazolidin-2-one-hydrochloride
(17) 1-(5-carboxypentyl)-3-(2,3,4,5-tetrahydro-1H-3-benzazepin-7-yl)-imidazolidin-2-one-hydrochloride
(18) 1-[4-(2-carboxyethyl)-2-fluorophenyl]-3-(2,3,4,5-tetrahydro-1H-3-benzazepin-7-yl)-imidazolidin-2-one-hydrochloride
(19) 1-[4-(2-carboxyethyl)-3-methyl-phenyl]-3-(2,3,4,5-tetrahydro-1H-3-benzazepin-7-yl)-imidazolidin-2-one-hydrochloride
(20) 1-[trans-4-[(carboxymethyl)oxy]cyclohexyl]-3-(2,3,4,5-tetrahydro-1H-3-benzazepin-7-yl)-imidazolidin-2-one-hydrochloride Melting point: 316°–317° C. (Decomp.)

$R_f$ value: 0.66 (Reversed Phase silica gel; methanol/5% aqueous saline solution=6:4)

| Calc.: | C | 59.50 | H | 7.13 | N | 9.91 | Cl | 8.36 |
| --- | --- | --- | --- | --- | --- | --- | --- | --- |
| Found: |   | 59.26 |   | 7.13 |   | 9.94 |   | 8.44 |

(21) 1-[4-(trans-2-carboxyethenyl)phenyl]-3-(2,3,4,5-tetrahydro-1H-3-benzazepin-7-yl)-imidazolidin-2-one-hydrochloride $R_f$ value: 0.64 (Reversed Phase silica gel; methanol/5% aqueous saline solution=6:4)

Mass spectrum: $M^+=377$

(22) 1-[4-(2-carboxy-1-propyl)phenyl]-3-(2,3,4,5-tetrahydro-1H-3-benzazepin-7-yl)-imidazolidin-2-one-hydrochloride×H$_2$O $R_f$ value: 0.34 (Reversed Phase silica gel; methanol/5% aqueous saline solution=6:4)

| Calc.: | C | 61.66 | H | 6.71 | N | 9.38 | Cl | 7.91 |
| --- | --- | --- | --- | --- | --- | --- | --- | --- |
| Found: |   | 61.56 |   | 6.75 |   | 9.30 |   | 8.14 |

(23) 1-trans-4-(2-carboxyethyl)cyclohexyl]-3-(2,3,4,5-tetrahydro-1H-3-benzazepin-7-yl)-3H-imidazol-2-one-hydrochloride
(24) 1-[trans-4-(2-carboxyethyl)cyclohexyl]-3-(2,3,4,5-tetrahydro-1H-2-benzazepin-7-yl)-imidazolidin-2-one-hydrochloride
(25) 2-[trans-4-(2-carboxyethyl)cyclohexyl]-4-(2,3,4,5-tetrahydro-1H-3-benzazepin-7-yl)-4H-1,2,4-triazol-3-one-hydrochloride 2N hydrochloric acid and as starting material: the compound of example 18(1) are used.

Melting point: >220° C.

$R_f$ value: 0.50 (Reversed Phase silica gel; methanol/5% aqueous saline solution=6:4)

| Calc.: | C | 59.92 | H | 6.94 | N | 13.31 | Cl | 8.42 |
| --- | --- | --- | --- | --- | --- | --- | --- | --- |
| Found: |   | 60.03 |   | 6.99 |   | 13.32 |   | 8.46 |

(26) 2-[trans-4-(2-carboxyethyl)cyclohexyl]-4-(2,3,4,5-tetrahydro-1H-3-benzazepin-7-yl)-5-methyl-4H-1,2,4-triazol-3-one-hydrochloride
(27) 2-[trans-4-(2-carboxyethyl)cyclohexyl]-4-(2,3,4,5-tetrahydro-1H-3-benzazepin-7-yl)-5-phenyl-4H-1,2,4-triazol-3-one-hydrochloride
(28) 4-[trans-4-(2-carboxyethyl)cyclohexyl]-2-(2,3,4,5-tetrahydro-1H-3-benzazepin-7-yl)-4H-1,2,4-triazol-3-one-hydrochloride Melting point: >240° C.

$R_f$ value: 0.64 (Reversed Phase silica gel; methanol/5% aqueous saline solution=6:4)

(29) 4-[trans-4-(2-carboxyethyl)cyclohexyl]-2-(2,3,4,5-tetrahydro-1H-3-benzazepin-7-yl)-5-methyl-4H-1,2,4-triazol-3-one-hydrochloride $R_f$ value: 0.48 (Reversed Phase silica gel; methanol/5% aqueous saline solution=6:4)

| Calc.: | C | 60.75 | H | 7.18 | N | 12.88 | Cl | 8.15 |
| --- | --- | --- | --- | --- | --- | --- | --- | --- |
| Found: |   | 60.54 |   | 7.26 |   | 12.68 |   | 8.54 |

(30) 4-[trans-4-(2-carboxyethyl)cyclohexyl]-2-(2,3,4,5-tetrahydro-1H-3-benzazepin-7-yl)-5-phenyl-4H-1,2,4-triazol-3-one-hydrochloride
(31) 1-[4-(2-carboxy-1-phenyl-ethyl)phenyl]-3-(2,3,4,5-tetrahydro-1H-3-benzazepin-7-yl)-imidazolidin-2-one-hydrochloride $R_f$ value: 0.31 (Reversed Phase silica gel; methanol/5% aqueous saline solution=6:4)

(32) 1-[1-(2-carboxyethyl)piperidin-4-yl]-3-(2,3,4,5-tetrahydro-1H-3-benzazepin-7-yl)-imidazolidin-2-one-hydrochloride
(33) 1-(trans-4-carboxycyclohexyl)-3-[2-(2,3,4,5-tetrahydro-1H-3-benzazepin-7-yl)ethyl]-imidazolidin-2-one-hydrochloride
(34) 1-[2-(4-carboxyphenyl)ethyl]-3-(2,3,4,5-tetrahydro-1H-3-benzazepin-7-yl)-imidazolidin-2-one-hydrochloride×H$_2$O $R_f$ value: 0.40 (Reversed Phase silica gel; methanol/5% aqueous saline solution=6:4)

Mass spectrum: $M^+=379$

| Calc.: | C | 60.89 | H | 6.50 | N | 9.68 | Cl | 8.17 |
| --- | --- | --- | --- | --- | --- | --- | --- | --- |
| Found: |   | 60.57 |   | 6.62 |   | 9.77 |   | 8.22 |

EXAMPLE 15

4(4-[2-(Methoxycarbonyl)ethyl]phenyl]-5-methyl-2-(3-trifluoroacetyl-2,3,4,5-tetrahydro-1H-3-benzazepin-7-yl)-4H-1,2,4-triazol-3-one 1.6 g of 7-iodo-3-trifluoroacetyl-2,3,4,5-tetrahydro-1H-3-benzazepine, 1.1 g of 4-[4-[2-(methoxycarbonyl)ethyl]phenyl]-5-methyl-4H-1,2,4-triazol-3-one, 0.19 ml of tris-[2-(2-methoxyethoxy)-ethyl]-amine, 130 mg of copper(I) chloride, 130 mg of copper(I)iodide and 1.1 g of potassium carbonate are refluxed for 2 hours in 30 ml of dimethylformamide. After cooling, the mixture is evaporated down and the residue is divided between water and methylene chloride. The solid is suction filtered, the organic phase is separated off, washed with water, dried, filtered and evaporated down. The residue is purified by chromatography over a silica gel column using cyclohexane/ethyl acetate=1:1.

Yield: 340 mg (16% of theory),

Melting point: 160°–162° C.

$R_f$ value: 0.51 (silica gel; cyclohexane/ethyl acetate=1:1)

The following compounds are obtained analogously to Example 15:

(1) 4-[trans-4-[2-(methoxycarbonyl)ethyl]cyclohexyl]-2-(3-trifluoroacetyl-2,3,4,5-tetrahydro-1H-3-benzazepin-7-yl)-5-methyl-4H-1,2,4-triazol-3-one Melting point: 175°–177° C.

$R_f$ value: 0.50 (silica gel; methylene chloride/ethyl acetate=90:10)

(2) 4-[trans-4-[2-(methoxycarbonyl)ethyl]cyclohexyl]-2-(3-trifluoroacetyl-2,3,4,5-tetrahydro-1H-3-benzazepin-7-yl)-4H-1,2,4-triazol-3-one $R_f$ value: 0.40 (silica gel; methylene chloride/methanol=100:1)

EXAMPLE 16

1-[trans-4-[2-(Methoxycarbonyl)ethyl]cyclohexyl]-3-(3-trifluoroacetyl-2,3,4,5-tetrahydro-1H-3-benzazepin-7-yl)-hydantoin To 4.1 g of (3-trifluoroacetyl-2,3,4,5-tetrahydro-1H-3-benzazepin-7-yl)-isocyanate and 3.7 g of methyl [[trans-4-[2-(methoxycarbonyl)-ethyl]cyclohexyl]amino]-acetate-hydrochloride in 50 ml of acetonitrile are added 3.2 ml of N-ethyl-diisopropylamine and the mixture is stirred for 2½ days at ambient temperature. The reaction mixture is evaporated down, the residue is taken up in ethyl acetate and washed with water and saline solution. The organic phase is dried and evaporated down and the residue is crystallised with a little methanol in an ice bath. The product is suction filtered, washed with cold methanol and dried.

Yield: 4.1 g (56% of theory),

Melting point: 118°–120° C.

$R_f$ value 0.85 (silica gel; ethyl acetate)

EXAMPLE 17

1-[trans-4-[2-(Isopropoxycarbonyl)ethyl] cyclohexyl]-3-(3-propyl-2,3,4,5-tetrahydro-1H-3-benzazepin-7-yl)-imidazolidin-2-one-hydrochloride 230 mg of 1-[trans-4-[2- isopropoxycarbonyl)ethyl] cyclohexyl]-3-(3-allyl-2,3,4,5-tetrahydro-1H-3-benzazepin-7-yl)-imidazolidin-2-one-hydrochloride are hydrogenated in 10 ml of isopropanol at 30° C. under a hydrogen pressure of 50 psi in the presence of 50 mg of 10% palladium on activated charcoal for 6 hours. The catalyst is suction filtered and the filtrate is evaporated down.

Yield: 240 mg, $R_f$ value 0.55 (silica gel; methylene chloride/methanol/conc. aqueous ammonia=95:5:1)

EXAMPLE 18

2-[trans-4-[2-(Methoxycarbonyl)ethyl]cyclohexyl]-5-(3-trifluoroacetyl-2,3,4,5-tetrahydro-1H-3-benzazepin-7-yl)-3,4-dihydro-2H,5H-1,2,5-thiadiazol-1,1-dioxide To 1.25 g of 2-(3-trifluoroacetyl-2,3,4,5-tetrahydro-1H-3-benzazepin-7-yl)-3,4-dihydro-2H,5H-1,2,5-thiadiazol -1,1-dioxide, 0.64 g of methyl 3-(cis-4-hydroxycyclohexyl) propionate [$R_f$ value: 0.58 (silica gel; cyclohexane/ethyl acetate=1:1); isolated from the cis/trans mixture by chromatography over a silica gel column using cyclohexane/ethyl acetate (1:1)] and 0.90 g triphenylphosphine in 2 ml of acetonitrile, are added 0.54 ml of diethyl azodicarboxylate. A further 1.5 g of methyl 3-(cis-4-hydroxycyclohexyl) propionate and a mixture of 0.90 g of triphenylphosphine and 0.54 ml of diethyl azodicarboxylate in 2 ml of acetonitrile are added. After 30 minutes stirring at ambient temperature, a mixture of 0.90 g of triphenylphosphine and 0.54 ml of diethyl azodicarboxylate is added once more. After stirring at ambient temperature overnight, the mixture is evaporated down and the residue is purified by chromatography over a silica gel column with cyclohexane/ethyl acetate/methylene chloride (1:1:1).

Yield: 700 mg (38% of theory),

Melting point: 169°–173° C.

$R_f$ value: 0.61 (silica gel; cyclohexane/ethyl acetate/methylene chloride=1:1:1)

The following compound is obtained analogously to example 18:

(1)-2[trans-4-[2-(Methoxycarbonyl)ethyl]cyclohexyl]-4-(3-tert.butyloxycarbonyl-2,3,4,5-tetrahydro-1H-3-benzazepine-7-yl)-4H-1,2,4-triazol-3-one Melting point: 162°–164° C.

$R_f$ value: 0.43 (silica gel; cyclohexane/ethyl acetate/methylene chloride=1:1:1)

EXAMPLE 19

1-[trans-4-(2-Carboxyethyl)cyclohexyl]-3-(3-methyl- 2,3,4,5-tetrahydro-1H-3-benzazepin-7-yl)-imidazolidin-2-one-hydrochloride To a mixture of 5.0 g of 1-[trans-4-(2-carboxyethyl) cyclohexyl]-3-(2,3,4,5-tetrahydro-1H-3-benzazepin-7-yl)-imidazolidin-2-one-hydrochloride, 4.5 ml of formic acid, 3.6 ml of 37% aqueous formaldehyde and 20 ml of water are added 2.0 g of sodium hydrogen carbonate, whilst cooling with ice, and the mixture is then heated to 65° C. After 8 hours it is cooled, stirred overnight and the mixture is evaporated down. The residue is stirred with water and evaporated down once again. Then the residue is stirred with water once more and adjusted to a pH of 1 using hydrochloric acid. It is evaporated down, the residue is stirred with a little water and suction filtered. The filter cake is stirred with acetone, the product is suction filtered, washed with acetone and dried in vacuo.

Yield: 3.7 g (71% of theory),

Melting point: 292°–295° C. (Decomp.)

$R_f$ value: 0.38 (Reversed Phase silica gel; methanol/5% aqueous saline solution=6:4)

The following compounds are obtained analogously to Example 19:

(1) 1-[trans-4-[(carboxymethyl)oxy]cyclohexyl]-3-(3-methyl-2,3,4,5-tetrahydro-1H-3-benzazepin-7-yl)-imidazolidin-2-one-hydrochloride×NaCl×0.5 $H_2O$ $R_f$ value: 0.62 (Reversed Phase silica gel; methanol/5% aqueous saline solution=6:4)

| Calc.: | C | 52.28 | H | 6.58 | N | 8.31 | Cl | 13.49 |
|---|---|---|---|---|---|---|---|---|
| Found: | | 52.28 | | 6.68 | | 8.33 | | 14.03 |

(2) 1-[4-(2-carboxy-1-propyl)phenyl]-3-(3-methyl-2,3,4,5-tetrahydro-1H-3-benzazepin-7-yl)-imidazolidin-2-one-hydrochloride×0.5 H₂O R_f value: 0.29 (Reversed Phase silica gel; methanol/5% aqueous saline solution=6:4)

| Calc.: | C | 63.63 | H | 6.90 | N | 9.28 | Cl | 7.83 |
|---|---|---|---|---|---|---|---|---|
| Found: |  | 63.32 |  | 6.99 |  | 9.32 |  | 7.81 |

(3) 3-[trans-4-(2-carboxyethyl)cyclohexyl]-1-(3-methyl-2,3,4,5-tetrahydro-1H-3-benzazepin-7-yl)-hydantoin-hydrochloride Melting point: >250° C.

R_f value: 0.32 (Reversed Phase silica gel; methanol/5% aqueous saline solution=6:4)

| Calc.: | C | 61.39 | H | 7.17 | N | 9.34 | Cl | 7.88 |
|---|---|---|---|---|---|---|---|---|
| Found: |  | 61.39 |  | 7.25 |  | 9.37 |  | 7.92 |

(4) 1-[trans-4-(2-carboxyethyl)cyclohexyl]-3-(3-methyl-2,3,4,5-tetrahydro-1H-3-benzazepin-7-yl)-hydantoin-hydrochloride R_f value: 0.37 (silica gel; methylene chloride/methanol/conc. aqueous ammonia=80:20:2)

| Calc.: | C | 61.39 | H | 7.17 | N | 9.34 | Cl | 7.88 |
|---|---|---|---|---|---|---|---|---|
| Found: |  | 61.11 |  | 7.26 |  | 9.36 |  | 7.86 |

(5) 2-[trans-4-(2-carboxyethyl)cyclohexyl]-4-(3-methyl-2,3,4,5-tetrahydro-1H-3-benzazepin-7-yl)-1-methyl-2H,4H-1,2,4-triazol-3,5-dione-hydrochloride (6) 2-[trans-4-(2-carboxyethyl)cyclohexyl]-4-(3-methyl-2,3,4,5-tetrahydro-1H-3-benzazepin-7-yl)-4H-1,2,4-triazol-3-one-hydrochloride×1,1 water Melting point: >220° C.

R_f value: 0.48 (Reversed phase silica gel; methanol/5% aqueous saline solution=6.4))

| Calc.: | C | 58.10 | H | 7.36 | N | 12.32 | Cl | 7.80 |
|---|---|---|---|---|---|---|---|---|
| Found: |  | 58.07 |  | 7.36 |  | 12.28 |  | 7.83 |

(7) 2-[trans-4-(2-carboxyethyl)cyclohexyl]-4-(3-methyl-2,3,4,5-tetrahydro-1H-3-benzazepin-7-yl)-5-methyl-4H-1,2,4-triazol-3-one-hydrochloride (8) 2-[trans-4-(2-carboxyethyl)cyclohexyl]-4-(3-methyl-2,3,4,5-tetrahydro-1H-3-benzazepin-7-yl)-5-phenyl-4H-1,2,4-triazol-3-one-hydrochloride (9) 4-[trans-4-(2-carboxyethyl)cyclohexyl]-2-(3-methyl-2,3,4,5-tetrahydro-1H-3-benzazepin-7-yl)-4H-1,2,4-triazol-3-one-hydrochloride

(10) 4-[trans-4-(2-carboxyethyl)cyclohexyl]-2-(3-methyl-2,3,4,5-tetrahydro-1H-3-benzazepin-7-yl)-5-methyl-4H-1,2,4-triazol-3-one×1.1 HCl×0.2 H₂O Melting point: 238°–240° C.

R_f value: 0.37 (Reversed Phase silica gel; methanol/5% aqueous saline solution=6:4)

| Calc.: | C | 60.55 | H | 7.40 | N | 12.28 | Cl | 8.55 |
|---|---|---|---|---|---|---|---|---|
| Found: |  | 60.68 |  | 7.53 |  | 12.31 |  | 8.36 |

(11) 4-[trans-4-(2-carboxyethyl)cyclohexyl]-2-(3-methyl-2,3,4,5-tetrahydro-1H-3-benzazepin-7-yl)-5-phenyl-4H-1,2,4-triazol-3-one-hydrochloride

(12) 1-[trans-4-(2-carboxyethyl)cyclohexyl]-3-(3-methyl-2,3,4,5-tetrahydro-1H-3-benzazepin-7-yl)-3,4,5,6-tetrahydro-1H-pyrimidin-2-one×1.05 HCl×0.3 H₂O Melting point: 237°–240° C.

R_f value: 0.37 (Reversed Phase silica gel; methanol/5% aqueous saline solution=6:4)

| Calc.: | C | 63.04 | H | 8.07 | N | 9.18 | Cl | 8.14 |
|---|---|---|---|---|---|---|---|---|
| Found: |  | 62.97 |  | 8.05 |  | 9.15 |  | 8.16 |

(13) 1-[4-(2-carboxy-1-phenyl-ethyl)phenyl]-3-(3-methyl-2,3,4,5-tetrahydro-1H-3-benzazepin-7-yl)-imidazolidin-2-one-hydrochloride

(14) 1-[1-(2-carboxyethyl)piperidin-4-yl]-3-(3-methyl-2,3,4,5-tetrahydro-1H-3-benzazepin-7-yl)-imidazolidin-2-one-hydrochloride

(15) 1-(trans-4-carboxycyclohexyl)-3-[2-(3-methyl-2,3,4,5-tetrahydro-1H-3-benzazepin-7-yl)ethyl]-imidazolidin-2-one-hydrochloride

(16) 1-[2-(4-carboxyphenyl)ethyl]-3-(3-methyl-2,3,4,5-tetrahydro-1H-3-benzazepin-7-yl)-imidazolidin-2-one-hydrochloride

(17) 1-[trans-4-(2-carboxyethyl)cyclohexyl]-3-(7-methyl-6,7,8,9-tetrahydro-5H-pyrimido[4,5-d]azepin-2-yl)-imidazolidin-2-one-hydrochloride R_f value: 0.56 (Reversed phase silica gel; methanol/5% aqueous saline solution=6.4)

Mass spectrum: M⁺=401

(18) 1-[trans-4-(2-carboxyethyl)cyclohexyl]-3-(7-methyl-6,7,8,9-tetrahydro-5H-pyrazino[2,3-d]azepin-2-yl)-imidazolidin-2-one-hydrochloride

(19) 1-[trans-4-(2-carboxyethyl)cyclohexyl]-3-(7-methyl-6,7,8,9-tetrahydro-5H-pyrido[2,3-d]azepin-2-yl)-imidazolidin-2-one-hydrochloride

(20) 1-[trans-4-(2-carboxyethyl)cyclohexyl]-3-(2-methyl-1,2,3,4-tetrahydro-isoquinolin-6-yl)-imidazolidin-2-one-hydrochloride

(21) 1-[trans-4-(2-carboxyethyl)cyclohexyl]-3-(2-methyl-2,3,4,5-tetrahydro-1H-2-benzazepin-7-yl)-imidazolidin-2-one-hydrochloride

(22) 1-[trans-4-(2-carboxethyl)cyclohexyl]-3-(3-methyl-1,2,3,4,5,6-hexahydro-3-benzazocin-8-yl)-imidazolidin-2-one-hydrochloride

(23) 2-[trans-4-(2-carboxyethyl)cyclohexyl]-4-(3-methyl-2,3,4,5-tetrahydro-1H-3-benzazepin-7-yl)-2H,4H-1,2,4-triazol-3,5-dione-hydrochloride

EXAMPLE 20

1-(3-Ethyl-2,3,4,5-tetrahydro-1H-3-benzazepin-7-yl)-3-[4-[2-(methoxycarbonyl)ethyl]phenyl-imidazolidin-2-one 600 mg of 1-[4-[2-(methoxycarbonyl)ethyl)phenyl]-3-(2,3,4,5-tetrahydro-1H-3-benzazepin-7-yl)-imidazolidin-2-one-hydrochloride and 128 mg of sodium hydride (55% in paraffin oil) are treated in 15 ml of dimethylformamide in an ultrasound bath for 2.5 hours. 125 μl of ethyliodide are added and the mixture is treated for a further 2.5 hours. The reaction mixture is combined with 50 ml of water, the precipitate is suction filtered, washed with water and dried. The crude product is purified by chromatography over a silica gel column using methylene chloride/methanol/conc. aqueous ammonia (9:1:0.1).

Yield: 260 mg (44% of theory),

Melting point: 168°–170° C.

R_f value: 0.45 (silica gel; methylene chloride/methanol/conc. aqueous ammonia=4:1:0,2)

The following compounds are obtained analogously to Example 20:

(1) 1-(3-butyl-2,3,4,5-tetrahydro-1H-3-benzazepin-7-yl) -3-[4-[2-(methoxycarbonyl)ethyl]phenyl]-imidazolidin-2-one $R_f$ value: 0.64 (silica gel; methylene chloride/methanol/ conc. aqueous ammonia=4:1:0.2)

(2) 1-[trans-4-[2-(isopropoxycarbonyl)ethyl]cyclohexyl]-3-(3-allyl-2,3,4,5-tetrahydro-1H-3-benzazepin-7-yl)-imidazolidin-2-one-hydrochloride Carried out with allylbromide/N-ethyl-diisopropylamine in acetonitrile $R_f$ value: 0.63 (silica gel; methylene chloride/methanol/ conc. aqueous ammonia=95:5:1)

(3) 1-[trans-4-[2-(methoxycarbonyl)ethyl]cyclohexyl]-3-(3-benzyl-2,3,4,5-tetrahydro-1H-3-benzazepin-7-yl)-imidazolidin-2-one-hydrochloride $R_f$ value: 0.30 (silica gel; methylene chloride/methanol=95:5)

(4) 1-[trans-4-[2-(methoxycarbonyl)ethyl]cyclohexyl]-3-(3-benzyl-2,3,4,5-tetrahydro-1H-3-benzazepin-7-yl)-imidazolidin-2-one-hydrojodide Acetonitrile and cyclopropylmethylbromide in the presence of sodium jodide and N-ethyl-diisopropylamine are used.

Melting point: 225°–230° C. (decomp.)

$R_f$ value: 0.72 (silica gel; methylene chloride/methanol/ conc. aqueous ammonia=90:10:2)

(5) 1-[trans-4-[2-(methoxycarbonyl)ethyl]cyclohexyl]-3-(2-hydroxyethyl)-2,3,4,5-tetrahydro-1H-3-benzazepin-7-yl)-imidazolidin-2-one-hydrojodide Acetonitrile and 2-bromoethanol in the presence of sodium jodide and N-ethyl-diisopropylamine are used.

Melting point: >200° C.

$R_f$ value: 0.55 (silica gel; methylene chloride/methanol/ conc. aqueous ammonia=90:10:2)

(6) 1-[trans-4-[2-(methoxycarbonyl)ethyl]cyclohexyl]-3-(methoxycarbonylmethyl)-2,3,4,5-tetrahydro-1H-3-benzazepin-7-yl)-imidazolidin-2-one Acetonitrile and 2-bromoacetate in the presence of sodium jodide and N-ethyl-diisopropylamine are used.

Melting point: 127°–129° C.

$R_f$ value: 0.28 (Reversed phase silica gel; methanol/5% aqueous saline solution=6:4)

EXAMPLE 21

3-[trans-4-[2-(Methoxycarbonyl)ethyl)cyclohexyl]-1-(2,3,4,5-tetrahydro-1H-3-benzazepin-7-yl)-hydantoin-hydrochloride Hydrochloric acid gas is passed for 10 minutes over 920 mg of 3-[trans-4-[2-(methoxycarbonyl)ethyl]-cyclohexyl]-1-(3-trifluoroacetyl-2,3,4,5-tetrahydro-1H-3-benzazepin-7-yl)-hydantoin in 50 ml methanol and the mixture is then refluxed for 5 hours. It is cooled, the product is suction filtered, washed with methanol and diethylether and dried at 80° C.

Yield: 770 mg (95% of theory),

Melting point: >250° C.

$R_f$ value: 0.23 (Reversed Phase silica gel; methanol/5% aqueous saline solution=6:4)

The following compounds are obtained analogously to Example 21:

(1) 1-[trans-4-[2-(methoxycarbonyl)ethyl]cyclohexyl]-3-(2,3,4,5-tetrahydro-1H-3-benzazepin-7-yl)-hydantoin-hydrochloride Melting point: >250° C.

$R_f$ value: 0.43 (Reversed Phase silica gel; methanol/5% aqueous saline solution=6:4)

| Calc.: | C | 61.39 | H | 7.17 | N | 9.34 | Cl | 7.88 |
|---|---|---|---|---|---|---|---|---|
| Found: |   | 61.10 |   | 7.21 |   | 9.29 |   | 8.03 |

(2) 1-[trans-4-[2-(methoxycarbonyl)ethyl]cyclohexyl]-3-(2,3,4,5-tetrahydro-1H-3-benzazepin-7-yl)-3,4,5,6-tetrahydro-1H-pyrimidin-2-one-hydrochloride $R_f$ value: 0.31 (Reversed Phase silica gel; methanol/5% aqueous saline solution=6:4)

EXAMPLE 22

3-[trans-4-[2-(Methoxycarbonyl)ethyl]cyclohexyl]-1-(3-trifluoroacetyl-2,3,415-tetrahydro-1H-3-benzazepin-7-yl)-hydantoin 40 mg of potassium tert.butoxide are added to 2.1 g of N-[trans-4-[2-(methoxycarbonyl)ethyl]cyclohexyl]-N'-[(benzyloxycarbonyl)methyl]-N'-(3-trifluoroacetyl-2,3,4,5-tetrahydro-1H-3-benzazepin-7-yl)-urea in 25 ml of boiling toluene and the mixture is refluxed for 30 minutes. The reaction mixture is cooled, stirred with a few drops of glacial acetic acid, evaporated down and purified by chromatography over a silica gel column using cyclohexane/ethyl acetate (8:2 to 7:3) and crystallised from methanol.

Yield: 0.95 g (55% of theory),

Melting point: 132°–134° C.

$R_f$ value: 0.59 (silica gel; cyclohexane/ethyl acetate=1:1)

EXAMPLE 23

1-[trans-4-[2-(Methoxycarbonyl)ethyl]cyclohexyl]-3-(6,7,8,9-tetrahydro-5H-pyrimido[4,5-d]azepin-2-yl)-imidazolidin-2-one 1.0 g of 1-[trans-4-[2-(methoxycarbonyl)ethyl]-cyclohexyl]-3-(7-benzyl-6,7,8,9-tetrahydro-5H-pyrimido[4,5-d]azepin-2-yl)-3H-imidazol-2-one are hydrogenated in 15 ml of methanol in the presence of 500 mg of palladium on activated charcoal (10% palladium) for 17 hours at ambient temperature under a hydrogen pressure of 50 psi. The catalyst is filtered off and the filtrate is evaporated down. The residue is used directly to prepare the compound of Example 9(16).

$R_f$ value: 0.44 (Reversed Phase silica gel; methanol/5% aqueous saline solution=6:4)

The following compound is obtained analogously to Example 23:

(1) 1-[trans-4-[2-(methoxycarbonyl)ethyl]cyclohexyl]-3-(6,7,8,9-tetrahydro-5H-pyrido[2,3-d]azepin-2-yl)-imidazolidin-2-one-hydrochloride.

EXAMPLE 24

1-2-(Ethoxycarbonyl)ethyl]-3-[4-(3-methyl-2,3,4,5-tetrahydro-1H-3-benzazepin-7-yl)phenyl]-imidazolidin-2-one 3.1 g of (3-methyl-2,3,4,5-tetrahydro-1H-3-benzazepin-7-yl)-boric acid, 4.1 g of 1-[2-(ethoxycarbonyl)ethyl]-3-[4-(trifluoromethylsulfonyloxy)phenyl]-imidazolidin-2-one, 3.5 g tetrakis(triphenylphosphine)-palladium and 6.5 ml of triethylamine are stirred in 25 ml of dimethylformamide under nitrogen for 4 hours at 100° C. The reaction mixture is cooled, evaporated in vacuo and the obtained residue dissolved in methylene chloride. The mixture is filtered over siliceous earth, the filtrate evaporated and the obtained residue is purified by chromatography over a silica gel column with methylene chloride/methanol (100:7).

Yield: 2.7 g (63% of theory), $R_f$ value: 0.31 (silica gel; methylene chloride/methanol= 100:7)

EXAMPLE 25

Dry ampoule containing 2.5 mg of active substance per 1 ml
Composition

| | |
|---|---|
| Active substance | 2.5 mg |
| Mannitol | 50.0 mg |
| Water for injections ad | 1.0 ml |

Preparation

The active substance and mannitol are dissolved in water. After transferring the solution to the ampoule, it is freeze-dried.

At the point of use, the solution is made up with water for injections.

EXAMPLE 26

Dry ampoule containing 35 mg of active substance per 2 ml
Composition

| | |
|---|---|
| Active substance | 35.0 mg |
| Mannitol | 100.0 mg |
| Water for injections ad | 2.0 ml |

Preparation

The active substance and mannitol are dissolved in water. After transferring the solution to the ampoule, it is freeze-dried.

At the point of use, the solution is made up with water for injections.

EXAMPLE 27

Tablet containing 50 mg of active substance
Composition

| | |
|---|---|
| (1) Active substance | 50.0 mg |
| (2) Lactose | 98.0 mg |
| (3) Corn starch | 50.0 mg |
| (4) Polyvinylpyrrolidone | 15.0 mg |
| (5) Magnesium stearate | 2.0 mg |
| | 215.0 mg |

Preparation (1), (2) and (3) are mixed together and granulated with an aqueous solution of (4). (5) is added to the dried granules. From this mixture, compressed tablets are produced, biplanar, facetted on both sides and notched on one side. Diameter of tablets: 9 mm.

EXAMPLE 28

Tablet containing 350 mg of active substance
Composition

| | |
|---|---|
| (1) Active substance | 350.0 mg |
| (2) Lactose | 136.0 mg |
| (3) Corn starch | 80.0 mg |
| (4) Polyvinylpyrrolidone | 30.0 mg |
| (5) Magnesium stearate | 4.0 mg |
| | 600.0 mg |

Preparation (1), (2) and (3) are mixed together and granulated with an aqueous solution of (4). (5) is added to the dried granules. From this mixture, compressed tablets are produced, biplanar, facetted on both sides and notched on one side. Diameter of tablets: 12 mm.

EXAMPLE 29

Capsules containing 50 mg of active substance
Composition

| | |
|---|---|
| (1) Active substance | 50.0 mg |
| (2) Dried corn starch | 58.0 mg |
| (3) Powdered lactose | 50.0 mg |
| (4) Magnesium stearate | 2.0 mg |
| | 160.0 mg |

Preparation (1) is triturated with (3). This triturate is added to the mixture of (2) and (4), with thorough mixing.

This powdered mixture is packed into size 3 hard gelatin oblong capsules in a capsule filling machine.

EXAMPLE 30

Capsules containing 350 mg of active substance
Composition

| | |
|---|---|
| (1) Active substance | 350.0 mg |
| (2) Dried corn starch | 46.0 mg |
| (3) Powdered lactose | 30.0 mg |
| (4) Magnesium stearate | 4.0 mg |
| | 430.0 mg |

Preparation (1) is triturated with (3). This triturate is added to the mixture of (2) and (4), with thorough mixing.

This powdered mixture is packed into size 0 hard gelatin oblong capsules in a capsule filling machine.

The invention also relates to benzazepine derivatives of the general formula (XXI)

the tautomers thereof, the stereoisomers thereof including the mixtures thereof and the salts thereof, in particular the physiologically tolerated salts thereof with inorganic or organic acids or bases, which have valuable pharmacological properties, preferably aggregation-inhibiting effects, to pharmaceuticals containing these compounds, to the use thereof and to processes for their preparation.

In the above general formula XXI, R is a hydrogen atom, a methyl, ethyl or benzyl group, $X_1$, $X_2$ and $X_3$, which can be identical or different, are each a methine group or a nitrogen atom, it being necessary, however, for at least one of the radicals $X_1$, $X_2$ or $X_3$ to be a nitrogen atom, A' is a —$CH_2CH_2$—, —CH=CH—, —N=CH— or —CH=N— group which is optionally substituted by a methyl group, a —$CH_2CO$— or —$COCH_2$— group which is optionally substituted by one or two methyl groups, D' is a 1,4-cyclohexylene, 1,4-phenylene or 1,4-piperidinylene group, it being necessary for the nitrogen atom of the 1,4-piperidinylene group to be linked to the radical E', E' is a —$CH_2CH_2$— group which is optionally substituted by a methyl group, or an —$OCH_2$— group, it being necessary for the oxygen atom of the —$OCH_2$— group to be linked to a carbon atom of the radical D', and J is a carboxyl or $C_{1-4}$-alkoxycarbonyl group.

Preferred compounds of the above general formula (XXI) are, however, those in which R is a hydrogen atom, a methyl, ethyl or benzyl group, $X_1$, $X_2$ and $X_3$, which can be identical or different, are each a methine group or a nitrogen atom, it being necessary, however, for at least one of the radicals $X_1$, $X_2$ or $X_3$ to be a nitrogen atom, A' is a —$CH_2CH_2$—, —CH=CH—, —N=CH— or —CH=N— group which is optionally substituted by a methyl group, a —$CH_2CO$— or —$COCH_2$— group which is optionally substituted by one or two methyl groups, D' is a 1,4-cyclohexylene, 1,4-phenylene or 1,4-piperidinylene group, it being necessary for the nitrogen atom of the 1,4-piperidinylene group to be linked to the radical E', E' is a —$CH_2CH_2$— group which is optionally substituted by a methyl group, or an —$OCH_2$— group, it being necessary for the oxygen atom of the —$OCH_2$— group to be linked to a carbon atom of the radical D', and J is a carboxyl or $C_{1-4}$-alkoxycarbonyl group, the tautomers thereof, the stereoisomers and salts thereof.

Particularly preferred compounds of the above general formula XXI are, however, those in which R is a hydrogen atom, a methyl, ethyl or benzyl group, $X_1$ is a nitrogen atom, and $X_2$ and $X_3$ are each a methine group or $X_2$ is a nitrogen atom, and $X_1$ and $X_3$ are each a methine group or $X_3$ is a nitrogen atom, and $X_1$ and $X_2$ are each a methine group or $X_1$ and $X_3$ are each a nitrogen atom, and $X_2$ is a methine group, A' is a —$CH_2CH_2$— or —CH=CH— group which is optionally substituted by a methyl group, or a —$CH_2CO$— group, it being necessary for the methylene group of the —$CH_2CO$— group to be linked to the nitrogen atom which is connected to the adjacent heteroaromatic ring, D' is a 1,4-cyclohexylene, 1,4-phenylene or 1,4-piperidinylene group, it being necessary for the nitrogen atom of the 1,4-piperidinylene group to be linked to the radical E', E' is a —$CH_2CH_2$— group which is optionally substituted by a methyl group, or an —$OCH_2$— group, it being necessary for the oxygen atom of the —$OCH_2$— group to be linked to a carbon atom of the radical D', and J is a carboxyl or $C_{1-2}$-alkoxycarbonyl group, the tautomers thereof, the stereoisomers and salts thereof.

Very particularly preferred compounds of the general formula XXI are those in which R is a hydrogen atom, a methyl, ethyl or benzyl group, $X_1$ and $X_3$ are each a nitrogen atom, and $X_2$ is a methine group, A' is a —$CH_2CH_2$— or —CH=CH— group which is optionally substituted by a methyl group, or a —$CH_2CO$— group, it being necessary for the methylene group of the —$CH_2CO$— group to be linked to the nitrogen atom which is connected to the adjacent heteroaromatic ring, D' is a 1,4-cyclohexylene, 1,4-phenylene or 1,4-piperidinylene group, it being necessary for the nitrogen atom of the 1,4-piperidinylene group to be linked to the radical E', E' is a —$CH_2CH_2$— group which is optionally substituted by a methyl group, or an —$OCH_2$— group, it being necessary for the oxygen atom of the —$OCH_2$— group to be linked to a carbon atom of the radical D', and J is a carboxyl or $C_{1-2}$-alkoxycarbonyl group, the tautomers thereof, the stereoisomers and salts thereof.

Examples of particularly preferred compounds which may be mentioned are the following:

(a) 1-[trans-4-(2-carboxyethyl)cyclohexyl]-3-(7-methyl-6,7,8,9-tetrahydro-5H-pyrazino[2,3-d]azepin-2-yl)-imidazolidin-2-one and (b) 3-[trans-4-(2-carboxyethyl)cyclohexyl]-1-(7-methyl-6,7,8,9-tetrahydro-5H-pyrazino[2,3-d]azepin-2-yl) imidazolidin-2,4-dione and the salts thereof.

The novel compounds of the general formula XXI are obtained according to the invention for example by the following processes:

a) To prepare compounds of the general formula (XXI) in which J is a carboxyl group:

Conversion of a compound of the general formula

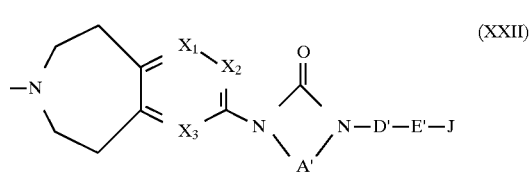

(XXII)

in which

A', D', E', R and $X_1$ to $X_3$ are as defined at the outset, and

J' is a group which can be converted into a carboxyl group by hydrolysis, treatment with acids, thermolysis or hydrogenolysis, into a compound of the general formula XXI in which J is a carboxyl group.

It is possible, for example, for functional derivatives of the carboxyl group, such as unsubstituted or substituted amides, esters, thioesters, trimethylsilyl esters, orthoesters, imino esters, amidines or anhydrides thereof, or the cyano group to be converted by hydrolysis into a carboxyl group, for esters with tertiary alcohols, for example the tertbutyl ester, to be converted by treatment with an acid or thermolysis into a carboxyl group and for esters with aralkanols, for example the benzyl ester, to be converted by hydrogenolysis into a carboxyl group.

The hydrolysis is expediently carried out either in the presence of an acid such as hydrochloric acid, sulfuric acid, phosphoric acid, acetic acid, trichloroacetic acid, trifluoroacetic acid or mixtures thereof or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane at temperatures between −10° and 120° C., for example at temperatures between room temperature and the boiling point of the reaction mixture.

If J' in a compound of the formula (XXII) is a cyano or aminocarbonyl group, these groups can also be converted with a nitrite, for example sodium nitrite, in the presence of an acid such as sulfuric acid, the latter expediently also being used as solvent, at temperatures between 0° and 50° C. into the carboxyl group.

If J' in a compound of the formula XXII is, for example the tert-butyloxycarbonyl group, the tert-butyl group can also be eliminated by treatment with an acid such as trifluoroacetic acid, formic acid, p-toluenesulfonic acid, sulfuric acid, hydrochloric acid, phosphoric acid or polyphosphoric acid, where appropriate in an inert solvent such as methylene chloride, chloroform, benzene, toluene, diethyl ether, tetrahydrofuran or dioxane, preferably at temperatures between −10° and 120° C., for example at temperatures between 0° and 60° C., or else thermally, where appropriate in an inert solvent such as methylene chloride, chloroform, benzene, toluene, tetrahydrofuran or dioxane and preferably in the presence of a catalytic amount of an acid such as p-toluenesulfonic acid, sulfuric acid, phosphoric acid or polyphosphoric acid, preferably at the boiling point of the solvent used, for example at temperatures between 40° and 120° C. With the abovementioned reaction conditions it is possible where appropriate for N-tert-butyloxycarbonylamino or N-butyloxycarbonylimino groups which are present to be converted into the corresponding amino or imino groups.

If J' in a compound of the formula XXII is, for example, the benzyloxycarbonyl group, the benzyl group can also be eliminated by hydrogenolysis in the presence of a hydrogenation catalyst such as palladium/carbon in a suitable solvent such as methanol, ethanol, ethanol/water, glacial acetic acid, ethyl acetate, dioxane or dimethylformamide, preferably at temperatures between 0° and 50° C., for example at room temperature, under a pressure of 1 to 5 bar of hydrogen.

b) To prepare compounds of the general formula XXI in which A is an ethylene group which is optionally substituted by a methyl group:

Cyclization of a compound of the general formula

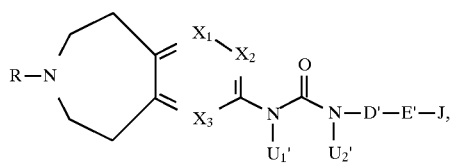

in which D', E', J, R and $X_1$ to $X_3$ are as defined at the outset, one of the radicals $U_1'$ or $U_2'$ is a hydrogen atom and the other of the radicals $U_1'$ or $U_2'$ is an ethylene group which is optionally substituted by a methyl group and to whose terminals a nucleophilic leaving group such as a halogen atom, a hydroxyl or sulfonic ester group, for example a chlorine, bromine or iodine atom, a hydroxyl, methanesulfonyloxy or p-toluenesulfonyloxy group, is bonded.

The reaction is preferably carried out in a solvent such as methylene chloride, acetonitrile, tetrahydrofuran, toluene, dimethylformamide or dimethyl sulfoxide, where appropriate in the presence of a base such as sodium hydride, potassium carbonate, potassium tert-butoxide or N-ethyldiisopropylamine or, where appropriate, in the presence of a dehydrating agent such as triphenylphosphine/diethyl azodicarboxylate at temperatures between −20° and 100° C., preferably at temperatures between 0° and 60° C.

c) To prepare compounds of the general formula XXI in which A' is an ethylene group which is optionally substituted by a methyl group:

Hydrogenation of a compound of the general formula

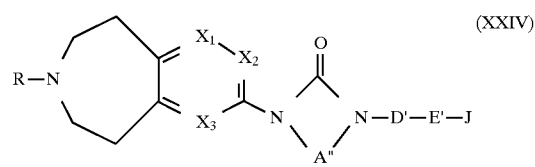

in which

D', E', J, R and $X_1$ to $X_3$ are as defined at the outset, and A" is an ethylene group which is optionally substituted by a methyl group.

The hydrogenation is preferably carried out with hydrogen in the presence of a catalyst such as palladium/carbon or platinum in, a solvent such as methanol, ethanol, ethyl acetate or glacial acetic acid, where appropriate with the addition of an acid such as hydrochloric acid or with the addition of a salt of acetic acid such as the potassium salt, at temperatures between 0° and 100° C., but preferably at temperatures between room temperature and 60° C., and under a pressure of 1 to 7 bar, but preferably 3 to 5 bar, of hydrogen. If an employed compound of the general formula IV contains an N-benzyl or O-benzyl group, this can simultaneously be converted into a hydrogen atom during the hydrogenation.

d) To prepare compounds of the general formula XXI in which A' is an ethylene group which is optionally substituted by a methyl group:

Cyclization of a compound, which is formed where appropriate in the reaction mixture, of the general formula

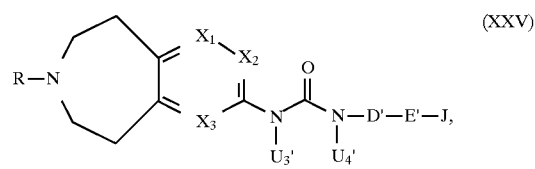

in which

D', E', J, R and $X_1$ to $X_3$ are as defined at the outset, one of the radicals $U_3'$ or $U_4'$ is a hydrogen atom and the other of the radicals $U_3'$ or $U_4'$ is an ethylene group which is optionally substituted by a methyl group and in which two terminal hydrogen atoms are each replaced by a $C_{1-3}$-alkoxy group.

The reaction is preferably carried out in a solvent such as methanol, ethanol, isopropanol, methylene chloride, acetonitrile, tetrahydrofuran or toluene, preferably in the presence of an acid such as hydrochloric acid, acetic acid, trifluoroacetic acid, sulfuric acid or p-toluenesulfonic acid at temperatures between −20° and 200° C., preferably at temperatures between 0° and 160° C.

e) To prepare compounds of the general formula XXI in which R is a methyl, ethyl or benzyl group:

Reaction of a compound of the general formula

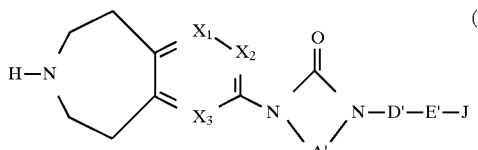

(XXVI)

in which

A', D', J, E' and $X_1$ to $X_3$ are as defined at the outset, with a compound of the general formula

 (XXVII)

in which $R_1$' is a methyl, ethyl or benzyl group and $Z_1$' is a nucleophilic leaving group such as a halogen atom, for example a chlorine, bromine or iodine atom, or a sulfonic ester group, for example a methanesulfonyloxy or p-toluenesulfonyloxy group, or $Z_1$' is, together with an adjacent hydrogen atom of the radical $R_1$', an oxygen atom.

The alkylation with a compound of the formula XXVII in which $Z_1$' is a nucleophilic leaving group is expediently carried out in a solvent such as acetonitrile, methylene chloride, acetone, tetrahydrofuran, dioxane, dimethyl sulfoxide or dimethylformamide, where appropriate in the presence of a base such as sodium carbonate, potassium carbonate or sodium hydroxide solution or in the presence of a tertiary organic base such as N-ethyldiisopropylamine or N-methylmorpholine, which can simultaneously act as solvents, at temperatures between –30° and 150° C., but preferably at temperatures between 20° and 120° C.

The reductive alkylation with a carbonyl compound of the general formula XXVII is carried out in the presence of a complex metal hydride such as sodium borohydride, lithium borohydride or sodium cyanoborohydride, expediently at a pH of 6–7 and at room temperature or in the presence of a hydrogenation catalyst, for example with hydrogen in the presence of palladium/carbon, under a pressure of 1 to 5 bar of hydrogen. The methylation is, however, preferably carried out in the presence of formic acid as reducing agent at elevated temperatures, for example at temperatures between 60° and 120° C.

f) To prepare compounds of the general formula XXI in which A' is a —$CH_2CO$— or —$COCH_2$— group which is optionally substituted by one or two methyl groups:

Cyclization of a compound, which is formed where appropriate in the reaction mixture, of the general formula

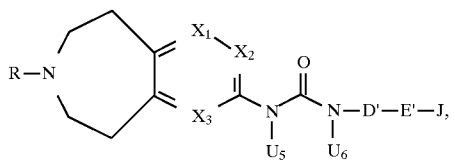

(XXVIII)

in which

D', E', J, R and $X_1$ to $X_3$ are as defined at the outset, one of the radicals $U_5$ or $U_6$ is a hydrogen atom and the other of the radicals $U_5$ or $U_6$ is an ethylene group which is optionally substituted by a methyl group and in which one terminal methylene group is replaced by a $Z_2$'—CO— group, where $Z_2$' is a nucleophilic leaving group such as a halogen atom, a hydroxyl, alkoxy, aryloxy or arylalkoxy group, for example a chlorine or bromine atom, a hydroxyl, methoxy, ethoxy, phenoxy, or benzyloxy group.

The reaction is preferably carried out in a solvent such as acetonitrile, tetrahydrofuran, toluene, chlorobenzene, dioxane, dimethylformamide or dimethyl sulfoxide, where appropriate in the presence of a base such as sodium hydride, potassium carbonate, potassium tert-butoxide or N-ethyldiisopropylamine or where appropriate in the presence of a dehydrating agent such as triphenylphosphine/diethyl azodicarboxylate, dicyclohexylcarbodiimide or N,N'-carbonyldiimidazole at temperatures between –20° and 200° C., preferably at temperatures between 0° and 160° C.

g) To prepare compounds of the general formula XXI in which D' is a 1,4-piperidinylene group and E' is an ethylene group which is optionally substituted by a methyl group:

Alkylation of a compound of the general formula

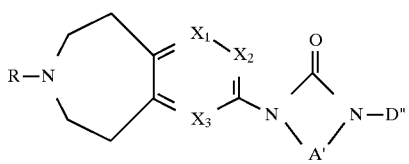

(XXXI)

in which

A', R and $X_1$ to $X_3$ are as defined at the outset, and D" is a 4-piperidinyl group, with a compound of the general formula

 (XXXII)

or with a compound of the general formula

 (XXXIII)

in which

J is defined as at the outset,

E" is an ethylene group which is optionally substituted by a methyl group,

E'" is an ethylene group which is optionally substituted by a methyl group and $Z_3$' is a nucleophilic leaving group such as a halogen atom, a hydroxyl or sulfonic ester group, for example a chlorine, bromine or iodine atom, a hydroxyl, methanesulfonyloxy or p-toluenesulfonyloxy group.

The reaction is preferably carried out in a solvent such as methanol, ethanol, methylene chloride, tetrahydrofuran, toluene, dioxane, dimethyl sulfoxide or dimethylformamide, where appropriate in the presence of an inorganic or a tertiary organic base or where appropriate in the presence of a dehydrating agent at temperatures between –30° and 200° C.

The reaction with a compound of the general formula XXXII in which $Z_3$' is a nucleophilic leaving group is preferably carried out in a solvent such as methylene chloride, acetonitrile, tetrahydrofuran, toluene, dimethylformamide or dimethyl sulfoxide, where appropriate in the presence of a base such as sodium hydride, potassium carbonate, potassium tert-butoxide or N-ethyl diisopropylamine at temperatures between –20° and 180° C., preferably at temperatures between 20° and 120 ° C.

The reaction with a compound of the general formula XXXIII is preferably carried out in a solvent such as methanol, ethanol, methylene chloride, tetrahydrofuran, toluene, dioxane, dimethyl sulfoxide or dimethylformamide at temperatures between –20° and 180° C., but preferably at temperatures between 20° and 120° C.

h) To prepare compounds of the general formula XXI in which J is a $C_{1-4}$-alkoxycarbonyl group:

Reaction of a carboxylic acid of the general formula

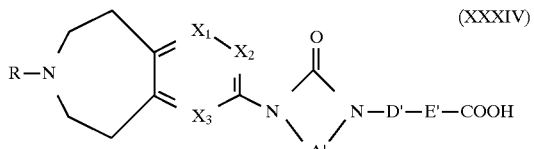
(XXXIV)

in which

D', E', R and $X_1$ to $X_3$ are as defined at the outset, or the reactive derivatives thereof, which are prepared where appropriate in the reaction mixture, with an alcohol of the general formula

HO—$R_2'$, (XXXV)

in which $R_2'$ is an alkyl group having 1 to 4 carbon atoms.

Examples of suitable reactive derivatives of a compound of the general formula XXXIV are the acid chlorides, acid azides, mixed anhydrides with aliphatic or aromatic carboxylic acids or carbonic monoesters thereof, the imidazolides thereof and the esters thereof such as the alkyl, aryl and aralkyl esters thereof, such as the methyl, ethyl, isopropyl, pentyl, phenyl, nitrophenyl or benzyl ester.

The reaction of a carboxyl compound is carried out where appropriate in a solvent or mixture of solvents, such as methylene chloride, dimethylformamide, benzene, toluene, chlorobenzene, tetrahydrofuran, benzene/tetrahydrofuran or dioxane or, particularly advantageously, in an appropriate alcohol of the general formula XXXV, where appropriate in the presence of an acid such as hydrochloric acid or in the presence of a dehydrating agent, for example in the presence of isobutyl chloroformate, thionyl chloride, trimethyl chlorosilane, sulfuric acid, methanesulfonic acid, p-toluenesulfonic acid, phosphorus trichloride, phosphorus pentoxide, N,N'-dicyclohexylcarbodiimide, N,N'-dicyclohexylcarbodiimide/N-hydroxysuccinimide or 1-hydroxybenzotriazol and, where appropriate, additionally in the presence of 4-dimethylaminopyridine, N,N'-carbonyldiimidazole or triphenylphosphine/tetrachloromethane, expediently at temperatures between 0° and 150° C., preferably at temperatures between 0° and 80° C.

The reaction of a corresponding alkoxycarbonyl compound with an alcohol of the general formula XXXV is preferably carried out in an appropriate alcohol as solvent, where appropriate in the presence of another solvent such as methylene chloride or ether, preferably in the presence of an-acid such as hydrochloric acid, at temperatures between 0° and 150° C., preferably at temperatures between 50° and 100° C.

If a compound of the general formula XXI which contains an unsaturated carbon-carbon bond is obtained according to the invention, this can be converted by catalytic hydrogenation into a corresponding saturated compound of the general formula XXI.

The catalytic hydrogenation preferably takes place with hydrogen in the presence of a catalyst such as palladium/carbon in a solvent such as methanol, ethanol, ethyl acetate or glacial acetic acid, where appropriate with the addition of an acid such as hydrochloric acid, at temperatures between 0° and 100° C., but preferably at temperatures of between 20° and 60° C., and under a pressure of 1 to 7 bar, but preferably 3 to 5 bar, of hydrogen.

In the reactions described above, reactive groups which are present where appropriate, such as imino groups, can be protected during the reaction by conventional protective groups which are eliminated again after the reaction.

A suitable protective radical for an imino group is, for example, the formyl, acetyl, trifluoroacetyl, ethoxycarbonyl, tert-butoxycarbonyl, benzyloxycarbonyl, benzyl, methoxybenzyl, 2,4-dimethoxybenzyl or methyl group.

The subsequent elimination where appropriate of a protective radical which has been used takes place, for example, by hydrolysis in an aqueous solvent, for example in water, isopropanol/water, acetic acid/water, tetrahydrofuran/water or dioxane/water, in the presence of an acid such as trifluoroacetic acid, hydrochloric acid or sulfuric acid or in the presence of an alkali metal base such as sodium hydroxide or potassium hydroxide, or by ether cleavage, for example in the presence of iodotrimethylsilane, at temperatures between 0° and 120° C. preferably at temperatures between 10° and 100° C.

However, the elimination of a benzyl, methoxybenzyl or benzyloxycarbonyl radical takes place, for example, by hydrogenolysis, for example with hydrogen in the presence of a catalyst such as palladium/carbon in a solvent such as methanol, ethanol, ethyl acetate or glacial acetic acid, where appropriate with the addition of an acid such as hydrochloric acid at temperatures between 0° and 100° C., but preferably at temperatures between 20° and 60° C., and under a pressure of 1 to 7 bar, but preferably 3 to 5 bar, of hydrogen. However, the elimination of a 2,4-dimethoxybenzyl radical preferably takes place in trifluoroacetic acid in the presence of anisole.

The elimination of a tert-butyl or tert-butyloxycarbonyl radical preferably takes place by treatment with an acid such as trifluoroacetic acid or hydrochloric acid or by treatment with iodotrimethylsilane, where appropriate using a solvent such as methylene chloride, dioxane, methanol or ether.

The elimination of a trifluoroacetyl radical preferably takes place by treatment with an acid such as hydrochloric acid, where appropriate in the presence of a solvent such as acetic acid or methanol, at temperatures between 50° and 120° C. or by treatment with sodium hydroxide solution, where appropriate in the presence of a solvent such as tetrahydrofuran or methanol at temperatures between 0° and 50° C.

The elimination of a methyl group from a methylimino group preferably takes place in the presence of 1-chloroalkyl chloroformates such as 1-chloroethyl chloroformate, preferably in the presence of a base such as 1,8-bis (dimethylamino)naphthalene in the presence of a solvent such as methylene chloride, 1,2-dichloroethane, toluene or dioxane at temperatures between 0° and 150° C., preferably at temperatures between 20° C. and the boiling point of the reaction mixture, and subsequent treatment with an alcohol such as methanol at temperatures between 20° C. and the boiling point of the alcohol used.

It is furthermore possible for the resulting compounds of the general formula XXI, as has already been mentioned at the outset, to be fractionated into their enantiomers and/or diastereomers. Thus, for example, cis/trans mixtures can be fractionated into their cis and trans isomers, and compounds with at least one optically active carbon atom can be fractionated into their enantiomers.

Thus, for example, the resulting cis/trans mixtures can be fractionated by chromatography into their cis and trans isomers, the resulting compounds of the general formula XXI which occur as racemates can be fractionated by methods known per se (see Allinger N. L. and Eliel E. L. in "Topics in Stereochemistry", Vol. 6, Wiley Interscience, 1971) into their optical antipodes, and compounds of the general formula XXI with at least two asymmetric carbon atoms can be fractionated on the basis of their physicochemical differences by methods known per se, for example by chromatography and/or fractional crystallization, into their diastereomers which, if they result in racemic form, can subsequently be separated into the enantiomers as mentioned above.

The enantiomer separation preferably takes place by column separation on chiral phases or by recrystallization from an optically active solvent or by reaction with an optically active substance which forms salts or derivatives such as, for example, esters or amides with the racemic compound, in particular acids and their activated derivatives or alcohols, and separation of the mixture of diastereomeric salts or the derivative obtained in this way, for example on the basis of different solubilities, it being possible to liberate the free antipodes from the pure diastereomeric salts or derivatives by the action of suitable agents. Examples of particularly useful optically active acids are the D and L forms of tartaric acid or dibenzoyltartaric acid, di-o-tolyltartaric acid, malic acid, mandelic acid, camphorsulfonic acid, glutamic acid, aspartic acid or quinic acid. A suitable optically active alcohol is, for example, (+)- or (−)-menthol, and a suitable optically active acyl radical in amides is, for example, (+)- or (−)-menthyloxycarbonyl.

It is furthermore possible for the resulting compounds of the formula XXI to be converted into their salts, in particular for pharmaceutical use into their physiologically tolerated salts with inorganic or organic acids. Examples of acids suitable for this purpose are hydrochloric acid, hydrobromic acid, methanesulfonic acid, sulfuric acid, phosphoric acid, fumaric acid, succinic acid, lactic acid, citric acid, tartaric acid or maleic acid.

In addition, the novel compounds of the formula XXI obtained in this way, if they contain a carboxyl group, can if required subsequently be converted into their salts with organic or inorganic bases, in particular for pharmaceutical use into their physiologically tolerated salts. Examples of bases suitable for this purpose are sodium hydroxide, potassium hydroxide, arginine, cyclohexylamine, ethanolamine, diethanolamine and triethanolamine.

Some of the compounds used as starting materials are known from the literature or are obtained by processes known from the literature (see examples).

Thus, for example, "The Organic Chemistry of Heterocyclic Compounds", Volume 37, by C. Temple, Jr., published by John Wiley & Sons, 1981, describes in chapters 13, 14 and 19 the preparation of corresponding triazole compounds.

Houben-Weyl, "Methoden der Organischen Chemie", Volume E4, by H. Hagemann, Georg Thieme Verlag, 1983, describes, for example, from page 368 the preparation of corresponding cyclic urea compounds. In addition, the same volume also describes from page 355, for example, the preparation of corresponding open-chain urea compounds which are required where appropriate as starting compounds.

Thus, for example, an appropriate cyclic urea derivative is obtained by cyclization of an appropriately substituted urea which in turn is obtained by reaction of an appropriate amine with an appropriate isocyanate, or by reaction of an appropriately subsituted diamine with a carbonic acid derivative such as phosgene, or an appropriate triazolone derivative by cyclization of an appropriate semicarbazide which in turn is obtained by reaction of an appropriate isocyanate with an appropriate hydrazide.

An ester group which is present where appropriate in the cyclic starting compounds obtained in this way or already in the starting compounds necessary for their preparation can be converted by hydrolysis into a carboxyl group, or a carboxyl group which is present where appropriate can be converted into an ester group.

As already mentioned at the outset, the novel benzazepine derivatives of the general formula XXI and the salts thereof, in particular the physiologically tolerated salts thereof with organic or inorganic acids or bases, have valuable properties. Thus, the novel compounds of the general formula I have valuable pharmacological properties, besides an antiinflammatory and antiosteoclastic effect in particular antithrombotic, antiaggregatory and tumor- and metastasis-inhibiting effects.

For example, the compounds of the general formula XXI were investigated for their biological effects as follows:

A. Inhibition of the binding of $^3$H-BIBU 52 to human platelets

A suspension of human platelets in plasma is incubated with $^3$H-BIBU 52[=(3S,5S)-5-[(4'-amidino-4-biphenylyl)oxymethyl]-3-[(carboxy)methyl]-2-pyrrolidinone[3-$^3$H-4-biphenylyl]], which replaces the ligand $^{125}$I-fibrinogen which is disclosed in the literature (see DE-A-4-,214.245), and various concentrations of the substance to be tested. The free and bound ligand is separated by centrifugation and determined quantitatively by scintillation counting. The inhibition of $^3$H-BIBU 52 binding by the test substance is determined from the measurements.

For this purpose, donor blood is taken from an antecubital vein and anticoagulated with trisodium citrate (final concentration 13 mM). The blood is centrifuged at 170×g for 10 minutes, and the supernatant platelet-rich plasma (PRP) is removed. The remaining blood is thoroughly centrifuged once again to obtain plasma. The PRP is diluted 1:10 with autologous plasma. 750 ml are incubated with 50 ml of physiological saline, 100 ml of test substance solution, 50 ml of $^{14}$C-sucrose (3700 Bq) and 50 ml of $^3$H-BIBU 52 (final concentration: 5 nM) at room temperature for 20 minutes. To measure the nonspecific binding, 5 ml of BIBU 52 (final concentration: 30 mM) are used in place of the test substance. The samples are centrifuged at 10000×g for 20 seconds, and the supernatant is aspirated off. 100 ml thereof are measured to determine the free ligand. The pellet is dissolved in 500 ml of 0.2N NaOH, and 450 ml are mixed with 2 ml of scintillator and 25 ml of 5N HCl and measured. The remaining plasma still present in the pellet is determined from the $^{14}$C content, and the bound ligand is determined from the $^3$H measurement. After subtraction of the nonspecific binding, the activity in the pellet is plotted against the concentration of test substance, and the concentration for 50% inhibition of binding is found.

B. Antithrombotic effect

Method

Platelet aggregation is measured by the method of Born and Cross (J. Physiol. 170, 397 (1964)) in platelet-rich plasma from healthy test subjects. For anticoagulation, sodium citrate 3.14% is added to the blood in the ratio 1:10 by volume.

Collagen-induced aggregation

The course of the decrease in optical density of the platelet suspension is measured and recorded photometrically after addition of the aggregation-inducing substance. The rate of aggregation is established from the angle of inclination of the density plot. The point on the plot at which the transmission of light is a maximum is used to calculate the optical density.

The amount of collagen is chosen to be as small as possible but sufficient for the reaction plot to have an irreversible course. The collagen commercially obtainable from Hormonchemie, Munich, is used.

Before the addition of collagen the plasma is in each case incubated with the substance at 37° C. for 10 minutes.

An $EC_{50}$ which relates to a 50% change in the optical density in the sense of inhibition of aggregation is determined graphically from the measured results.

The following table contains the results found:

| Substance (Example No). | Fibrinogen binding assay $IC_{50}$ [nM] | Inhibition of platelet aggregation $EC_{50}$ [nM] |
| --- | --- | --- |
| 32 | 11 | 100 |
| 32 (3) | 15 | 81 |
| 32 (1) | 250 | 310 |
| 32 (2) | 1000 | 2300 |
| 35 (1) | 17 | 110 |
| 36 (1) | 77 | 290 |
| 36 (2) | 19 | 210 |
| 36 (3) | 18 | 71 |
| 32 (6) | 31 | 230 |
| 36 (10) | 32 | 130 |
| 36 (12) | 13 | 450 |

Because of their inhibitory effect on cell-cell and cell-matrix interactions, the novel cyclic urea derivatives of the general formula XXI and their physiologically tolerated salts are suitable for controlling or preventing diseases in which smaller or larger cell aggregates occur or cell-matrix interactions are involved, for example in the control or prevention of venous and arterial thromboses, of cerebrovascular disorders, of pulmonary embolisms, of myocardial infarct, of arteriosclerosis, of osteoporosis and of metastasis of tumors and the therapy of genetically determined or else acquired disturbances of the interactions of cells with one another or with solid structures. The latter are furthermore suitable for concomitant therapy during thrombolysis with fibrinolytics or vascular interventions such as transluminal angioplasty or else in the therapy of states of shock, of psoriasis, of diabetes and of inflammations.

The dose for controlling or preventing the abovementioned disorders is between 0.1 mg and 30 mg/kg of bodyweight, preferably 1 mg to 15 mg/kg of bodyweight, with up to 4 doses a day. For this purpose, the compounds of the formula XXI prepared according to the invention can be incorporated into conventional pharmaceutical formulations such as tablets, coated tablets, capsules, powders, suspensions, solutions, sprays or suppositories, where appropriate in combination with other active substances such as thromboxane receptor antagonists and thromboxane synthesis inhibitors or combinations thereof, serotonin antagonists, α-receptor antagonists, alkyl nitrates such as glycerol trinitrate, phosphodiesterase inhibitors, prostacycline and analogs thereof, fibrinolytics such as tPA, prourokinase, urokinase, streptokinase, or anticoagulants such as heparin, dermatan sulfate, activated protein C, vitamin K antagonists, hirudin, inhibitors of thrombin or other activated coagulation factors, together with one or more conventional inert excipients and/or diluents, for example with corn starch, lactose, sucrose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fat-containing substances such as hard fat or suitable mixtures thereof.

The following examples are intended to explain the invention in detail:
Preparation of the starting materials

EXAMPLE XVII

N-(2,2-Dimethoxyethyl)-N-[trans-4-[2-(methoxycarbonyl)ethyl]-cyclohexyl]-N'-(7-methyl-6,7,8,9-tetrahydro-5H-pyrazino[2,3-d]azepin-2-yl) urea 13.3 g of 2-amino-7-methyl-6,7,8,9-tetrahydro-5H-pyrazino[2,3-d]azepine (see EP-A-0,047,412, as dihydrochloride) in 90 ml of tetrahydrofuran are added dropwise at room temperature to 13.3 g of N,N'-carbonyldiimidazole and 7.62 g of imidazole in 110 ml of tetrahydrofuran under nitrogen. After stirring for 1 hour, 22.4 g of N-(2,2-dimethoxyethyl)-N-[trans-4-[2-(methoxycarbonyl)ethyl]cyclohexyl]amine (see WO-96/05194, as hemifumarate) in 50 ml of tetrahydrofuran are added dropwise. The mixture is stirred at 70° C. for 3 hours and at room temperature for 18 hours. The reaction mixture is concentrated, and the residue is taken up in 500 ml of ethyl acetate, washed three times with water and once with brine, dried and concentrated.

Yield: 37.1 g of an oil, which is reacted without purification.

$R_f$: 0.53 (silica gel; toluene/dioxane/methanol/concentrated aqueous ammonia=20:50:20:2)

The following compounds are obtained in analogy to Example XVII:

(1) N-(2,2-Dimethoxyethyl)-N-[trans-4-[2-(methoxycarbonyl)ethyl]cyclohexyl]-N'-(7-benzyl-6,7,8,9-tetrahydro-5H-pyrazino[2,3-d]azepin-2-yl)urea Melting point: 127°–131° C.

$R_f$: 0.35 (silica gel; methylene chloride/methanol/concentrated aqueous ammonia=95:5:2)

(2) N-(2,2-Diethoxyethyl)-N-[trans-4-[2-(methoxycarbonyl)ethyl]cyclohexyl]-N'-(7-ethyl-6,7,8,9-tetrahydro-5H-pyrido[2,3-d]azepin-3-yl)urea Carried out with 1,1'-carbonyldi(1,2,4-triazole)

$R_f$: 0.44 (silica gel; methylene chloride/methanol/concentrated aqueous ammonia=95:10:1)

(3) N-(2,2-Diethoxyethyl)-N-[trans-4-[2-(methoxycarbonyl)ethyl]cyclohexyl]-N'-(7-ethyl-6,7,8,9-tetrahydro-5H-pyrido[3,4-d]azepin-3-yl)urea Carried out with 1,1'-carbonyldi(1,2,4-triazole)

$R_f$: 0.44 (silica gel; methylene chloride/methanol/concentrated aqueous ammonia=90:10:1)

(4) N-(2,2-Diethoxyethyl)-N-[trans-4-[2-(methoxycarbonyl)ethyl]cyclohexyl-N'-(7-benzyl-6,7,8,9-tetrahydro-5H-pyrido[2,3-d]azepin-2-yl)urea $R_f$: 0.79 (silica gel; methylene chloride/methanol/concentrated aqueous ammonia=90:10:1)

(5) N-(2,2-Diethoxyethyl)-N-[4-[(ethoxycarbonylmethyl)oxy]phenyl]-N'-(7-ethyl-6,7,8,9-tetrahydro-5H-pyrazino[2,3-d]azepin-2-yl)urea Carried out with 1,1'-carbonyldi(1,2,4-triazole); the N-(2,2-diethoxyethyl)-N-[4-[(ethoxycarbonylmethyl)oxy]phenyl]amine [$R_f$: 0.33 (silica gel; cyclohexane/ethyl acetate=8:2) employed is obtained by reacting ethyl 4-aminophenyloxyacetate with bromoacetaldehyde diethyl acetal in dimethylformamide in the presence of N-ethyldiisopropylamine.

$R_f$: 0.27 (alumina; methylene chloride/ethyl acetate=8:2)

(6) N-(2,2-Diethoxyethyl)-N-[trans-4-[(methoxycarbonylmethyl)oxy]cyclohexyl]-N'-(7-methyl-6,7,8,9-tetrahydro-5H-pyrazino-[2,3-d]azepin-2-yl)urea The N-(2,2-diethoxyethyl)-N-[trans-4-[(methoxy-carbonylmethyl)oxy]cyclohexyl]amine [R$_f$: 0.64 (reversed phase silica gel; methanol/5% strength aqueous brine=6:4)] employed is prepared from methyl(trans-4-aminocyclohexyloxy)acetate hydrochloride by benzylation (benzaldehyde, N-ethyldiisopropylamine, hydrogen in methanol in the presence of Raney nickel), reaction with bromoacetaldehyde diethyl acetal (acetonitrile, N-ethyldiisopropylamine, potassium iodide, 18-crown-6) and subsequent debenzylation (methanol; hydrogen, palladium hydroxide)

R$_f$: 0.59 (silica gel; methylene chloride/methanol/concentrated aqueous ammonia =90:10:2)

(7) N-(1-tert-Butyloxycarbonyl-4-piperidinyl)-N-(2,2-diethoxyethyl)-N'-(7-methyl-6,7,8,9-tetrahydro-5H-pyrazino[2,3-d]azepin-2-yl)urea Carried out with 1,1'-carbonyldi(1,2,4-triazole)

The N-(1-tert-butyloxycarbonyl-4-piperidinyl)-N-(2,2-diethoxyethyl)amine [R$_f$: 0.48 (reversed phase silica gel; methanol/5% aqueous brine=6:4)] employed is prepared by reductive amination of 1-tert-butyloxycarbonyl-4-piperidone with aminoacetaldehyde diethyl acetal R$_f$: 0.69 (silica gel; methylene chloride/methanol/concentrated aqueous ammonia=90:10:2)

(8) N-(2,2-Dimethoxyethyl)-N-[cis-4-[2-(methoxycarbonyl)ethyl]cyclohexyl]-N'-(7-benzyl-6,7,8,9-tetrahydro-5H-pyrazino[2,3-d]azepin-2-yl)urea Melting point: 104°–107° C.

(9) N-(1-tert-Butyloxycarbonyl-4-piperidinyl)-N-(2,2-diethoxyethyl)-N'-(7-ethyl-6,7,8,9-tetrahydro-5H-pyrazino[2,3-d]azepin-2-yl)urea Carried out with 1,1'-carbonyldi(1,2,4-triazole)

R$_f$: 0.55 (silica gel; methylene chloride/methanol/concentrated aqueous ammonia=90:10:1)

(10) N-(2,2-Diethoxyethyl)-N-[trans-4-[(methoxy-carbonylmethyl)oxy]cyclohexyl]-N'-(7-ethyl-6,7,8,9-tetrahydro-5H-pyrazino[2,3-d]azepin-2-yl)urea Carried out with 1,1'-carbonyldi(1,2,4-triazole)

R$_f$: 0.29 (refersed phase silica gel; methanol/5% aqueous brine=6:4)

(11) N-(2-Hydroxyethyl)-N-[4-[2-(methoxycarbonyl)ethyl]phenyl]-N'-(7-ethyl-6,7,8,9-tetrahydro-5H-pyrazino[2,3-d]azepin-2-yl)urea Carried out with 1,1'-carbonyldi(1,2,4-triazole)

R$_f$: 0.42 (silica gel; methylene chloride/methanol/concentrated aqueous ammonia=4:1:0.1)

(12) N-(1,1-Dimethoxy-2-propyl)-N-[trans-4-[2-(methoxycarbonyl)ethyl]cyclohexyl]-N'-(7-ethyl-6,7,8,9-tetrahydro-5H-pyrazino[2,3-d]azepin-2-yl)urea Carried out with 1,1'-carbonyldi(1,2,4-triazole)

The N-(1,1-dimethoxy-2-propyl)-N-[trans-4-[2-(methoxycarbonyl)ethyl]cyclohexyl]amine [R$_f$: 0.74 (silica gel; methylene chloride/methanol/concentrated aqueous ammonia=90:10:1)] employed is obtained by reductive amination of 4-[2-(methoxycarbonyl)ethyl]cyclohexanone with 1,1-dimethoxy-2-propylamine.

R$_f$: 0.57 (silica gel; methylene chloride/methanol/concentrated aqueous ammonia=90:10:1)

(13) N-(1,1-Dimethoxy-2-propyl)-N-[trans-4-[2-(methoxycarbonyl)ethyl]cyclohexyl]-N'-(7-methyl-6,7,8,9-tetrahydro-5H-pyrazino[2,3-d]azepin-2-yl)urea Carried out with 1,1'-carbonyldi(1,2,4-triazole)

R$_f$: 0.46 (silica gel; methylene chloride/methanol/concentrated aqueous ammonia=90:10:1)

(14) N-(2-Hydroxy-1-propyl)-N-[trans-4-[2-(methyloxycarbonyl)ethyl]cyclohexyl]-N'-(7-methyl-6,7,8,9-tetrahydro-5H-pyrazino[2,3-d]azepin-2-yl)urea Carried out with 1,1'-carbonyldi(1,2,4-triazole)

The N-(2-hydroxy-1-propyl)-N-[trans-4-[2-(methoxycarbonyl)ethyl]cyclohexyl]amine [R$_f$: 0.22 (alumina; methylene chloride/methanol=98:2)] employed is obtained by reductive amination of 4-[2-(methoxycarbonyl)ethyl]cyclohexanone with 2-hydroxypropylamine.

R$_f$: 0.32 (silica gel; methylene chloride/methanol/concentrated aqueous ammonia=90:10:1)

Example XVIII

2-Amino-7-benzyl-6,7,8,9-tetrahydro-5H-pyrazino-[2,3-d]azepine 81.6 g of bromine are added dropwise in about 45 minutes to 186.0 g of 1-benzyl-2,3,6,7-tetrahydro-4,5-bis (trimethylsilyloxy)azepine (Finch, N. et al., J. Org. Chem. 42, 3933 (1977)) in 1.7 l of dioxane and 162 g of pyridine at an internal temperature of 10°–13° C. The reaction mixture is subsequently stirred at an internal temperature of 8°–12° C. for 20 minutes and then added to a stirred mixture of 74.6 g of aminoacetamidine dihydrochloride (prepared from 2-benzyloxycarbonylaminoacetamidine hydrochloride (Mengelberg, Chem. Ber. 89, 1185 (1956)) by catalytic hydrogenation in methanol in the presence of hydrochloric acid and palladium/carbon), 1 l of water and 1 kg of crushed ice while cooling in ice. This reaction mixture is stirred under nitrogen without further cooling for 6 hours and then left to stand overnight. The reaction mixture is subsequently stirred with 1 l of tert-butyl methyl ether and the phases are separated. 1 l of ethyl acetate is added to the stirred aqueous phase, and 200 g of potassium carbonate are introduced in portions and about 6 g of sodium dithionite are added. The phases are separated and the aqueous phase is extracted twice more with 1 l of ethyl acetate each time. The combined organic phases are washed with 0.5 l of brine, dried and concentrated. The residue is mixed with toluene and concentrated again once. After purification via the maleic acid salt, the free base is isolated with sodium hydroxide solution.

Yield: 73.7 g (56% of theory),

Melting point: 117°–120° C.

EXAMPLE XIX (7-Ethyl-6,7,8,9-tetrahydro-5H-pyrazino[2,3-d]azepin-2-yl)aminoacetate 3.88 g of 70% strength perchloric acid are added to 2.7 g of 2-amino-7-ethyl-6,7,8,9-tetrahydro-5H-pyrazino[2,3-d]azepine while stirring and cooling in ice. Then 1.45 g of 40% strength glyoxal in 10 ml of ethanol are added, and the mixture is heated under reflux for 22 hours. It is cooled in an ice bath, methylene chloride is added, and the mixture is made alkaline with potassium carbonate solution. The solid is filtered off with suction, and the organic phase of the filtrate is separated off, washed with water, and dried and concentrated. The residue is purified by chromatography on an alumina column with methylene chloride and methylene chloride/ethanol (99:1).

Yield: 430 mg (15% of theory),

Melting point: 116°–188° C.

The following compound is obtained in analogy to

EXAMPLE XIX (1) Ethyl (7-methyl-6,7,8,9-tetrahydro-5H-pyrazino[2,3-d]azepin-2-yl)aminoacetate Melting point: 115°–117° C.

$R_f$: 0.43 (alumina; methylene chloride/methanol=98:2)

EXAMPLE XX 1-(4-Piperidinyl)-3-(7-methyl-6,7,8,9-tetrahydro-5H-pyrazino-[2,3-d]azepin-2-yl)imidazolidin-2-one 2.2 g of 1-(4-piperidinyl)-3-(7-methyl-6,7,8,9-tetrahydro-5H-pyrazino[2,3-d]azepin-2-yl)-3H-imidazol-2-one are hydrogenated in 50 ml of methanol at 50° C. under a pressure of 50 psi of hydrogen in the presence of a total of 1.5 g of palladium on carbon (added in 3 portions) for 2.5 days. The catalyst is then filtered off with suction and the filtrate is evaporated.

Yield: 2.0 g (90% of theory), $R_f$: 0.19 (alumina; methylene chloride/methanol=95:5)

The following compound is obtained in analogy to

EXAMPLE XX (1) 1-(4-Piperidinyl)-3-(7-ethyl-6,7,8,9-tetrahydro-5H-pyrazino[2,3-d]azepin-2-yl)imidazolidin-2-one $R_f$: 0.22 (silica gel; methylene chloride/methanol/concentrated aqueous ammonia=9:1:0.1)

EXAMPLE XXI 1-(4-Piperidinyl)-3-(7-methyl-6,7,8,9-tetrahydro-5H-pyrazino[2,3-d]azepin-2-yl)-3H-imidazol-2-one 4.0 g of N-(1-tert-butyloxycarbonyl-4-piperidinyl)-N-(2,2-diethoxyethyl)-N'-(7-methyl-6,7,8,9-tetrahydro-5H-pyrazino[2,3-d]azepin-2-yl)urea and 35 ml of trifluoroacetic acid are stirred at room temperature for 2.5 days. The mixture is concentrated, taken up in water, adjusted to pH 12–13 with 15N sodium hydroxide solution and extracted 4 times with methylene chloride. The organic phase is dried and concentrated.

Crude yield: 2.8 g, $R_f$: 0.51 (silica gel; methylene chloride/methanol/concentrated aqueous ammonia=90:10:2)

The following compound is obtained in analogy to

EXAMPLE XXI (1) 1-(4-Piperidinyl)-3-(7-ethyl-6,7,8,9-tetrahydro-5H-pyrazino[2,3-d]azepin-2-yl)-3H-imidazol-2-one $R_f$: 0.40 (silica gel; methylene chloride/methanol/concentrated aqueous ammonia=90:10:1)

EXAMPLE XXII

2-Amino-7-benzyl-6,7,8,9-tetrahydro-5H-pyrido[2,3-d]azepine

Prepared by reacting 2-chloro-7-benzyl-6,7,8,9-tetrahydro-5H-pyrido[2,3-d]azepine with ammonium tetrachlorozincate at 230° C.

Melting point: 79°–87° C.

$R_f$: 0.54 (silica gel, methylene chloride/methanol/concentrated aqueous ammonia=10:1:0.1)

a) 2-Chloro-7-benzyl-6,7,8,9-tetrahydro-5H-pyrido[2,3-d]azepine

Prepared by reacting 2-hydroxy-7-benzyl-6,7,8,9-tetrahydro-5H-pyrido[2,3-d]azepine dihydrochloride with phosphorus oxychloride at 140° C.

Melting point: 77°–79° C.

b) 2-Hydroxy-7-benzyl-6,7,8,9-tetrahydro-5H-pyrido[2,3-d]azepine dihydrochloride Prepared from 2-hydroxy-3-ethoxycarbonyl-7-benzyl-6,7,8,9-tetrahydro-5H-pyrido[2,3-d]azepine by treatment with hydrochloric acid at 180° C.

Melting point: 260°–271° C.

c) 2-Hydroxy-3-ethoxycarbonyl-7-benzyl-6,7,8,9-tetrahydro-5H-pyrido[2,3-d]azepine Prepared from 1-benzyl-hexahydro-4-azepinone with ethyl formate and ethyl malonamate in the presence of sodium hydride.

Melting point: 181°–183° C.

EXAMPLE XXIII

3-Amino-7-ethyl-6,7,8,9-tetrahydro-5H-pyrido[2,3-d]azepine

Prepared from 3-amino-2-chloro-7-ethyl-6,7,8,9-tetrahydro-5H-pyrido[2,3-d]azepine by catalytic hydrogenation in the presence of palladium dichloride in methanol.

$R_f$: 0.18 (silica gel, methylene chloride/methanol/concentrated aqueous ammonia=90:10:1)

a) 3-Amino-2-chloro 7-ethyl-6,7,8,9-tetrahydro-5H-pyrido[2,3-d]azepine

Prepared from 3-amino-2-hydroxy-7-ethyl-6,7,8,9-tetrahydro-5H-pyrido[2,3-d]azepine by reaction with phosphorus oxychloride at 150° C.

Melting point: 260°–265° C. (as dihydrochloride)

b) 3-Amino-2-hydroxy-7-ethyl-6,7,8,9-tetrahydro-5H-pyrido[2,3-d]azepine

Prepared from 3-aminocarbonyl-2-hydroxy-7-ethyl-6,7,8,9-tetrahydro-5H-pyrido[2,3-d]azepine by reaction with potassium hydroxide/bromine.

Melting point: 165°–175° C.

c) 3-Aminocarbonyl-2-hydroxy-7-ethyl-6,7,8,9-tetrahydro-5H-pyrido[2,3-d]azepine

Prepared from 3-cyano-2-hydroxy-7-ethyl-6,7,8,9-tetrahydro-5H-pyrido[2,3-d]azepine by treatment with polyphosphoric acid at 120° C.

Melting point: 265°–270° C.

d) 3-Cyano-2-hydroxy-7-ethyl-6,7,8,9-tetrahydro-5H-pyrido[2,3-d]azepine

Prepared from 1-ethylhexahydro-4-azepinone by reaction with ethyl formate and cyanoacetamide in the presence of sodium hydride.

Melting point: 210°–220° C.

EXAMPLE XXIV

3-Amino-7-ethyl-6,7,8,9-tetrahydro-5H-pyrido[3,4-d]azepine prepared from 3-chloro-7-ethyl-6,7,8,9-tetrahydro-5H-pyrido[3,4-d]azepine by reaction with ammonium tetrachlorozincate at 220° C.

Melting point: 107°–110° C.

a) 3-Chloro-7-ethyl-6,7,8,9-tetrahydro-5H-pyrido[3,4-d]azepine

Prepared from 3-hydroxy-7-ethyl-6,7,8,9-tetrahydro-5H-pyrido[3,4-d]azepine dihydrochloride by reaction with phosphorus oxychloride at 130° C.

b) 3-Hydroxy-7-ethyl-6,7,8,9-tetrahydro-5H-pyrido[3,4-d]azepine dihydrochloride

Prepared from 4-ethoxycarbonyl-3-hydroxy-7-ethyl-6,7,8,9-tetrahydro-5H-pyrido[3,4-d]azepine by treatment with hydrochloric acid at 130° C.

Melting point: 220°–230° C.

c) 4-Ethoxycarbonyl-3-hydroxy-7-ethyl-6,7,8,9-tetrahydro-5H-pyrido[3,4-d]azepine Prepared from 4-ethoxycarbonyl-3-hydroxy-7-benzyl-6,7,8,9-tetrahydro-5H-pyrido[3,4-d]azepine 2-oxide by hydrogenation in ethanol at 130° C. in the presence of Raney nickel.

Melting point: 121°–126° C.

d) 4-Ethoxycarbonyl-3-hydroxy-7-benzyl-6,7,8,9-tetrahydro-5H-pyrido[3,4-d]azepine 2-oxide Prepared from 1-benzyl-4-chloro-5-hydroxyiminomethyl-2,3,6,7-tetrahydro-1H-azepine by reaction with diethyl malonate in the presence of sodium hydride and catalytic amounts of copper(I) bromide at 100° C.

Melting point: 98°–105° C.

e) 1-Benzyl-4-chloro-5-hydroxyiminomethyl-2,3,6,7-tetrahydro-1H-azepine

Prepared by reacting 1-benzyl-4-chloro-5-formyl-2,3,6,7-tetrahydro-1H-azepine hydrochloride with hydroxylamine hydrochloride in ethanol at 30° C.

Melting point: 138°–145° C.

f) 1-Benzyl-4-chloro-5-formyl-2,3,6,7-tetrahydro-1H-azepine hydrochloride

Prepared from 1-benzylhexahydro-4-azepinone hydrochloride by reaction with dimethylformamide/phosphorus oxychloride in methylene chloride at 20°–35° C.

Melting point: 205°–215° C.

Preparation of the final products

EXAMPLE 31

1-[trans-4-(2-Carboxyethyl)cyclohexyl]-3-(7-methyl-6,7,8,9-tetrahydro-5H-pyrazino[2,3-d]azepin-2-yl)imidazolidin-2-one methanesulfonate 19.0 g of 1-[trans-4-(2-carboxyethl)cyclohexyl]-3-(7-methyl-6,7,8,9-tetrahydro-5H-pyrazino[2,3-d]azepin-2-yl)imidazolidin-2-one×1 $H_2O$ are added to a mixture of 4.39 g of methanesulfonic acid and 10 ml of water. A further 20 ml of water is added and the mixture is stirred at 60° C. until the solid has dissolved. About 100 ml of acetone are added, the mixture is quickly filtered, and 500 ml of acetone are added to the fitrate. After stirring at room temperature for 0.5 hours, the mixture is cooled in an ice bath. The solid is filtered off with suction, washed with acetone and dried at 60° C.

Yield: 18.76 g (83% of theory),

Melting point: 246° C.

$R_f$: 0.39 (reversed phase silica gel; methanol/5% aqueous brine=6:4)

| Calc.: | C | 53.10 | H | 7.09 | N | 14.07 | S | 6.44 |
|---|---|---|---|---|---|---|---|---|
| Found: | | 53.04 | | 7.10 | | 13.98 | | 6.12 |

The following compound is obtained in analogy to Example 31:

(1) 1-[trans-4-(2-carboxyethyl)cyclohexyl]-3-(7-methyl-6,7,8,9-tetrahydro-5H-pyrazino[2,3-d]azepin-2-yl)imidazolidin-2-one hydrochloride Carried out with hydrochloric acid Melting point: about 290° C. (decomposition)

| Calc.: | C | 57.59 | H | 7.36 | N | 15.99 | S | 8.09 |
|---|---|---|---|---|---|---|---|---|
| Found: | | 57.42 | | 7.45 | | 15.71 | | 8.52 |

EXAMPLE 32

1-[trans-4-(2-Carboxyethyl)cyclohexyl]-3-(7-methyl-6,7,8,9-tetrahydro-5H-pyrazino[2,3-d]azepin-2-yl)imidazolidin-2-one×1 $H_2O$ 120 ml of 1N sodium hydroxide solution are added to 17.05 g of 1-[trans-4-(methoxycarbonyl)ethyl]cyclohexyl]-3-(7-methyl-6,7,8,9-tetrahydro-5H-pyrazino[2,3-d]azepin-2-yl)imidazolidin-2-one in 300 ml of tetrahydrofuran, and the mixture is stirred overnight. The reaction mixture is filtered and the tetrahydrofuran portion of the filtrate is removed in vacuo. The remaining aqueous solution is cooled in an ice bath and adjusted to pH 6.5 with 2N hydrochloric acid. The solid is filtered off with suction, washed with water and acetone and dried at 60° C.

Yield: 14.74 g (85% of theory),

Melting point: from 260° C. (decomposition)

| Calc.: | C | 60.12 | H | 7.93 | N | 16.69 |
|---|---|---|---|---|---|---|
| Found: | | 60.11 | | 7.97 | | 16.53 |

The following compounds are obtained in analogy to Example 32:

(1) 1-[trans-4-(2-Carboxyethyl)cyclohexyl]-3-(7-ethyl-6,7,8,9-tetrahydro-5H-pyrido[2,3-d]azepin-3-yl)imidazolidin-2-one×1 $H_2O$ Melting point: 243°–250° C. (decomposition)

$R_f$: 0.41 (reversed phase silica gel, methanol/5% aqueous brine=6:4)

(2) 1-[trans-4-(2-carboxyethyl)cyclohexyl]-3-(7-ethyl-6,7,8,9-tetrahydro-5H-pyrido[3,4-d]imidazolidin-2one $R_f$: 0.43 (reversed phase silica gel; methanol/5% aqueous brine=6:4)

(3) 1-[trans-4-(2-Carboxyethyl)cyclohexyl]-3-(6,7,8,9-tetrahydro-5H-pyrido[2,3-d]azepin-2-yl)imidazolidin-2-one Melting point: from 265° C. (decomposition)

$R_f$: 0.45 (reversed phase silica gel; methanol/5% aqueous brine=6:4)

| Calc.: | C | 65.26 | H | 7.82 | N | 14.50 |
|---|---|---|---|---|---|---|
| Found: | | 65.07 | | 7.91 | | 14.30 |

(4) 1-[trans-4-(2-Carboxyethyl)cyclohexyl]-3-(7-benzyl-6,7,8,9-tetrahydro-5H-pyrazino[2,3-d]azepin-2-yl)imidazolidin-4-one Melting point: 211°–214° C.

| Calc.: | C | 67.90 | H | 7.39 | N | 14.66 |
|---|---|---|---|---|---|---|
| Found: | | 68.01 | | 7.45 | | 14.47 |

(5) 1-[trans-4-(2-Carboxyethyl)cyclohexyl]-3-(6,7,8,9-tetrahydro-5H-pyrazino[2,3-d]azepin-2-yl)imidazolidin-2-one Melting point: from 290° C. (decomposition)

| Calc.: | C | 62.00 | H | 7.54 | N | 18.07 |
|---|---|---|---|---|---|---|
| Found: |  | 61.91 |  | 7.52 |  | 18.13 |

(6) 1-[trans-4-(2-Carboxyethyl)cyclohexyl]-3-(6,7,8,9-tetrahydro-5H-pyrazino[2,3-d]azepin-2-yl)-3H-imidazol-2-one $R_f$: 0.43 (reversed phase silica gel; methanol/5% aqueous brine=6:4)

(7) 1-[trans-4-(2-Carboxyethyl)cyclohexyl-3-(7-methyl-6,7,8,9-tetrahydro-5H-pyrazino[2,3-d]azepin-2-yl)-3H-imidazol-2-one×0.5 H$_2$O Melting point: about 290° C. (decomposition; sintering from 250° C.)

| Calc.: | C | 61.27 | H | 7.40 | N | 17.14 |
|---|---|---|---|---|---|---|
| Found: |  | 61.18 |  | 7.64 |  | 17.01 |

(8) 1-[cis-4-(2-Carboxyethyl)cyclohexyl]-3-(7-methyl-6,7,8,9-tetrahydro-5H-pyrazino[2,3-d]azepin-2-yl)imidazolidin-2-one×1.2 H$_2$O $R_f$: 0.43 (reversed phase silica gel; methanol/5% aqueous brine=6:4)

| Calc.: | C | 61.19 | H | 7.52 | N | 17.84 |
|---|---|---|---|---|---|---|
| Found: |  | 61.17 |  | 7.51 |  | 17.73 |

(10) 3-[trans-4-(2-Carboxyethyl)cyclohexyl]-1-(7-ethyl-6,7,8,9-tetrahydro-5H-pyrazino[2,3-d]azepin-2-yl)-4-methyl-imidazolidin-2-one×2 H$_2$O Melting point: 182°–184° C.

| Calc.: | C | 59.33 | H | 8.44 | N | 15.04 |
|---|---|---|---|---|---|---|
| Found: |  | 59.51 |  | 8.50 |  | 14.70 |

(11) 3-[trans-4-(2-Carboxyethyl)cyclohexyl]-1-(7-ethyl-6,7,8,9-tetrahydro-5H-pyrazino[2,3-d]azepin-2-yl)-4-methyl-3H-imidazol-2-one $R_f$: 0.42 (reversed phase silica gel; methanol/5% aqueous brine=6:4)

EXAMPLE 33

1-[trans-4-[2-(Methoxycarbonyl)ethyl]cyclohexyl]-3-(7-methyl-6,7,8,9-tetrahydro-5H-pyrazino[2,3-d]azepin-2-yl)-imidazolidin-2-one 19.3 g of 1-[trans-4-[2-(methoxycarbonyl)ethyl]cyclohexyl]-3-(7-methyl-6,7,8,9-tetrahydro-5H-pyrazino[2,3-d]azepin-2-yl)-3H-imidazol-2-one are hydrogenated in 500 ml of methanol at 50° C. under a pressure of 50 psi of hydrogen in the presence of 10 g of palladium on carbon (10% palladium) for 20 hours. The reaction mixture is heated on a steam bath and filtered, and the filtrate is concentrated.

Yield: 17.7 g (91% of theory),

Melting point: 136°–142° C.

$R_f$: 0.31 (silica gel; methylene chloride/methanol/concentrated aqueous ammonia=90:10:2)

A sample is purified by chromatography on an alumina column with methylene chloride/methanol (99.5:0.5).

Melting point: 145°14 154° C.

| Calc.: | C | 63.59 | H | 8.00 | N | 16.85 |
|---|---|---|---|---|---|---|
| Found: |  | 63.74 |  | 8.00 |  | 16.67 |

The following compounds are obtained in analogy to Example 33:

(1) 1-[trans-4-[2-(Methoxycarbonyl)ethyl]cyclohexyl]-3-(6,7,8,9-tetrahydro-5H-pyrazino[2,3-d]azepin-2-yl)-imidazolidin-2-one Prepared from the compound of Example 34(1) in the presence of potassium acetate and isolation of the free base Melting point: 154°–158° C.

| Calc.: | C | 62.82 | H | 7.78 | N | 17.44 |
|---|---|---|---|---|---|---|
| Found: |  | 63.10 |  | 7.82 |  | 17.32 |

Premature termination of the hydrogenation of the compound from Example 34(1) results in the compound 1-[trans-4-[2-(methoxycarbonyl)ethyl]cyclohexyl)-3-(6,7,8,9-tetrahydro-5H-pyrazino[2,3-d]azepin-2-yl)-3H-imidazol-2-one $R_f$: 0.30 (silica gel; toluene/dioxane/methanol/concentrated aqueous ammonia=20:50:20:2)

(2) 1-[trans-4-[2-(Methoxycarbonyl)ethyl]cyclohexyl]-3-(7-ethyl-6,7,8,9-tetrahydro-5H-pyrido[2,3-d]azepin-3-yl)-imidazolidin-2-one Melting point: 120°–124° C.

| Calc.: | C | 67.26 | H | 8.47 | N | 13.07 |
|---|---|---|---|---|---|---|
| Found: |  | 67.21 |  | 8.46 |  | 12.80 |

(3) 1-[trans-4-[2-(Methoxycarbonyl)ethyl]cyclohexyl]-3-(7-ethyl-6,7,8,9-tetrahydro-5H-pyrido[3,4-d]azepin-3-yl)imidazolidin-2-one×0.4 H$_2$O Melting point: 106°–110 °C.

| Calc.: | C | 66.15 | H | 8.51 | N | 12.86 |
|---|---|---|---|---|---|---|
| Found: |  | 66.15 |  | 8.41 |  | 12.44 |

(4) 1-[trans-4-[2-(Methoxycarbonyl)ethyl]cyclohexyl]-3-(6,7,8,9-tetrahydro-5H-pyrido[2,3-d]azepin-2-yl)imidazolidin-2-one Carried out with palladium on carbon and palladium hydroxide on carbon.

Melting point: 143°–160° C.

$R_f$: 0.40 (reversed phase silica gel; methanol/5% aqueous brine=6:4)

(5) 1-[4-[(Ethoxycarbonylmethyl)oxy]phenyl]-3-(7-ethyl-6,7,8,9-tetrahydro-5H-pyrazino[2,3-d]azepin-2-yl)imidazolidin-2-one Melting point: 175°–177° C.

(6) 1-[trans-4-[(Methoxycarbonylmethyl)oxy]cyclohexyl]-3-(7-methyl-6,7,8,9-tetrahydro-5H-pyrazino[2,3-d]azepin-2-yl)imidazolidin-2-one Melting point: 118°–120° C.

(7) 1-[cis-4-[2-(Methoxycarbonylethyl)cyclohexyl]-3-(6,7,8,9-tetrahydro-5H-pyrazino[2,3-d]azepin-2-yl)imidazolidin-2-one Melting point: 124°–134° C.

| Calc.: | C | 62.82 | H | 7.78 | N | 17.44 |
|---|---|---|---|---|---|---|
| Found: | | 62.86 | | 7.75 | | 17.56 |

(8) 1-[1-[2-(Ethoxycarbonyl)ethyl]piperidin-4-yl]-3-(7-ethyl-6,7,8,9-tetrahydro-5H-pyrazino[2,3-d]azepin-2-yl)imidazolidin-2-one $R_f$: 0.50 (silica gel; methylene chloride/methanol/concentrated aqueous ammonia=9:1:0.1)

(9) 1-[trans-4-[(Methoxycarbonylmethyl)oxy]cyclohexyl]-3-(7-ethyl-6,7,8,9-tetrahydro-5H-pyrazino[2,3-d]azepin-2-yl)imidazolidin-2-one $R_f$: 0.71 (silica gel; methylene chloride/methanol/concentrated aqueous ammonia=9:1:0.1)

(10) 3-[trans-4-[2-(Methoxycarbonyl)ethyl]cyclohexyl]-1-(7-ethyl-6,7,8,9-tetrahydro-5H-pyrazino[2,3-d]azepin-2-yl)-4-methylimidazolidin-2-one $R_f$: 0.67 (silica gel; methylene chloride/methanol/concentrated aqueous ammonia=9:1:0.1)

(11) 3-[trans-4-[2-(Methoxycarbonyl)ethyl]cyclohexyl]-1-(7-methyl-6,7,8,9-tetrahydro-5H-pyrazino[2,3-d]azepin-2-yl)-4-methylimidazolidin-2-one $R_f$: 0.32 (reversed phase silica gel; methanol/5% aqueous brine=6:4)

EXAMPLE 34

1-[trans-4-[2-(Methoxycarbonyl)ethyl]cyclohexyl]-3-(7-methyl-6,7,8,9-tetrahydro-5H-pyrazino[2,3-d]azepin-2-yl)-3H-imidazol-2-one 37 g of gaseous hydrogen chloride are passed into a solution of 35.0 g of N-(2,2-dimethoxyethyl)-N-[trans-4-[2-(methoxycarbonyl)ethyl]cyclohexyl]-N'-(7-methyl-6,7,8,9-tetrahydro-5H-pyrazino[2,3-d]azepin-2-yl)urea in methanol while cooling in ice and stirring. The mixture is stirred at room temperature overnight and subsequently heated under reflux for 40 minutes. The reaction mixture is evaporated to dryness, dissolved in 300 ml of ice-water and made alkaline with saturated potassium carbonate solution. The precipitate is filtered off with suction, washed with ice-water and diethyl ether and dried.

Yield: 15.45 g (50% of theory),

Melting point: 121°–126° C.

$R_f$: 0.44 (silica gel; toluene/dioxane/methanol/concentrated aqueous ammonia=20:50:20:2)

The following compounds are obtained in analogy to Example 34:

(1) 1-[trans-4-[2-(Methoxycarbonyl)ethyl]cyclohexyl]-3-(7-benzyl-6,7,8,9-tetrahydro-5H-pyrazino[2,3-d]azepin-2-yl)-3H-imidazol-2-one dihydrochloride.

Melting point: 225°–227° C. (decomposition)

(2) 1-[trans-4-[2-(Methoxycarbonyl)ethyl]cyclohexyl]-3-(7-ethyl-6,7,8,9-tetrahydro-5H-pyrido[2,3-d]azepin-3-yl)-3H-imidazol-2-one Carried out with trifluoroacetic acid.

Melting point: 117°–124° C.

$R_f$: 0.30 (Silica gel; methylene chloride/methanol/concentrated aqueous ammonia=90:10:1)

(3) 1-[trans-4-[2-(Methoxycarbonyl)ethyl]cyclohexyl]-3-(7-ethyl-6,7,8,9-tetrahydro-5H-pyrido[3,4-d]azepin-3-yl)-3H-imidazol-2-one Carried out with trifluoroacetic acid.

$R_f$: 0.45 (alumina; methylene chloride/methanol=99:1)

(4) 1-[trans-4-[2-(Methoxycarbonyl)ethyl]cyclohexyl]-3-(7-benzyl-6,7,8,9-tetrahydro-5H-pyrido[2,3-d]azepin-2-yl)-3H-imidazol-2-one Carried out with trifluoroacetic acid.

Melting point: 141°–148° C.

$R_f$: 0.17 (reversed phase silica gel: methanol/5% aqueous brine=6:4)

(5) 1-[4-[(Ethoxycarbonylmethyl)oxy]phenyl]-3-(7-ethyl-6,7,8,9-tetrahydro-5H-pyrazino[2,3-d]azepin-2-yl)-3-imidazol-2-one Carried out with trifluoroacetic acid.

Melting point: 157°–159° C.

(6) 1-[trans-4-[[Methoxycarbonylmethyl)oxy]cyclohexyl]-3-(7-methyl-6,7,8,9-tetrahydro-5H-pyrazino[2,3-d]azepin-2-yl)-3H-imidazol-2-one Carried out with trifluoroacetic acid.

Melting point: 127°–130° C.

(7) 1-[cis-4-[2-(Methoxycarbonyl)ethyl]cyclohexyl]-3-(7-methyl-6,7,8,9-tetrahydro-5H-pyrazino[2,3-d]azepin-2-yl)-3H-imidazol-2-one Melting point: 123°–126° C.

(8) 1-[trans-4-[(Methoxycarbonylmethyl)oxy]cyclohexyl]-3-(7-ethyl-6,7,8,9-tetrahydro-5H-pyrazino[2,3-d]azepin-2-yl)-3H-imidazol-2-one Carried out with trifluoroacetic acid.

$R_f$: 0.48 (reversed phase silica gel; methanol/5% aqueous brine=6:4)

(9) 3-[trans-4-[2-(Methoxycarbonyl)ethyl]cyclohexyl]-1-(7-ethyl-6,7,8,9-tetrahydro-5H-pyrazino[2,3-d]azepin-2-yl)-4-methyl-3H-imidazol-2-one $R_f$: 0.68 (silica gel, methylene chloride/methanol/concentrated aqueous ammonia=9:1:0.1)

(10) 3-[trans-4-[2-(Methoxycarbonyl)ethyl]cyclohexyl]-1-(7-methyl-6,7,8,9-tetrahydro-5H-pyrazino(2,3-d]azepin-2-yl)-4-methyl-3H-imidazol-2-one $R_f$: 0.73 (silica gel, methylene chloride/methanol/concentrated aqueous ammonia=9:1:0.1)

EXAMPLE 35

1-[trans-4-[2-(Methoxycarbonyl)ethyl]cyclohexyl]-3-(7-methyl-6,7,8,9-tetrahydro-5H-pyrazino[2,3-d]azepin-2-yl)imidazolidin-2-one 10.7 g of 1-[trans-4-[2-(methoxycarbonyl)ethyl]cyclohexyl]-3-(6,7,8,9-tetrahydro-5H-pyrazino[2,3-d]azepin-2-yl)imidazolidin-2-one acetate (crude product of Example 33(1)), 10 ml of water, 7.5 ml of formic acid and 2.2 ml of 37% strength formalin solution are stirred at 70° C. for 4 hours. A further 0.5 ml of formalin solution is added and heating is continued for 1.5 hours. The reaction mixture is evaporated, and the residue is stirred with toluene and again evaporated to dryness.

Yield: 13.5 g of crude product, which is used immediately to synthesize the compound of Example 32.

$R_f$: 0.44 (silica gel; toluene/dioxane/methanol/concentrated aqueous ammonia=20:50:20:2)

The following compounds are obtained in analogy to Example 35:

(1) 1-[trans-4-(2-Carboxyethyl)cyclohexyl]-3-(7-methyl-6,7,8,9-tetrahydro-5H-pyrido[2,3-d]azepin-2-yl)imidazolidin-2-one dihydrochloride×2H$_2$O Melting point: >250° C.

R$_f$: 0.35 (reversed phase silica gel; methanol/5% aqueous brine=6:4)

| Calc.: | C | 51.86 | H | 7.52 | N | 11.00 | Cl | 13.92 |
|---|---|---|---|---|---|---|---|---|
| Found: | | 51.94 | | 7.48 | | 10.93 | | 14.21 |

(2) 1-[trans-4-[2-(Methoxycarbonyl)ethyl]cyclohexyl]-3-(7-methyl-6,7,8,9-tetrahydro-5H-pyrazino[2,3-d]azepin-2-yl)-3H-imidazol-2-one×0.5 H$_2$O Carried out with formaldehyde/sodium cyanoborohydride R$_f$: 0.57 (silica gel; toluene/dioxane/methanol/concentrated aqueous ammonia 20:50:20:2)

| Calc.: | C | 62.54 | H | 7.63 | N | 16.57 |
|---|---|---|---|---|---|---|
| Found: | | 62.60 | | 7.52 | | 16.50 |

(3) 1-[cis-4-[2-(Methoxycarbonyl)ethyl]cyclohexyl]-3-(7-methyl-6,7,8,9-tetrahydro-5H-pyrazino[2,3-d]azepin-2-yl)imidazolidin-2-one Melting point: 115°–121° C.

EXAMPLE 36

3-[trans-4-(2-Carboxyethyl)cyclohexyl]-1-(7-ethyl-6,7,8,9-tetrahydro-5H-pyrazino[2,3-d]azepin-2-yl)imidazolidine-2,4-dione hydrochloride×0.5 H$_2$O 500 mg of 3-[trans-4-[2-(methoxycarbonyl)ethyl]cyclohexyl]-1-(7-ethyl-6,7,8,9-tetrahydro-5H-pyrazino[2,3-d]azepin-2-yl)imidazolidine-2,4-dione are dissolved in 10 ml of 3N hydrochloric acid by heating to 50° C. and stirred at room temperature overnight. The reaction mixture is evaporated to dryness, and the residue is stirred with acetone, filtered off with suction, washed with acetone and diethyl ether and dried at 30° C.

Yield: 500 mg (94% of theory),

Melting point: from 285° C. (decomposition)

R$_f$: 0.41 (reversed phase silica gel; methanol/5% aqueous brine=6:4)

| Calc.: | C | 55.63 | H | 7.00 | N | 14.74 | Cl | 7.46 |
|---|---|---|---|---|---|---|---|---|
| Found: | | 56.04 | | 6.93 | | 14.48 | | 7.71 |

The following compounds are obtained in analogy to Example 36:

(1) 1-[4-[(Carboxymethyl)oxy]phenyl]-3-(7-ethyl-6,7,8,9-tetrahydro-5H-pyrazino[2,3-d]azepin-2-yl)imidazolidin-2-one×1.75 HCl×H$_2$O Melting point: >250° C.

R$_f$: 0.43 (reversed phase silica gel; methanol/5% aqueous brine=6:4)

| Calc.: | C | 51.13 | H | 5.87 | N | 14.20 | Cl | 12.58 |
|---|---|---|---|---|---|---|---|---|
| Found: | | 51.52 | | 5.86 | | 14.13 | | 12.54 |

(2) 1-[trans-4-[(Carboxymethyl)oxy]cyclohexyl]-3-(7-methyl-6,7,8,9-tetrahydro-5H-pyrazino[2,3-d]azepin-2-yl)imidazolidin-2-one dihydrochloride Melting point: >250° C.

R$_f$: 0.54 (reversed phase silica gel; methanol/5% aqueous brine=6:4)

(3) 1-[1-(2-Carboxyethyl)piperidin-4-yl]-3-(7-methyl-6,7,8,9-tetrahydro-5H-pyrazino[2,3-d]azepin-2-yl)imidazolidin-2-one trihydrochloride Melting point: from 247° C. (decomposition)

R$_f$: 0.71 (reversed phase silica gel; methanol/5% aqueous brine=6:4)

(4) 1-[1-(1-Carboxy-2-propyl)piperidin-4-yl]-3-(7-methyl-6,7,8,9-tetrahydro-5H-pyrazino[2,3-d]azepin-2-yl)imidazolidin-2-one trihydrochloride Melting point: 233°–234° C. (decomposition)

R$_f$: 0.67 (reversed phase silica gel; methanol/5% aqueous brine=6:4)

(5) 1-[1-(2-Carboxy-1-propyl)piperidin-4-yl]-3-(7-methyl-6,7,8,9-tetrahydro-5H-pyrazino[2,3-d]azepin-2-yl)imidazolidin-2-one trihydrochloride Melting point: from 190° C. (decomposition)

R$_f$: 0.69 (reversed phase silica gel; methanol/5% aqueous brine=6:4)

(6) 1-[1-(2-Carboxy-1-propyl)piperidin-4-yl]-3-(7-ethyl-6,7,8,9-tetrahydro-5H-pyrazino[2,3-d]azepin-2-yl)imidazolidin-2-one trihydrochloride R$_f$: 0.64 (reversed phase silica gel; methanol/5% aqueous brine=6:4)

Mass spectrum: (M+H)$^+$=431

(7) 1-[1-(1-Carboxy-2-propyl)piperidin-4-yl]-3-(7-ethyl-6,7,8,9-tetrahydro-5H-pyrazino[2,3-d]azepin-2-yl)imidazolidin-2-one trihydrochloride R$_f$: 0.15 (silica gel; methylene chloride/methanol/concentrated aqueous ammonia=9:1:0.1)

Mass spectrum: (M+H)$^+$=431

(8) 1-[1-(2-Carboxyethyl)piperidin-4-yl]-3-(7-ethyl-6,7,8,9-tetrahydro-5H-pyrazino[2,3-d]azepin-2-yl)imidazolidin-2-one trihydrochloride Melting point: 274°–280° C.

(9) 1-[trans-4-[(Carboxymethyl)oxy]cyclohexyl]-3-(7-ethyl-6,7,8,9-tetrahydro-5H-pyrazino[2,3-d]azepin-2-yl)imidazolidin-2-one dihydrochloride Melting point: 223°–225° C.

Mass spectrum: M$^+$=417

(10) 1-[4-(2-Carboxyethyl)phenyl]-3-(7-ethyl-6,7,8,9-tetrahydro-5-pyrazino[2,3-d]azepin-2-yl)imidazolidin-2-one×1,4 HCl×2 H$_2$O Melting point: 280°–283° C.

| Calc.: | C | 53.21 | H | 6.58 | N | 14.10 | Cl | 10.00 |
|---|---|---|---|---|---|---|---|---|
| Found: | | 53.68 | | 6.63 | | 13.96 | | 10.20 |

(11) 3-[trans-4-(2-Carboxyethyl)cyclohexyl]-1-(7-methyl-6,7,8,9-tetrahydro-5H-pyrazino[2,3-d]azepin-2-yl)-4-methylimidazolidin-2-one dihydrochloride R$_f$: 0.40 (reversed phase silica gel; methanol/5% aqueous brine=6:4)

Mass spectrum: M$^+$=415

(12) 3-[trans-4-(2-Carboxyethyl)cyclohexyl]-1-(7-methyl-6,7,8,9-tetrahydro-5H-pyrazino[2,3-d]azepin-2-yl)-imidazolidine-2,4-dione hydrochloride R$_f$: 0.49 (reversed phase silica gel; methanol/5% aqueous brine=6:4)

| Calc.: | C | 55.81 | H | 6.69 | N | 15.50 | Cl | 7.84 |
|---|---|---|---|---|---|---|---|---|
| Found: | | 55.80 | | 6.72 | | 15.32 | | 7.97 |

(13) 1-[trans-4-(2-Carboxyethyl)cyclohexyl]-3-(7-methyl-6,7,8,9-tetrahydro-5H-pyrazino[2,3-d]azepin-2-yl)-4-methylimidazolidin-2-one dihydrochloride $R_f$: 0.38 (reversed phase silica gel; methanol/5% aqueous brine=6:4)

EXAMPLE 37

3-[trans-4-(2-Methoxycarbonyl)ethyl]cyclohexyl]-1-(7-ethyl-6,7,8,9-tetrahydro-5H-pyrazino[2,3-d]azepin-2-yl)imidazolidine-2,4-dione 830 mg of ethyl (7-ethyl-6,7,8,9-tetrahydro-5H-pyrazino[2,3-d]azepin-2-yl)aminoacetate and 670 mg of trans-4-[2-(methoxycarbonyl)ethyl]cyclohexyl isocyanate are heated in an oil bath at 160° C. under nitrogen for 1 hour. After 1 hour, a further 700 mg of the isocyanate are added and the mixture is heated for a further 3 hours. After standing at room temperature overnight, the residue is mixed in 20 ml of toluene with a spatula tip of potassium tert-butoxide and heated under reflux for half an hour. It is cooled, a few drops of glacial acetic acid are added, and the mixture is concentrated. The residue is purified by chromatography on an alumina column with methylene chloride and subsequent crystallization from methanol.

Yield: 0.8 g (62% of theory),

Melting point: 168°–170° C.

$R_f$: 0.78 (silica gel; toluene/dioxane/methanol/ammonia=20:50:20:2)

| Calc.: | C | 62.28 | H | 7.50 | N | 15.79 |
|---|---|---|---|---|---|---|
| Found: | | 62.15 | | 7.40 | | 15.98 |

The following compound is obtained in analogy to Example 37:
(1) 3-[trans-4-[2-(Methoxycarbonyl)ethyl]cyclohexyl]-1-(7-methyl-6,7,8,9-tetrahydro-5H-pyrazino[2,3-d]azepin-2-yl)imidazolidine-2,4-dione Melting point: 121°–123° C.

| Calc.: | C | 60.76 | H | 7.32 | N | 16.10 |
|---|---|---|---|---|---|---|
| Found: | | 60.97 | | 7.28 | | 15.96 |

EXAMPLE 38

1-[1-[2-(Ethoxycarbonyl)ethyl]piperidin-4-yl]-3-(7-methyl-6,7,8,9-tetrahydro-5H-pyrazino[2,3-d]azepin-2-yl)imidazolidin-2-one 600 mg of 1-(4-piperidinyl)-3-(7-methyl-6,7,8,9-tetrahydro-5H-pyrazino[2,3-d]azepin-2-yl)imidazolidin-2-one and 1.35 g of ethyl acrylate are heated under reflux in 10 ml of ethanol for 5 hours. The residue after evaporation is purified by chromatography on an alumina column with cyclohexane/methylene chloride/methanol=(40:60:1).

Yield: 310 mg (40% of theory),

Melting point: 119°–121° C.

$R_f$: 0.36 (alumina; cyclohexane/methylene chloride/methanol=30:70:1)

The following compounds are obtained in analogy to Example 38:

(1) 1-[1-[1-(Ethoxycarbonyl)-2-propyl]piperidin-4-yl]-3-(7-methyl-6,7,8,9-tetrahydro-5H-pyrazino[2,3-d]azepin-2-yl)imidazolidin-2-one Carried out with ethyl crotonate $R_f$: 0.35 (alumina; methylene chloride/methanol=100:1)

(2) 1-[1-[2-(Methoxycarbonyl)-1-propyl]piperidin-4-yl]-3-(7-methyl-6,7,8,9-tetrahydro-5H-pyrazino[2,3-d]azepin-2-yl)imidazolidin-2-one Carried out with methyl methacrylate $R_f$: 0.40 (alumina; methylene chloride/methanol=100:1)

(3) 1-[1-[2-(Methoxycarbonyl)-1-propyl]piperidin-4-yl]-3-(7-ethyl-6,7,8,9-tetrahydro-5H-pyrazino[2,3-d]azepin-2-yl)imidazolidin-2-one Carried out with methyl methacrylate $R_f$: 0.50 (silica gel; methylene chloride/methanol/concentrated aqueous ammonia=9:1:0.1)

(4) 1-[1-[1-(Methoxycarbonyl)-2-propyl]piperidin-4-yl]-3-(7-ethyl-6,7,8,9-tetrahydro-5H-pyrazino[2,3-d]azepin-2-yl)imidazolidin-2-one Carried out with methyl crotonate $R_f$: 0.50 (silica gel; methylene chloride/methanol/concentrated aqueous ammonia=9:1:0.1)

(5) 1-[1-[2-(Ethoxycarbonyl)ethyl]piperidin-4-yl]-3-(7-ethyl-6,7,8,9-tetrahydro-5H-pyrazino[2,3-d]azepin-2-yl)-3H-imidazol-2-one Melting point: 118°–120° C.

EXAMPLE 39

1-[trans-4-[2-(Methoxycarbonyl)ethyl]cyclohexyl]-3-(7-benzyl-6,7,8,9-tetrahydro-5H-pyrazino[2,3-d]azepin-2-yl)imidazolidin-2-one 1.5 g of 1-[trans-4-[2-(methoxycarbonyl)ethyl]cyclohexyl]-3-(6,7,8,9-tetrahydro-5H-pyrazino[2,3-d]azepin-2-yl)imidazolidin-2-one, 480 mg of benzyl chloride, 520 mg of N-ethyldiisopropylamine and 100 mg of sodium iodide are heated under reflux in 20 ml of acetonitrile for 1 hour. The mixture is cooled, and the solid is filtered off with suction and purified by chromatography on an alumina column with methylene chloride/methanol (99:1).

Yield: 1.26 g (69% of theory),

Melting point: 166°–168° C.

| Calc.: | C | 68.41 | H | 7.58 | N | 14.24 |
|---|---|---|---|---|---|---|
| Found: | | 68.38 | | 7.59 | | 14.18 |

EXAMPLE 40

1-[trans-4-[2-(Ethoxycarbonyl)ethyl]cyclohexyl]-3-(7-methyl-6,7,8,9-tetrahydro-5H-pyrazino[2,3-d]azepin-2-yl)imidazolidin-2-one Gaseous hydrogen chloride is passed into 1.0 g of 1-[trans-4-(2-carboxyethyl)cyclohexyl]-3-(7-methyl-6,7,8,9-tetrahydro-5H-pyrazino[2,3-d]azepin-2-yl)imidazolidin-2-one in 30 ml of ethanol for 10 minutes and the mixture is subsequently heated under reflux for 1 hour. After standing at room temperature overnight, it is again heated to reflux, cooled and concentrated. The residue is stirred with dilute aqueous sodium carbonate solution. The solid is filtered off with suction, washed with water and dried.

Yield: 0.95 g (93% of theory),

Melting point: 148°–151° C.

EXAMPLE 41

1-[4-[2-(Methoxycarbonyl)ethyl]phenyl]-3-(7-ethyl-6,7,8,9-tetrahydro-5H-pyrazino[2,3-d]azepin-2-yl)imidazolidin-2-one 1.51 g of triphenylphosphine and 0.95 ml of diethyl azodicarboxylate are added to 2.54 g of N-(2-hydroxyethyl)

-N-[4-[2-methoxycarbonyl)ethyl]phenyl]-N'-(7-ethyl-6,7,8,9-tetrahydro-5H-pyrazino[2,3-d]azepin-2-yl)urea in 12.5 ml of acetonitrile, and the mixture is then stirred at room temperature for 2 hours. The solid is filtered off with suction, stirred with a little acetonitrile and again filtered off with suction. The solid is stirred with 20 ml of tert-butyl methyl ether, filtered off with suction, washed with tert-butyl methyl ether and dried.

Yield: 0.57 g (23% of theory)

Melting point: 170°–172° C.

The following compound is obtained in analogy to Example 41:

(1) 1-[trans-4-[2-(Methoxycarbonyl)ethyl]cyclohexyl]-3-(7-methyl-6,7,8,9-tetrahydro-5H-pyrazino[2,3-d]azepin-2-yl)-4-methylimidazolidin-2-one Melting point: 94°–96° C.

$R_f$: 0.40 (silica gel; methylene chloride/methanol/concentrated aqueous ammonia=9:1:0.1)

EXAMPLE 42

Dry ampoule with 2.5 mg of active substance per 1 ml

| Composition: | |
| --- | --- |
| Active substance | 2.5 mg |
| Mannitol | 50.0 mg |
| Water for injections ad | 1.0 ml |

Preparation

Active substance and mannitol are dissolved in water. The charged ampoules are freeze-dried. Water for injections is used to dissolve to give the solution ready for use.

EXAMPLE 43

Dry ampoule with 35 mg of active substance per 2 ml

| Composition: | |
| --- | --- |
| Active substance | 35.0 mg |
| Mannitol | 100.0 mg |
| Water for injections ad | 2.0 ml |

Preparation

Active substance and mannitol are dissolved in water. The charged ampoules are freeze-dried. Water for injections is used to dissolve to give the solution ready for use.

EXAMPLE 44

Tablet with 50 mg of active substance
Composition

| (1) Active substance | 50.0 mg |
| --- | --- |
| (2) Lactose | 98.0 mg |
| (3) Corn starch | 50.0 mg |
| (4) Polyvinylpyrrolidone | 15.0 mg |
| (5) Magnesium stearate | 2.0 mg |
| | 215.0 mg |

Preparation (1), (2) and (3) are mixed and granulated with an aqueous solution of (4). The dried granules are mixed with (5). Tablets, biplanar with bevel on both sides and score on one side, are compressed from this mixture. Diameter of the tablets: 9 mm.

EXAMPLE 45

Tablet with 350 mg of active substance
Composition

| (1) Active substance | 350.0 mg |
| --- | --- |
| (2) Lactose | 136.0 mg |
| (3) Corn starch | 80.0 mg |
| (4) Polyvinylpyrrolidone | 30.0 mg |
| (5) Magnesium stearate | 4.0 mg |
| | 600.0 mg |

Preparation (1), (2) and (3) are mixed and granulated with an aqueous solution of (4). The dried granules are mixed with (5). Tablets, biplanar with bevel on both sides and score on one side, are compressed from this mixture. Diameter of the tablets: 12 mm.

EXAMPLE 46

Capsules with 50 mg of active substance
Composition

| (1) Active substance | 50.0 mg |
| --- | --- |
| (2) Corn starch, dried | 58.0 mg |
| (3) Lactose, powdered | 50.0 mg |
| (3) Magnesium stearate | 2.0 mg |
| | 160.0 mg |

Preparation (1) is triturated with (3). This trituration is added to the mixture of (2) and (4) with vigorous mixing.

This powder mixture is packed into hard gelatin 2-piece capsules, size 3, in a capsule-filling machine.

EXAMPLE 47

Capsules with 350 mg of active substance
Composition

| (1) Active substance | 350.0 mg |
| --- | --- |
| (2) Corn starch, dried | 46.0 mg |
| (3) Lactose, powdered | 30.0 mg |
| (3) Magnesium stearate | 4.0 mg |
| | 430.0 mg |

Preparation (1) is triturated with (3). This trituration is added to the mixture of (2) and (4) with vigorous mixing.

This powder mixture is packed into hard gelatin 2-piece capsules, size 0, in a capsule-filling machine.

What is claimed is:

1. An imidazolidinone of formula $$Y \diagdown \begin{array}{c} N-R_b \\ | \\ N \\ | \\ R_a \end{array} \diagup O \quad (I)$$

wherein

Y represents a —CH$_2$CH$_2$—, —CH$_2$CH$_2$CH$_2$—, —CH=CH—, —CH=N—, —N=CH—, —CH$_2$CO— or —COCH$_2$— group optionally substituted by R$_c$, or by R$_c$ and R$_d$, and which may additionally be substituted by one or two alkyl groups;

a first of the groups $R_a$ to $R_d$ represents a group of formula

A—B— wherein

A is a group of the formula

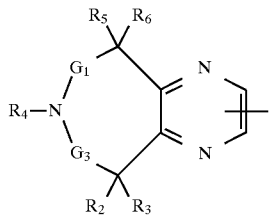

wherein the pyrazino moiety of the above-mentioned group may be substituted by an alkyl, trifluoromethyl, hydroxy or alkoxy group, $G_1$ represents a methylene group which may be mono or disubstituted by an alkyl group, whilst the substituents may be identical or different, $G_3$ represents a methylene group substituted by $R_9$ and $R_{10}$, $R_2$ represents a hydrogen atom or an alkyl group, $R_3$ represents a hydrogen atom or an alkyl group, $R_4$ represents a hydrogen atom, a cycloalkyl or cycloalkylalkyl group each having 3 to 7 carbon atoms in the cycloalkyl moiety, a $C_{1-6}$-alkyl group, a $C_{3-6}$-alkenyl group (which alkenyl group may not be linked to the nitrogen atom via the vinyl group), or a hydroxyalkyl, alkoxyalkyl, carboxyalkyl, alkoxycarbonylalkyl, aminocarbonylalkyl, N-alkylaminocarbonylalkyl, N,N-dialkylaminocarbonylalkyl, arylalkyl, alkoxycarbonyl, arylmethyloxycarbonyl, formyl, acetyl or trifluoroacetyl group, $R_5$ represents a hydrogen atom or an alkyl group, $R_6$ represents a hydrogen atom or an alkyl group, $R_9$ represents a hydrogen atom or an alkyl group, $R_{10}$ represents a hydrogen atom or an alkyl group, and B represents a bond, an alkylene group, an arylene group, or a cyclcohexylene group;

a second of the groups $R_a$ to $R_d$ represents a group of formula

F—E—D— wherein

D represents a bond, an alkylene group, an arylene group, a $C_{4-7}$-cycloalkylene group optionally substituted by 1 or 2 alkyl groups, or a piperidinylene group;

E represents a bond, an alkylene group which may be substituted by a $C_{1-6}$-alkyl group, or by an amino, aryl, alkylamino, dialkylamino, $HNR_{21}$ or N-alkyl-$NR_{21}$— group, (wherein $R_{21}$ represents an alkylcarbonyl or alkylsulphonyl group each having 1 to 6 carbon atoms in the alkyl moiety, an alkyloxycarbonyl group having a total of 2 to 5 carbon atoms, a cycloalkylcarbonyl or cycloalkylsulphonyl group each having 5 to 7 carbon atoms in the cycloalkyl moiety, an arylalkylcarbonyl, arylalkylsulphonyl, arylalkoxycarbonyl, arylcarbonyl or arylsulphonyl group), a $C_{2-4}$-alkenylene group, an arylene group, a $C_{4-7}$-cycloalkylene optionally substituted by one or two alkyl groups, or E may also represent an alkylene group linked to the group D via a group W, wherein W represents an oxygen or sulphur atom or a sulphinyl, sulphonyl, —$NR_{20}$—CO— or —CO—$NR_{20}$ group, wherein $R_{20}$ represents a hydrogen atom or an alkyl group and the alkylene group may additionally be substituted by a $C_{1-6}$-alkyl group, by an amino, aryl, alkylamino, dialkylamino, $HNR_{21}$ or N-alkyl-$NR_{21}$— group, wherein the heteroatom of the additional substituent is separated from a heteroatom of group W by at least two carbon atoms and $R_{21}$ is as hereinbefore defined; and F represents a carbonyl group substituted by a hydroxy, alkoxy, arylalkoxy or $R_{22}O$ group (wherein $R_{22}$ represents a $C_{5-7}$-cycloalkyl group or a cycloalkylalkyl group having 5 to 7 carbon atoms in the cycloalkyl moiety), and the shortest distance between the group F and the nitrogen atom of the 7-membered ring of group A is at least 11 bonds;

$R_c$ represents a hydrogen atom, an alkyl, trifluoromethyl or aryl group; and $R_d$ represents a hydrogen atom or an alkyl group;

whilst unless otherwise specified each of the aryl moieties mentioned in the definition of the above groups is to a phenyl group which may be monosubstituted by $R_{25}$, mono, di or trisubstituted by $R_{26}$, or monosubstituted by $R_{25}$ and additionally mono or disubstituted by $R_{26}$, wherein the substituents may be identical or different and $R_{25}$ represents a cyano, aminocarbonyl, alkylaminocarbonyl, dialkylaminocarbonyl, alkylcarbonyl, alkylsulphenyl, alkylsulphinyl, alkylsulphonyl or trifluoromethyl group and $R_{26}$ represents an alkyl, hydroxy or alkoxy group, or a fluorine, chlorine or bromine atom, whilst two groups $R_{26}$, if they are bound to adjacent carbon atoms, may also represent a straight chain $C_{3-4}$-alkylene group, a 1,3-butadien-1,4-diylene group or a methylenedioxy group, and each arylene moiety mentioned in the definition of the above-mentioned groups is a phenylene group which may be monosubstituted by $R_{25}$, mono or disubstituted by $R_{26}$, or monosubstituted by $R_{25}$ and additionally monosubstituted by $R_{26}$, wherein the substituents may be identical or different and are defined as hereinbefore;

and unless otherwise specified, the above-mentioned alkyl, alkylene or alkoxy moieties may each contain 1 to 4 carbon atoms, and each carbon atom in the above mentioned alkylene and cycloalkylene moieties is linked to one heteroatom at most;

a tautomer, or stereoisomer thereof, or a salt thereof.

2. The imidazolidinone of formula I according to claim 1, wherein:

Y represents a —$CH_2CH_2$—, —CH=CH—, —CH=N—, —N=CH—, —$CH_2CO$— or —$COCH_2$— group optionally substituted by one or two methyl groups;

$R_a$ represents a group of formula

A—B— wherein

A is a group of the formula

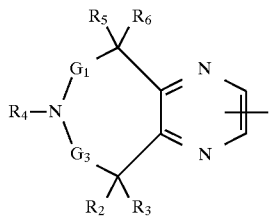

wherein $G_1$ represents a methylene group, $G_3$ represents a methylene group, $R_2$ represents a hydrogen atom, $R_3$ represents a hydrogen atom, $R_4$ represents a hydrogen atom, a $C_{1-6}$-alkyl, cyclopropyl, cyclohexyl, cyclopropylmethyl, cyclohexylmethyl, 2-hydroxy-ethyl, allyl, benzyl, carboxymethyl or $C_{1-2}$-alkoxymethyl group, $R_5$ represents a hydrogen atom, $R_6$ represents a hydrogen atom, and B represents a bond;

$R_b$ represents a group of formula

F—E—D— wherein

D represents a phenylene or cyclohexylene group or a 1,4-piperidinylene group in which the nitrogen atom is linked to an optionally substituted alkylene group of group E;

E represents a straight-chained alkylene group which may be substituted by an alkyl or phenyl group, a $C_{2-4}$-alkenylene group, or E may also represent a straight-chained O-alkylene group linked to the group D via the oxygen atom; and F represents a carbonyl group substituted by a hydroxy, alkoxy or $C_{5-6}$-cycloalkoxy group;

whilst unless otherwise specified the above-mentioned alkyl, alkylene or alkoxy moieties may each contain 1 to 4 carbon atoms, and each carbon atom in the above mentioned alkylene and cycloalkylene moieties is linked to one heteroatom at most and each of the above-mentioned phenyl or phenylene groups may be substituted by a fluorine, chlorine or bromine atom, by a methyl or methoxy group;

or a tautomer or stereoisomer thereof, or a salt thereof.

3. The imidazolidinone of formula I according to claim 1, wherein:

Y represents a —$CH_2CH_2$—, —CH=CH—, —$CH_2CO$— or —$COCH_2$— group, whereby these groups can be substituted by a methyl group;

$R_a$ represents a group of formula

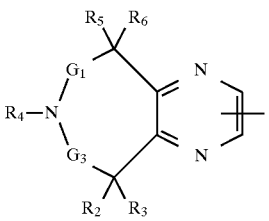

wherein $G_1$ represents a methylene group, $G_3$ represents a methylene group, $R_2$ represents a hydrogen atom, $R_3$ represents a hydrogen atom, $R_4$ represents a hydrogen atom, a $C_{1-4}$-alkyl, cyclopropylmethyl, allyl or benzyl group, $R_5$ represents a hydrogen atom, $R_6$ represents a hydrogen atom, and B represents a bond;

$R_b$ represents a group of formula

F—E—D— wherein

D represents a 1,4-phenylene or 1,4-cyclohexylene group or a 1,4-piperidinylene group in which the nitrogen atom is linked to a —$CH_2CH_2$— group optionally substituted by a methyl group of group E;

E represents a —$CH_2CH_2$— group optionally substituted by a methyl group or a —$OCH_2$— group wherein the oxygen atom is linked to group D; and F represents a carbonyl group substituted by a hydroxy or $C_{1-4}$-alkoxy group;

or a tautomer or stereoisomer thereof, or a salt thereof.

4. The imidazolidinone of formula I according to claim 1, wherein:

Y represents a —$CH_2CH_2$—, —CH=CH—, —$CH_2CO$— or —$COCH_2$— group where these groups can be substituted by a methyl group;

$R_a$ represents a group of formula

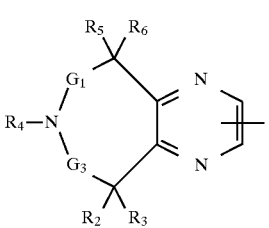

wherein $G_1$ represents a methylene group, $G_3$ represents a methylene group, $R_2$ represents a hydrogen atom, $R_3$ represents a hydrogen atom, $R_4$ represents a hydrogen atom, a $C_{1-4}$-alkyl or benzyl group, $R_5$ represents a hydrogen atom, $R_6$ represents a hydrogen atom, and B represents a bond;

$R_b$ represents a group of formula

F—E—D— wherein
- D represents a 1,4-phenylene or 1,4-cyclohexylene group or a 1,4-piperidinylene group in which the nitrogen atom is linked to a —CH$_2$CH$_2$— group optionally substituted by a methyl group of group E;
- E represents a —CH$_2$CH$_2$— group optionally substituted by a methyl group or a —O—CH$_2$— group where the oxygen atom is linked to group E; and
- F represents a carbonyl group substituted by a hydroxy or C$_{1-4}$-alkoxy group;

or a tautomer or stereoisomer thereof, or a salt thereof.

5. The imidazolidinone of formula I according to claim 1:

(a) 1-[trans-4-(2-carboxyethyl)cyclohexyl]-3-(7-methyl-6,7,8,9-tetrahydro-5H-pyrazino[2,3-d]azepin-2-yl)-imidazolidin-2-one or a salt thereof;

(b) 3-[trans-4-(2-carboxyethyl)cyclohexyl]-1-(7-methyl-6,7,8,9-tetrahydro-5H-pyrazino[2,3-d]azepin-2-yl)-imidazolidin-2,4-dione, or a salt thereof.

6. 1-[trans-4-(2-carboxyethyl)cyclohexyl]-3-(7-methyl-6,7,8,9-tetrahydro-5H-pyrazino[2,3-d]azepin-2-yl)-imidazolidin-2-one, or a salt thereof.

7. 3-[trans-4-(2-carboxyethyl)cyclohexyl]-1-(7-methyl-6,7,8,9-tetrahydro-5H-pyrazino[2,3-d]azepin-2-yl)-imidazolidin-2,4-dione, or a salt thereof.

* * * * *